(12) United States Patent
Wong et al.

(10) Patent No.: US 9,340,812 B2
(45) Date of Patent: May 17, 2016

(54) LARGE SCALE ENZYMATIC SYNTHESIS OF OLIGOSACCHARIDES

(71) Applicant: Academia Sinica, Taipei (TW)

(72) Inventors: Chi-Huey Wong, Rancho Santa Fe, CA (US); Tsung-I Tsai, Taipei (TW); Chung-Yi Wu, New Taipei (TW)

(73) Assignee: Academia Sinica, Taipei (TW)

( * ) Notice: Subject to any disclaimer, the term of this patent is extended or adjusted under 35 U.S.C. 154(b) by 7 days.

(21) Appl. No.: 13/971,353

(22) Filed: Aug. 20, 2013

(65) Prior Publication Data

US 2014/0051127 A1    Feb. 20, 2014

Related U.S. Application Data

(60) Provisional application No. 61/684,974, filed on Aug. 20, 2012.

(51) Int. Cl.
   *C12P 19/18*    (2006.01)

(52) U.S. Cl.
   CPC ..................... *C12P 19/18* (2013.01)

(58) Field of Classification Search
   None
   See application file for complete search history.

(56) References Cited

U.S. PATENT DOCUMENTS

| | | | |
|---|---|---|---|
| 6,319,695 B1 * | 11/2001 | Wong et al. | ............ 435/97 |
| 2002/0034805 A1 | 3/2002 | Gilbert et al. | |
| 2007/0202578 A1 | 8/2007 | Samain et al. | |
| 2011/0046003 A1 | 2/2011 | Wong et al. | |

OTHER PUBLICATIONS

Zhang et al., Large-scale synthesis of globotriose derivatives through recombinant E. coli., Org. Biomol. Chem. (2003), vol. 1, pp. 3048-3053.*
P0A7A9 (last viewed on Mar. 4, 2015).*
Chi-Huey Wong, Carbohydrate-based Drug Discovery (2003), Wiley-VCH, vol. 1, p. 146.*
P0A610 created in 2005 (last viewed on Mar. 4, 2015).*
Koizumi et al., Large-scale production of UDP-galactose and globotriose by coupling metabolically engineered bacteria. Nat Biotechnol. Sep. 1998;16(9):847-50.
Lee et al., Optimization of the enzymatic one pot reaction for the synthesis of uridine 5'-diphosphogalactose. Bioprocess Biosyst Eng. Jan. 2010;33(1):71-8. doi: 10.1007/s00449-009-0365-2.

* cited by examiner

*Primary Examiner* — Alexander Kim
(74) *Attorney, Agent, or Firm* — Fanelli Haag PLLC

(57) ABSTRACT

A novel UDP-Gal regeneration process and its combined use with a galactosyltransferase to add galactose to a suitable acceptor substrate. Also described herein are synthetic methods for generating Globo-series oligosaccharides in large scale, wherein the methods may involve the combination of a glycosyltransferase reaction and a nucleotide sugar regeneration process.

32 Claims, 14 Drawing Sheets

Allyl-Gb3

Allyl-Gb4

Allyl-Gb5

Allyl-Globo H

Allyl SSEA4

LARGE SCALE ENZYMATIC SYNTHESIS OF OLIGOSACCHARIDES

RELATED APPLICATIONS

The present application claims priority under 35 U.S.C. §119(e) to U.S. Provisional Patent Application No. 61/684,974, filed Aug. 20, 2012, which is herein incorporated by reference in its entirety.

BACKGROUND

Globopentaose (Gb5), fucosyl-Gb5 (Globo H), and sialyl-Gb5 (SSEA4) are globo-series glycosphingolipid and were first discovered in 1983 in cultured human teratocarcinoma cell line[1] and subsequently found in several malignant cancers.[2],[3] Report showed Globo H overexpression in up to 61%, Gb5 overexpression in 77.5% and SSEA4 overexpression in 95% in breast cancer patients.[4] On the other hand, HER2 gene, the target for therapeutic monoclonal antibody Trastuzumab (Herceptin) that interferes with the HER2/neu receptor, is overexpressed in only 25% breast cancer patients[5]. The comparison clearly demonstrated that the glycosphingolipid antigens (Gb5 and its derivative, Globo H and SSEA4) are better candidates to be developed into cancer vaccine. Hence, Globo H has been conjugated to the keyhole limpet hemocyanin (KLH) as a cancer vaccine, and is under phase III clinical trial in some country now.[6]

There are several disadvantages of current methods used for the synthesis of Gb5, Globo H and SSEA4. The traditional chemical synthesis is tedious and labor-consuming, and several protection and de-protection steps are necessary to achieve high purity and correct stereotype and always lead to the very low total yields. Till now there are many reports for the chemical synthesis of Globo H[7][8][9][10][11][12][13][14] However, only two reports have been published for SSEA4 synthesis. Hsu et al reported a one-pot chemical synthesis approach to assembled the glycan part of SSEA-4 in 24% yield[15] Zhen et al. reported the use of a chemoenzymatic method to synthesize SSEA-4 in milligram scale.[16] On the other hand, the enzymatic synthesis of Globo H based on Leloir-type glycosyltransferase only requires the active nucleotide sugar as donor to catalyze the glycosylation reaction. Nonetheless, the nucleotide sugar is too expensive to synthesize in large scale. Moreover, the by-product pyrophosphate and nucleoside diphosphate inhibit the nucleotide sugar formation of pyrophosphorylase[15] and Leloir-type glycosyltransferase; therefore, how to develop a regeneration strategy is necessary to overcome the limitation and to recharge the nucleotide to achieve constitute nucleotide sugar product in order to continue the reaction. During the past several years, many groups worked to tackle the major problem of nucleotide sugar regeneration and most of the sugar nucleotide regeneration have been solved. However, there is still some space to improve the technology of sugar nucleotide regeneration, especially the UDP-Gal regenerate is much difficult. For example, UDP-Gal regeneration was first proposed in 1982 by Wong and Whiteside via UDP-Glc C4 epimerase to interconverse UDP-Glc and UDP-Gal ([17]). Ten years later, our group developed the secondary UDP-Gal regeneration method. Instead of using UDP-Glc C4 epimerase, Glc-1-phosphate uridylyltransferase located in galactose operon in E. coli was used to interchange Gal-1-phosphate and UDP-Glc to Glc-1-phosphate and UDP-Gal.[18] However, the final pathway to directly condense UTP and Gal-1-phosphate to form UDP-Gal was not established due to the absence of suitable enzyme. Because the target compounds Gb5, Globo H and SSEA4 are Gal-related molecules, how to overcome the major difficult of UDP-Gal regeneration and increase its efficiency will be the key point for large scale enzymatic synthesis of Gb5, Globo H and SSEA4.

In summary, there are several limitations to current methods of large scale synthesizing Gb5, Globo H and SSEA4 in the art. Thus, there is a need for new synthetic procedures that produce Gb5, Globo H, SSEA4, and intermediates thereto in an efficient manner.

SUMMARY OF THE INVENTION

The present disclosure is based on the development of new nucleotide sugar regeneration processes and their applications in sugar synthesis. Such sugar synthesis methods, involving the combination of at least one nucleotide sugar regeneration system (e.g., the UDP-Gal regeneration system described herein) and at least one glycosyltransferase (e.g., galactosyltransferase), were used in synthesizing various oligosaccharides (tailed), including allyl-tailed Gb3, Gb4, Gb5 (also known as SSEA3), Fucosyl-Gb5 (also known as Globo H), and Sialyl-Gb5 (also known as SSEA4), with unexpectedly high efficiency and yields. More specifically, the synthetic approaches described herein unexpectedly allow chain reactions to produce final products, such as Globo H and SSEA4, without the need to purify intermediates.

Accordingly, one aspect of the present disclosure relates to methods for adding a galactose residue to a substrate via the action of a galactosyltransferase coupled with a UDP-Gal regeneration process. The method comprises: (i) producing UDP-Gal from galactose in the presence of a set of UDP-Gal regeneration enzymes, wherein the set of UDP-Gal regeneration enzymes comprises a galactokinase, an UDP-sugar pyrophosphorylase, a pyruvate kinase, and optionally, a pyrophosphatase; (ii) reacting the UDP-Gal with a substrate molecule (e.g., a polysaccharide, an oligosaccharide, a glycoprotein, a glycolipid, or an aglycone) via action of a galactosyltransferase (e.g., an alpha1,4-galactosyltransferase, a beta1,4-galactosyltransferase, an alpha1,3-galactosyltransferase, or a beta1,3-galactosyltransferase) to add a galactose residue to the substrate molecule; and, optionally, (iii) isolating the galactosylated product thus produced. Steps (i) and (ii) can take place in a reaction mixture comprising the set of UDP-Gal regeneration enzymes, the galactosyltransferase, the substrate molecule, galactose, ATP, and UTP. In some examples, the substrate molecule is a ceramide or a glycosphingolipid.

Another aspect of the present disclosure relates to methods for synthesizing oligosaccharides involving at least one nucleotide sugar regeneration process (e.g., UDP-Gal regeneration) and at least one reaction of adding a monosaccharide, e.g., galactose (Gal), N-acetylgalatocoamine (GalNAc), fucose (Fuc), and sialic acid (Neu5Ac), onto a suitable acceptor via action of a glycosyltranferase, e.g., galactosyltransferase, fucosyltransferase, sialyltransferase, and N-acetylgalactosaminyltransferase.

In some embodiments, the method described herein for enzymatically synthesizing an oligosaccharide, uses lactose (e.g., tailed) as the starting material. The method comprises: (i) producing UDP-Gal from galactose in the presence of a set of UDP-Gal regeneration enzymes, wherein the set of UDP-Gal regeneration enzymes comprises a galactokinase (e.g., from E. coli), an UDP-sugar pyrophosphorylase (e.g., from A. thaliana), a pyruvate kinase (e.g., from E. coli), and optionally, a pyrophosphatase (e.g., from E. coli); (ii) converting Lac-OR$^{1A}$ into Gb3-OR$^{1A}$ in the presence of the UDP-Gal and an alpha-1,4 galactosyltransferase (e.g., a LgtC such as that from N. meningitides), wherein R$^{1A}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group. Lac-OR$^{1,4}$ refers to lactose (β-D-galactopyranosyl-(1→4)-D-glucose) (e.g., also encompassed by Formula (I), wherein each of $R^{2,4}$, $R^{3,4}$, $R^{5,4}$, $R^{2B}$, $R^{3B}$, and $R^{5B}$ is hydrogen) wherein the group attached to the anomeric carbon of lactose is an —OR$^{1,4}$ group, and wherein $R^{1,4}$ is as defined herein.

Examples of $R^{1,4}$ include, but are not limited to hydrogen, allyl, biotin, a ceramide, or a non-hydrogen group (e.g., alkyl) which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, $R^{1,4}$ is hydrogen, allyl, substituted alkyl, biotin, or a ceramide.

When necessary, Gb3-OR$^{1,4}$ can be isolated from the reaction mixture.

Steps (i) and (ii) can occur in a Gb3-synthesis reaction mixture comprising galactose, PEP, ATP, UTP, the Lac-OR$^{1,4}$, the alpha-1,4-galactosyltransferase, and the set of UDP-Gal regeneration enzymes. In one example, the molar ratio of the Lac-OR$^{1,4}$ and galactose in the Gb3-synthesis reaction mixture is 1:1 before occurrence of any enzymatic reactions.

Any of the methods described above can further comprise: (iii) converting the Gb3-OR$^{1,4}$ into Gb4-OR$^{1,4}$ in the presence of UDP-GalNAc and a beta1,3-N-acetylgalactosaminyltransferase (e.g., a LgtD from a suitable organism such as *H. influenza*), which can be coupled with (iv) producing the UDP-GalNAc from GalNAc in the presence of a set of UDP-GalNAc regeneration enzymes, wherein the set of UDP-GalNAc regeneration enzymes comprises an N-acetylhexosamine 1-kinase (e.g., from *B. longum*), an N-acetylglucosamine 1-phosphate uridyltransferase (e.g., from *E. coli*), and a pyruvate kinase (e.g., from *E. coli*), and optionally, a pyrophosphatase (e.g., from *E. coli*). Steps (iii) and (iv) can be carried out in a Gb4-synthesis reaction mixture comprising GalNAc, PEP, ATP, UTP, the Gb3-OR$^{1,4}$, the beta1,3-N-acetylgalactosaminyltransferase, and the set of UDP-GalNAc regeneration enzymes. In one example, the Gb4-synthesis reaction mixture is prepared by mixing the Gb3-synthesis reaction mixture with at least GalNAc, the beta1,3-N-acetylgalactosaminyltransferase, the N-acetylhexosamine 1-kinase, and the N-acetylglucosamine 1-phosphate uridyltransferase. When necessary, Gb4-OR$^{1,4}$ can be isolated from the reaction mixture.

After synthesis of Gb4-OR$^{1,4}$, the method as described above can further comprise: (v) converting the Gb4-OR$^{1,4}$ into Gb5-OR$^{1,4}$ in the presence of UDP-Gal and a beta1,3-galactosyltransferase (e.g., a LgtD such as that from *H. influenza*), which can be coupled with (vi) producing the UDP-Gal from galactose in the presence of the set of UDP-Gal regeneration enzymes described herein. In one example, (v) and (vi) take place in a Gb5-synthesis reaction mixture comprising galactose, PEP, ATP, UTP, the Gb4-OR$^{1,4}$, the beta1,3-galactosyltransferase, and the set of UDP-Gal regeneration enzymes. The resultant Gb5-OR$^{1,4}$ can be isolated from the reaction mixture.

The above method can further comprise steps for converting the Gb5-OR$^{1,4}$ thus obtained into Fucosyl-Gb5-OR$^{1,4}$ (Globo H) or into Sialyl-Gb5-OR$^{1,4}$ (SSEA4).

For Globo H synthesis, the method can further comprise: (vii) converting the Gb5-OR$^{1,4}$ into Fucosyl-Gb5-OR$^{1,4}$ in the presence of GDP-Fuc and an alpha1,2-fucosyltransferase (e.g., from *H. pylor*), which can be coupled with (viii) producing the GDP-Fuc from fucose in the presence of a set of GDP-Fuc regeneration enzymes, wherein the set of GDP-Fuc regeneration enzymes comprises a L-fucokinase/GDP-fucose pyrophosphorylase (e.g., *B. fragilis*), a pyruvate kinase (e.g., from *E. coli*), and a pyrophosphatase (e.g., from *E. coli*). In one example, steps (vii) and (viii) occur in a Fucosyl-Gb5-synthesis reaction mixture comprising fucose, ATP, GTP, PEP, the Gb5-OR, the alpha1,2-fucosyltransferase, and the set of GDP-Fuc regeneration enzymes. The Fucosyl-Gb5-synthesis reaction mixture can be prepared by mixing the Gb5-synthesis reaction mixture with at least fucose, GTP, the alpha1,2-fucosyltransferase, and the L-fucokinase/GDP-fucose pyrophosphorylase. When necessary, the resultant Fucosyl-Gb5-OR$^{1,4}$ can be isolated from the reaction mixture.

For SSEA4 synthesis, the method can further comprise: (ix) converting the Gb5-OR$^{1,4}$ into Sialyl-Gb5-OR$^{1,4}$ in the presence of CMP-Neu5Ac and an alpha2,3-sialyltransferase (e.g., from *M. bacteria*), and (x) producing the CMP-Neu5Ac from Neu5Ac in the presence of a set of CMP-Neu5Ac regeneration enzymes, wherein the set of CMP-Neu5Ac regeneration enzymes comprises a cytidine monophosphate kinase (e.g., from *E. coli*), a CMP-sialic acid synthetase (e.g., from *P. Multocida*), a pyruvate kinase (e.g., from *E. coli*), and optionally a pyrophosphatase (e.g., from *E. coli*). Steps (ix) and (x) can occur in a Sialyl-Gb5-synthesis reaction mixture comprising Neu5Ac, CTP, PEP, the Gb5-OR$^{1,4}$, the alpha 2,3-sialyltransferase, and the set of CMP-Neu5Ac regeneration enzymes. The Sialyl-Gb5-synthesis reaction mixture is prepared by mixing the Gb5-synthesis reaction mixture with at least Neu5Ac, CTP, the alpha 2,3-sialyltransferase, the cytidine monophosphate kinase, and the CMP-sialic acid synthetase. The Sialyl-Gb5-OR$^{1,4}$ can then be isolated from the reaction mixture.

In one example, a method for synthesizing Globo H can be performed as follows: (i) producing UDP-Gal from galactose in the presence of the UDP-Gal regeneration enzymes as described herein, (ii) converting Lac-OR$^{1,4}$ as described herein into Gb3-OR$^{1,4}$ in a Gb3-synthesis reaction mixture comprising at least the UDP-Gal, an alpha-1,4 galactosyltransferase, and the UDP-Gal regeneration enzymes, (iii) mixing the Gb3-synthesis reaction mixture with at least GalNAc, the beta1,3-N-acetylgalactosaminyltransferase, the N-acetylhexosamine 1-kinase, and the N-acetylglucosamine 1-phosphate uridyltransferase to form a Gb4-synthesis reaction mixture, (iv) incubating the Gb4-synthesis reaction mixture under conditions allowing conversion of Gb3-OR$^{1,4}$ to Gb4-OR$^{1,4}$, (v) further incubating the Gb4-synthesis reaction mixture in the presence of β-1,3-galactosyltransferase under conditions allowing conversion of the Gb4-OR$^{1,4}$ to Gb5-OR$^{1,4}$, (vi) mixing the Gb5-OR$^{1,4}$-containing reaction mixture with at least fucose, GTP, the alpha1,2-fucosyltransferase, and the L-fucokinase/GDP-fucose pyrophosphorylase to form a Fucosyl-Gb5-OR$^{1,4}$ reaction mixture; (vii) incubating the Fucosyl-Gb5-OR$^{1,4}$ reaction mixture under conditions allowing conversion of the Gb5-OR$^{1,4}$ to Fucosyl-Gb5-OR$^{1,4}$, and optionally, (viii) isolating the Fucosyl-Gb5-OR$^{1,4}$.

In another example, a method for synthesizing Globo H can be performed as follows: (i) producing UDP-Gal from galactose in the presence of the UDP-Gal regeneration enzymes as described herein, (ii) converting Lac-OR$^{1,4}$ as described herein into Gb3-OR$^{1,4}$ in a Gb3-synthesis reaction mixture comprising at least the UDP-Gal, an alpha-1,4 galactosyltransferase, and the UDP-Gal regeneration enzymes, (iii) mixing the Gb3-synthesis reaction mixture with at least GalNAc, the beta1,3-N-acetylgalactosaminyltransferase, the N-acetylhexosamine 1-kinase, and the N-acetylglucosamine 1-phosphate uridyltransferase to form a Gb4-synthesis reaction mixture, (iv) incubating the Gb4-synthesis reaction mixture under conditions allowing conversion of Gb3-OR$^{1-4}$ to Gb4-OR$^{1-4}$; (v) isolating the Gb4-OR$^{1-4}$; (vi) mixing the Gb4-OR$^{1-4}$ with a beta1,3-galactosyltransferase and the set of UDP-Gal regeneration enzymes to form a Gb5-synthesis reaction mixture; (vii) incubating the Gb5-synthesis reaction mixture under conditions allowing conversion of the Gb4-OR$^{1-4}$ to Gb5-OR$^{1-4}$, (viii) mixing the Gb5-synthesis reaction mixture with at least at least fucose, GTP, the alpha1,2-fucosyltransferase, and the L-fucokinase/GDP-fucose pyrophosphorylase to form a Fucosyl-Gb5-OR$^{1-4}$ reaction mixture; (ix) incubating the Fucosyl-Gb5-OR$^{1-4}$ reaction mixture under conditions allowing conversion of the Gb5-OR$^{1-4}$ to Fucosyl-Gb5-OR$^{1-4}$; and optionally, (x) isolating the Fucosyl-Gb5-OR$^{1-4}$.

A method for synthesizing SSEA4 can be performed as follows: (i) producing UDP-Gal from galactose in the presence of the UDP-Gal regeneration enzymes as described herein, (ii) converting Lac-OR$^{1-4}$ as described herein into Gb3-OR$^{1-4}$ in a Gb3-synthesis reaction mixture comprising at least the UDP-Gal, an alpha-1,4 galactosyltransferase, and the UDP-Gal regeneration enzymes, (iii) mixing the Gb3-synthesis reaction mixture with at least GalNAc, the beta1,3-N-acetylgalactosaminyltransferase, the N-acetylhexosamine 1-kinase, and the N-acetylglucosamine 1-phosphate uridyltransferase to form a Gb4-synthesis reaction mixture, (iv) incubating the Gb4-synthesis reaction mixture under conditions allowing conversion of Gb3-OR$^{1-4}$ to Gb4-OR$^{1-4}$, (v) further incubating the Gb4-synthesis reaction mixture in the presence of a β-1,3-galactosyltransferase under conditions allowing conversion of the Gb4-OR$^{1-4}$ to Gb5OR$^{1-4}$, (vi) mixing the Gb4-synthesis reaction mixture with at least at least Neu5Ac, CTP, the alpha2,3-sialyltransferase, the cytidine monophosphate kinase, and the CMP-sialic acid synthetase to form a Sialyl-Gb5-OR$^{1-4}$ reaction mixture; (vii) incubating the Sialyl-Gb5-OR$^{1-4}$ reaction mixture under conditions allowing conversion of the Gb5-OR$^{1-4}$ to Sialyl-Gb5-OR$^{1-4}$; and optionally, (viii) isolating the Sialyl-Gb5-OR$^{1-4}$.

Alternatively, a method for synthesizing SSEA4 can be performed as follows: (i) producing UDP-Gal from galactose in the presence of the UDP-Gal regeneration enzymes as described herein, (ii) converting Lac-OR$^{1-4}$ as described herein into Gb3-OR$^{1-4}$ in a Gb3-synthesis reaction mixture comprising at least the UDP-Gal, an alpha-1,4 galactosyltransferase, and the UDP-Gal regeneration enzymes, (iii) mixing the Gb3-synthesis reaction mixture with at least GalNAc, the beta1,3-N-acetylgalactosaminyltransferase, the N-acetylhexosamine 1-kinase, and the N-acetylglucosamine 1-phosphate uridyltransferase to form a Gb4-synthesis reaction mixture, (iv) incubating the Gb4-synthesis reaction mixture under conditions allowing conversion of Gb3-OR$^{1-4}$ to Gb4-OR$^{1-4}$; (v) isolating the Gb4-OR$^{1-4}$; (vi) mixing the Gb4-OR$^{1-4}$ with a beta1,3-galactosyltransferase and the set of UDP-Gal regeneration enzymes to form a Gb5-synthesis reaction mixture; (vii) incubating the Gb5-synthesis reaction mixture under conditions allowing conversion of the Gb4-OR$^{1-4}$ to Gb5-OR$^{1-4}$; (viii) mixing the Gb5-OR$^{1-4}$ with an alpha2,3sialyltransferase and a set of CMP-Neu5Ac regeneration enzymes to form a Sialyl-Gb5-synthesis reaction mixture, wherein the set of CMP-Neu5Ac regeneration enzymes comprises a cytidine monophosphate kinase, a CMP-sialic acid synthetase, a pyruvate kinase, and a pyrophosphatase; (ix) incubating the Sialyl-Gb5-synthesis reaction mixture under conditions allowing conversion of the Gb4-OR$^{1-4}$ to Sialyl-Gb5-OR$^{1-4}$; and optionally, (x) isolating the Sialyl-Gb5-OR$^{1-4}$.

In some embodiments, the method described herein for enzymatically synthesizing an oligosaccharide uses Gb3 (e.g., tailed) as the starting material. The method comprises: (i) producing UDP-GalNAc from GalNAc in the presence of the set of UDP-GalNAc regeneration enzymes as described above, and converting Gb3-OR$^{1-4}$ into Gb4-OR$^{1-4}$ in the presence of the UDP-GalNAc and a beta1,3-N-acetylgalactosaminyltransferase, wherein R$^{1-4}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group. Examples of R$^{1-4}$ include, but are not limited to, hydrogen, allyl, biotin, a ceramide, or a non-hydrogen group (e.g., alkyl) which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, R$^{1-4}$ is hydrogen, allyl, substituted alkyl, biotin, or a ceramide. Steps (i) and (ii) can occur in a Gb4-synthesis reaction mixture comprising GalNAc, PEP, ATP, UTP, the Gb3OR$^{1-4}$, the beta1,3-N-acetylgalactosaminyltransferase, and the set of UDP-GalNAc regeneration enzymes. The Gb4-OR$^{1-4}$ can be isolated if necessary.

The above method can further comprise: (iii) converting the Gb4-OR$^{1-4}$ into Gb5-OR$^{1-4}$ in the presence of UDP-Gal and a beta1,3-galactosyltransferase, which can be coupled with (iv) producing the UDP-Gal from galactose in the presence of the set of UDP-Gal regeneration enzymes as described herein. (iii) and (iv) can take place in a Gb5-synthesis reaction mixture comprising galactose, PEP, ATP, UTP, the Gb4-OR$^{1-4}$, the beta1,3-galactosyltransferase, and the set of UDP-Gal regeneration enzymes. The resultant Gb5-OR$^{1-4}$ can be isolated from the reaction mixture.

In one example, the Gb5-OR$^{1-4}$ is then converted into Fucosyl-Gb5-OR$^{1-4}$ as follows: (v) converting the Gb5-OR$^{1-4}$ into Fucosyl-Gb5-OR$^{1-4}$ in the presence of GDP-Fuc and an alpha1,2-fucosyltransferase, which can be coupled with (vi) producing the GDP-Fuc from fucose in the presence of the set of GDP-Fuc regeneration enzymes described herein. Steps (v) and (vi) can be carried out in a Fucosyl-Gb5-synthesis reaction mixture comprising fucose, ATP, GTP, PEP, the Gb5-OR$^{1-4}$, the alpha1,2-fucosyltransferase, and the set of GDP-Fuc regeneration enzymes. When desired, the Fucosyl-Gb5-synthesis reaction mixture is prepared by mixing the Gb5-synthesis reaction mixture with at least fucose, GTP, the alpha1,2-fucosyltransferase, and the L-fucokinase/GDP-fucose pyrophosphorylase. The method can further comprise isolating the Fucosyl-Gb5-OR$^{1-4}$.

In another example, the Gb5-OR$^{1-4}$ is then converted into Sialyl-Gb5-OR$^{1-4}$ as follows: (vii) converting the Gb5-OR$^{1-4}$ into Sialyl-Gb5-OR$^{1-4}$ in the presence of CMP-Neu5Ac and an alpha 2,3-sialyltransferase, which can be coupled with (viii) producing the CMP-Neu5Ac from Neu5Ac in the presence of the set of CMP-Neu5Ac regeneration enzymes described herein. Steps (vii) and (viii) can occur in a Sialyl-Gb5-synthesis reaction mixture comprising Neu5Ac, CTP, PEP, the Gb5-OR$^{1-4}$, the alpha 2,3-sialyltransferase, and the set of CMP-Neu5Ac regeneration enzymes. In some instances, the Sialyl-Gb5-synthesis reaction mixture is prepared by mixing the Gb5-synthesis reaction mixture with at least Neu5Ac, CTP, the alpha 2,3-sialyltransferase, the cytidine monophosphate kinase, and the CMP-sialic acid synthetase. The resultant Sialyl-Gb5-OR$^{1-4}$ can be isolated from the reaction mixture.

In yet other embodiments, the methods described herein relate to synthesizing oligosaccharides, using Gb4 (e.g., tailed) as a starting material. Such a method comprises: (i) producing UDP-Gal from galactose in the presence of the set of UDP-Gal regeneration enzymes described herein, and (ii) converting Gb4-OR$^{1-4}$ into Gb5-OR$^{1-4}$ in the presence of UDP-Gal and a beta1,3-galactosyltransferase, wherein R$^{1-4}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group. Examples of R$^{1-4}$ include, but are not limited, to hydrogen, allyl, biotin, a ceramide, or a non-hydrogen group (e.g., alkyl) which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, R$^{1-4}$ is hydrogen, allyl, substituted alkyl, biotin, or a ceramide. In this method, steps (i) and (ii) can occur in a Gb5-synthesis reaction mixture comprising galactose, PEP, ATP, UTP, the Gb4-OR$^{1-4}$, the beta1,3-galactosyltransferase, and the set of UDP-Gal regeneration enzymes. Alternatively or in addition, the Gb5-OR$^{1-4}$ thus produced can be isolated.

The above method can further comprise: (iii) converting the Gb5-OR$^{1-4}$ into Fucosyl-Gb5-OR$^{1-4}$ in the presence of GDP-Fuc and an alpha1,2-fucosyltransferase, which can be coupled with (iv) producing the GDP-Fuc from fucose in the presence of the set of GDP-Fuc regeneration enzymes, which is also described herein. Steps (iii) and (iv) can take place in a Fucosyl-Gb5-synthesis reaction mixture comprising fucose, ATP, GTP, PEP, the Gb5-OR$^{1-4}$, the alpha1,2-fucosyltransferase, and the set of GDP-Fuc regeneration enzymes. The Fucosyl-Gb5-synthesis reaction mixture is prepared by mixing the Gb5-synthesis reaction mixture with at least fucose, GTP, the alpha1,2-fucosyltransferase, and the L-fucokinase/GDP-fucose pyrophosphorylase. The resultant Fucosyl-Gb5-OR$^{1-4}$ can be isolated from the reaction mixture.

Alternatively, the above method can further comprise: (v) converting the Gb5-OR$^{1-4}$ into Sialyl-Gb5-OR$^{1-4}$ in the presence of CMP-Neu5Ac and an alpha 2,3-sialyltransferase, which can be coupled with (v) producing the CMP-Neu5Ac from Neu5Ac in the presence of the set of CMP-Neu5Ac regeneration enzymes described herein. Steps (v) and (vi) can occur in a Sialyl-Gb5-synthesis reaction mixture comprising Neu5Ac, CTP, PEP, the Gb5-OR$^{1-4}$, the alpha 2,3-sialyltransferase, and the set of CMP-Neu5Ac regeneration enzymes. The Sialyl-Gb5-synthesis reaction mixture is prepared by mixing the Gb5-synthesis reaction mixture with at least Neu5Ac, CTP, the alpha 2,3-sialyltransferase, the cytidine monophosphate kinase, and the CMP-sialic acid synthetase. The Sialyl-Gb5-OR$^{1-4}$ produced in this method can be isolated from the reaction mixture.

In some other embodiments, the methods described herein relate to synthesis of a Fucosyl-Gb5 oligosaccharide (Globo H) from Gb5. The method comprising: (i) producing GDP-Fuc from fucose in the presence of the set of GDP-Fuc regeneration enzymes described herein, (ii) converting Gb5-OR$^{1-4}$ into Fucosyl-Gb5-OR$^{1-4}$ in the presence of the GDP-Fuc and an alpha1,2-fucosyltransferase, and, optionally, (iii) isolating the Fucosyl-Gb5-OR$^{1-4}$. Steps (i) and (ii) can occur in a Fucosyl-Gb5-synthesis reaction mixture comprising fucose, ATP, GTP, PEP, the Gb5-OR$^{1-4}$, the alpha1,2-fucosyltransferase, and the set of GDP-Fuc regeneration enzymes.

In some other embodiments, the methods described herein relate to synthesis of a Sialyl-Gb5 oligosaccharide (Globo H) from Gb5. The method comprises: (i) producing CMP-Neu5Ac from Neu5Ac in the presence of the set of CMP-Neu5Ac regeneration enzymes described herein, (ii) converting Gb5-OR$^{1-4}$ into Sialyl-Gb5-OR$^{1-4}$ in the presence of CMP-Neu5Ac and an alpha 2,3-sialyltransferase, and, optionally, (iii) isolating the Sialyl-Gb5-OR$^{1-4}$. Steps (i) and (ii) can take place in a Sialyl-Gb5-synthesis reaction mixture comprising Neu5Ac, CTP, PEP, the Gb5-OR, the alpha 2,3-sialyltransferase, and the set of CMP-Neu5Ac regeneration enzymes.

In any of the synthesis methods described herein, either at least one of the involved enzymes or at least one of the substrates of each reaction (e.g., lactose, Gb3, Gb4, or Gb5) can be immobilized on a support member.

Another aspect of the present disclosure features enzymatic reactors for synthesizing oligosaccharides using the methods described herein. Such an enzymatic reactor can comprise one or more of the following reaction chambers:

(a) a reaction chamber for synthesizing Gb3-OR$^{1-4}$, wherein the chamber comprises an alpha1,4-galactosyltransferase, and a set of UDP-Gal regeneration enzymes, which comprises a galactokinase, a UDP-sugar pyrophosphorylase, a pyruvate kinase, and optionally a pyrophosphatase;

(b) a reaction chamber for synthesizing Gb4-OR$^{1-4}$, wherein the chamber comprises a beta1,3-N-acetylgalactosaminyltransferase and a set of UDP-GalNAc regeneration enzymes, which comprises an N-acetylhexosamine 1-kinase, an N-acetylglucosamine 1-phosphate uridylyltransferase, a pyruvate kinase, and optionally a pyrophosphatase;

(c) a reaction chamber for synthesizing Gb5-OR$^{1-4}$, wherein the chamber comprises a beta1,3-galactosyltransferase, and the set of UDP-Gal regeneration enzymes;

(d) a reaction chamber for synthesizing Fucosyl-Gb5-OR$^{1-4}$, wherein the chamber comprises an alpha1,2-fucosyltransferase and a set of GDP-Fuc regeneration enzymes, which comprises an L-fucokinase/GDP-fucose pyrophosphorylase, a pyruvate kinase, and optionally a pyrophosphatase; and (e) a reaction chamber for synthesizing Sialyl-Gb5-OR$^{1-4}$, wherein the chamber comprises an alpha2,3-sialyltransferase and a set of CMP-Neu5Ac regeneration enzymes, which comprises a cytidine monophosphate kinase, a CMP-sialic acid synthetase, a pyruvate kinase, and optionally a pyrophosphatase.

In some examples, the enzymatic reactor comprises reaction chambers: (a) and (b); (a), (b), and (c); (a), (b), (c), and (d); (a), (b), (c), and (e); (b) and (c); (b), (c), and (d); (b), (c), and (e); (c) and (d); or (c) and (e).

In another example, the enzymatic reactor described herein comprises a reaction chamber that comprises a galactosyltransferase (e.g., an alpha1,4-galactosyltransferase, a beta1,4-galactosyltransferase, an alpha1,3-galactosyltransferase, or a beta1,3-galactosyltransferase) and a set of UDP-Gal regeneration enzymes as described herein, which may comprise a galactokinase, an UDP pyrophosphorylase, a pyruvate kinase, and optionally a pyrophosphatase.

In any of the reaction chambers, one or more of the enzymes can be immobilized on a support member. In some examples, one or more of the set of UDP-Gal regeneration enzymes, the set of UDP-GalNAc regeneration enzymes, the set of GDP-Fuc regeneration enzymes, and the set of CMP-Neu5Ac regeneration enzymes are each immobilized on a support member. In other examples, all of the enzymes in a reaction chamber are immobilized on a support member.

Also within the scope of the present disclosure are oligosaccharides obtained from any of the synthesis methods described herein.

The details of one or more embodiments of the invention are set forth in the Detailed Description of Certain Embodiments, as described below. Other features, objects, and advantages of the invention will be apparent from the Definitions, Drawings, Examples, and Claims.

CHEMICAL DEFINITIONS

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

As used herein, "alkenyl" or "alkene" refers to a radical of a straight-chain or branched hydrocarbon group having from 2 to 30 carbon atoms and one or more double bonds (e.g., 1, 2, 3, or 4 double bonds). In some embodiments, an alkenyl group has 2 to 20 carbon atoms ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ("allyl", $C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" or "alkyne" refers to a radical of a straight-chain or branched hydrocarbon group having from 2 to 30 carbon atoms and one or more triple bonds (e.g., 1, 2, 3, or 4 triple bonds) ("$C_{2-10}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

As used herein, "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Alkyl, alkenyl, alkynyl, heteroalkyl, heteroalkenyl, heteroalkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=S)R$^{aa}$, —OC(=S)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$—CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-5}$ alkyl)$_2^+X^-$, —$NH_2$($C_{1-6}$ alkyl) $^+X^-$, —$NH_3^+X^-$, —N(O$C_{1-6}$ alkyl)($C_{1-6}$ alkyl), —N(OH)($C_{1-6}$ alkyl), —NH(OH), —SH, —$SC_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —$OCO_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —$NHCO_2$($C_{1-5}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)$NH_2$, —OC(=NH)N($C_{1-6}$ alkyl)$_2$, —OC(NH)NH($C_{1-5}$ alkyl), —OC(NH)$NH_2$, —NHC(NH)N($C_{1-6}$ alkyl)$_2$, —NHC(=NH)$NH_2$, —$NHSO_2$ ($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)$NH_2$, —C(=O)S($C_{1-6}$ alkyl), —C(=S)$SC_{1-6}$ alkyl, —SC(=S)$SC_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{1-6}$ heteroalkyl, $C_{2-6}$ heteroalkenyl, $C_{2-6}$ heteroalkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "carbonyl" refers a group wherein the carbon directly attached to the parent molecule is $sp^2$ hybridized, and is substituted with an oxygen, nitrogen or sulfur atom, e.g., a group selected from ketones (—C(=O)$R^{aa}$), carboxylic acids (—$CO_2H$), aldehydes (—CHO), esters (—$CO_2R^{aa}$, —C(=O)$SR^{aa}$, —C(=S)$SR^{aa}$), amides (—C(=O)N($R^{bb}$)$_2$, —C(=O)N$R^{bb}SO_2R^{aa}$, —C(=S)N($R^{bb}$)$_2$), and imines (—C(=N$R^{bb}$)$R^{aa}$, —C(=N$R^{bb}$) O$R^{aa}$), —C(=N$R^{bb}$)N($R^{bb}$)$_2$), wherein $R^{aa}$ and $R^{bb}$ are as defined herein.

As used herein, "azide" or "azido" refers to the group —$N_3$.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —$SR^{aa}$, —S=$SR^{cc}$, —SC(=S)$SR^{aa}$, —SC(=O)$SR^{aa}$, —SC(=O)$OR^{aa}$, and —SC(=O)$R^{aa}$, wherein $R^{aa}$ and $R^{cc}$ are as defined herein.

As used herein, the term, "amino" or "amine" refers to the group —$NH_2$. The term "substituted" amino or amine, by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" or "monosubstituted amine" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —$NHCO_2R^{aa}$, —NHC(=O)N($R^{bb}$)$_2$, —NHC(=N$R^{bb}$)N($R^{bb}$)$_2$, —$NHSO_2R^{aa}$, —NHP(=O)(O$R^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group —NH($R^{bb}$) is not hydrogen.

As used herein, the term "disubstituted amino" or "disubstituted amine" refers to an amino group wherein the nitrogen atom directly attached to the parent molecule is substituted with two groups other than hydrogen, and includes groups selected from —N($R^{bb}$)$_2$, —$NR^{bb}C$(=O)$R^{aa}$, —$NR^{bb}CO_2R^{aa}$, —$NR^{bb}C$(=O)N($R^{bb}$)$_2$, —$NR^{bb}C$(=$NR^{bb}$)N($R^{bb}$)$_2$, —$NR^{bb}SO_2R^{aa}$, —$NR^{bb}P$(=O)(O$R^{cc}$)$_2$, and —$NR^{bb}P$(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" or "trisubstituted amine" refers to an amino group wherein the nitrogen atom directly attached to the parent molecule is substituted with three groups, and includes groups selected from —N($R^{bb}$)$_3$ and —N($R^{bb}$)$_3^+X^-$, wherein $R^{bb}$ and $X^-$ are as defined herein.

As used herein, "biotin", e.g., as an exemplary $R^{L4}$ group, comprises the structure:

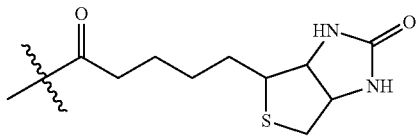 [SMILES: *C(=O)CCCCC1SCC2NC(=O)NC21]

As used herein, a "ceramide", e.g., as an exemplary $R^{L4}$ group, comprises the structure:

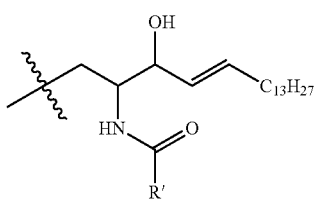

wherein R' is an optionally substituted $C_6$-$C_{30}$ alkyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$ alkyl), optionally substituted $C_6$-$C_{30}$alkenyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$ alkenyl), or optionally substituted $C_6$-$C_{30}$alkynyl (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or $C_{30}$ alkynyl) group.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR")OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{1-10}$ heteroalkyl, $C_{2-10}$ heteroalkenyl, $C_{2-10}$ heteroalkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$, are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(phydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1 isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, $CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio)ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

These and other exemplary substituents are described in more detail in the Detailed Description, Examples, and claims. The invention is not intended to be limited in any manner by the above exemplary listing of substituents.

As used herein, the term "salt" refers to any and all salts.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

DETAILED DESCRIPTION OF THE INVENTION

Figure 1:
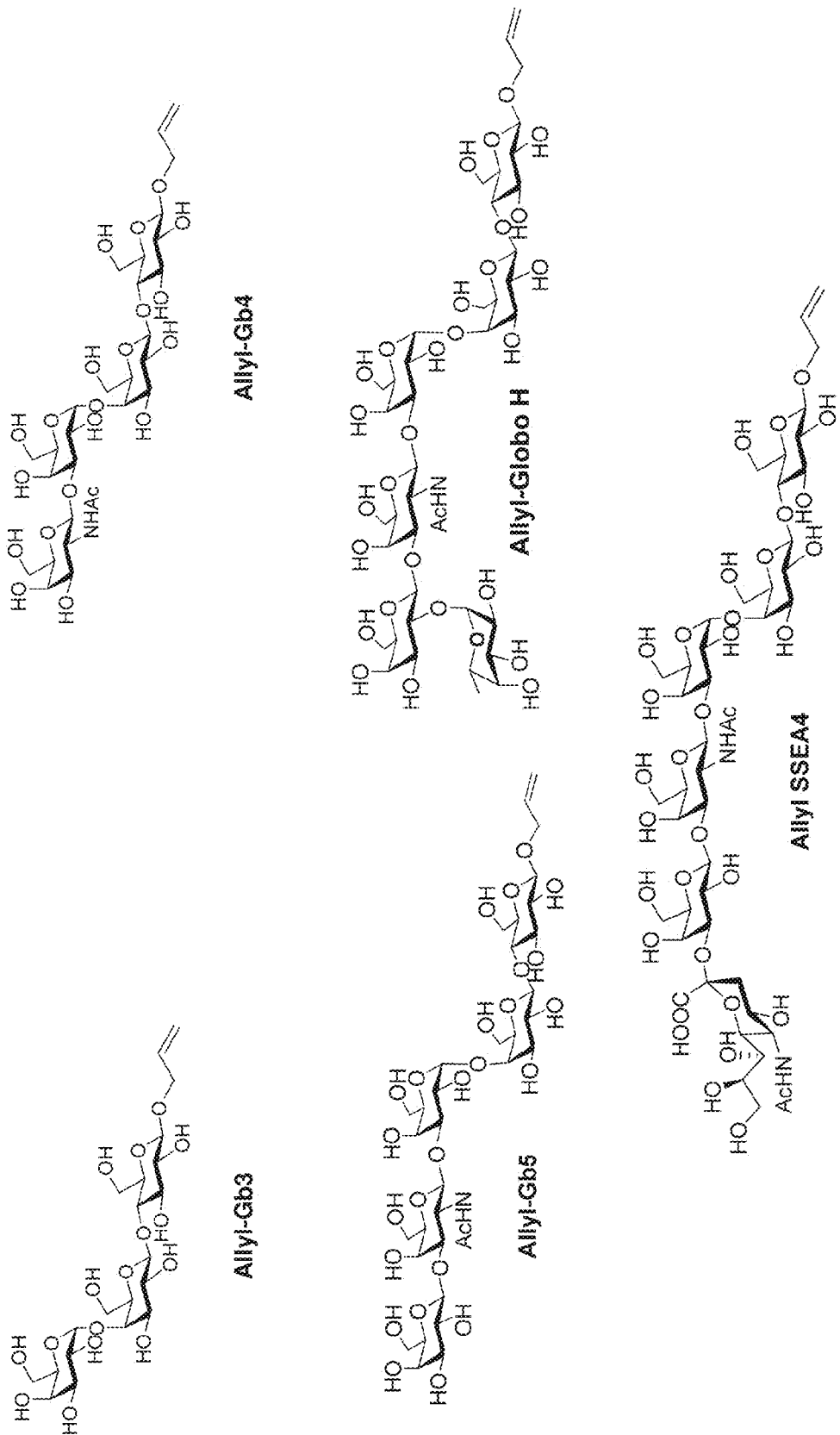
FIG. 1 depicts the chemical structures of allyl-tailed Gb3, Gb4, Gb5, Globo H, and SSEA4.

Described herein are newly developed nucleotide sugar regeneration processes and their uses in adding sugar residues to suitable acceptors via the action of a suitable glycosyltransferase. These approaches allow chain reactions for synthesizing glycosylated molecules, such as oligosaccharides (e.g., Gb3, Gb4, Gb5, Globo H, and SSEA4) without the need to purify intermediates, resulting in unexpectedly rapid production of the glycosylated products with unexpectedly high yields. In addition, the synthesis methods described herein can be used for large scale production of desired oligosaccharides and glycoconjugates.

UDP-Gal Regeneration System and its Use in Galactosylation

The UDP-Gal regeneration system is exemplified in FIG. 2A, involving the enzymes listed in Table 1 below:

TABLE 1

Enzymes Used in UDP-Gal Regeneration System

| Enzyme | Activity | Examples |
| --- | --- | --- |
| Galactokinase (GalK) | Catalyzes the phosphorylation of alpha-D-galactose to produce galactose-1-phosphate (Gal-1-P) in the presence of ATP | *E. coli* (e.g., GenBank accession no. AP012306.1) *H. sapiens* (e.g., GenBank accession no. NP_000145) *M. hydrothermalis* (e.g., GenBank accession no. YP_004368991) *S. sputigena* (e.g., GenBank accession no. AEC00832) *H. hydrossis* (e.g., GenBank accession no. YP_004451189) |

TABLE 1-continued

Enzymes Used in UDP-Gal Regeneration System

| Enzyme | Activity | Examples |
| --- | --- | --- |
| UDP-sugar pyrophosphorylase (USP) | Catalyzes the conversion of Gal-1-P to UDP-Gal in the presence of UTP | A. thaliana (e.g., GenBank accession no. AF360236.1<br>L. major (e.g., GenBank accession no. ABY79093)<br>T. cruzi (e.g., GenBank accession no. ADD10758)<br>L. donovani (e.g., GenBank accession no. XP_00385998)<br>G. max (e.g., GenBank accession no. NP_001237434) |
| Pyruvate kinase (PykF) | Catalyzes the transfer of a phosphate group from phosphoenolpyruvate (PEP) to ADP, producing pyruvate and ATP or UTP | E. coli (e.g., GenBank accession no. U00096.2)<br>N. hamburgensis (e.g., GenBank accession no. YP_576506)<br>R. palustris (e.g., GenBank accession no. YP_7830161)<br>M. ruestringensis (e.g., GenBank accession no. YP_004787669)<br>H. hydrossis (e.g., GenBank accession no. YP_004450514)<br>S. coccoides (e.g., GenBank accession no. YP_00441096) |
| Pyrophosphatase (PPA) (Optional) | Acid anhydride hydrolase that acts upon diphosphate bonds | E. coli (e.g., GenBank accession no. U00096.2<br>G. theta (e.g., GenBank accession no. CAI77906)<br>C. butyricum (e.g., GenBank accession no. ZP_04525837)<br>L. plantarum (e.g., GenBank accession no. EFK28054)<br>L. suebicus (e.g., GenBan accession no. ZP_09451344) |

The enzymes to be used in the UDP-Gal regeneration system described herein can be a wild-type enzyme. As used herein, a wild-type enzyme is a naturally occurring enzyme found in a suitable species. In some examples, the GalK, USP, PykF, and PPA enzymes can be from E. coli, A. thaliana, E. coli, and E. coli, respectively. Examples of the enzymes from these species are listed in Table 1 above. Others can be readily identified by those skilled in the art, e.g., search a publicly available gene database, such as GenBank. In other examples, these enzymes are homologs of those from the just-noted species, which are within the knowledge of those skilled in the art. For example, such homologs can be identified by searching GenBank using the amino acid sequence or the coding nucleotide sequence of an exemplary enzyme as a search query.

Alternatively, the enzymes involved in the UDP-Gal regeneration system can be a functional variant of a wild-type counterpart. As used herein, a functional variant of a wild-type enzyme possesses the same enzymatic activity as the wild-part counterpart and typically shares a high amino acid sequence homology, e.g., at least 80%, 85%, 90%, 95, or 98% identical to the amino acid sequence of the wild-type counterpart. The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

A functional variant can have various mutations, including addition, deletion, or substitution of one or more amino acid residues. Such a variant often contain mutations in regions that are not essential to the enzymatic activity of the wild-type enzyme and may contain no mutations in functional domains or contain only conservative amino acid substitutions. The skilled artisan will realize that conservative amino acid substitutions may be made in lipoic acid ligase mutants to provide functionally equivalent variants, i.e., the variants retain the functional capabilities of the particular lipoic acid ligase mutant. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Any of the enzymes involved in the UDP-Gal regeneration system can be prepared via routine technology. In one example, the enzyme is isolated form a natural source. In other examples, the enzyme is prepared by routine recombinant technology. When necessary, the coding sequence of a target enzyme can be subjected to coden optimization based on the host cell used for producing the enzyme. For example, when *E. coli* cells are used as the host for producing an enzyme via recombinant technology, the gene encoding that enzyme can be modified such that it contains codons commonly used in *E. coli*.

Figure 2:
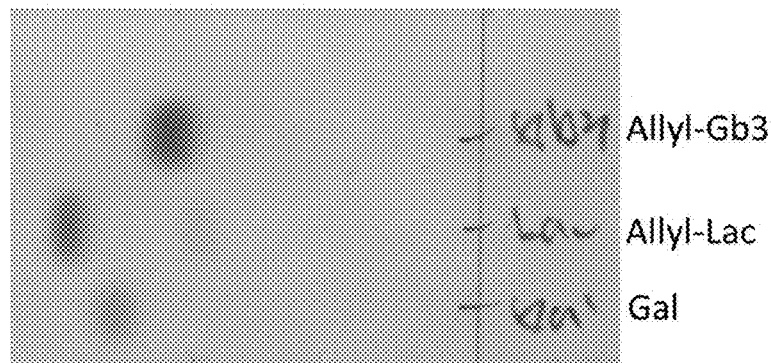
FIG. 2 depicts glycosylation reactions combined with nucleotide sugar regeneration and synthesis results monitored by TLC. A: Combined galactosylation with UDP-Gal regeneration for synthesizing, e.g., allyl-Gb3. B: Combined acetylgalactosamination with UDP-GalNAc regeneration for synthesizing, e.g., allyl-Gb4. C: Combined galactosylation with UDP-Gal regeneration for synthesizing, e.g., allyl-Gb5. D: Combined fucosylation with GDP-Fuc regeneration for synthesizing, e.g., allyl-Globo H. E: Combined sialylation with CMP-Neu5Ac regeneration for synthesizing, e.g., allyl-SSEA4.
Figure 2:
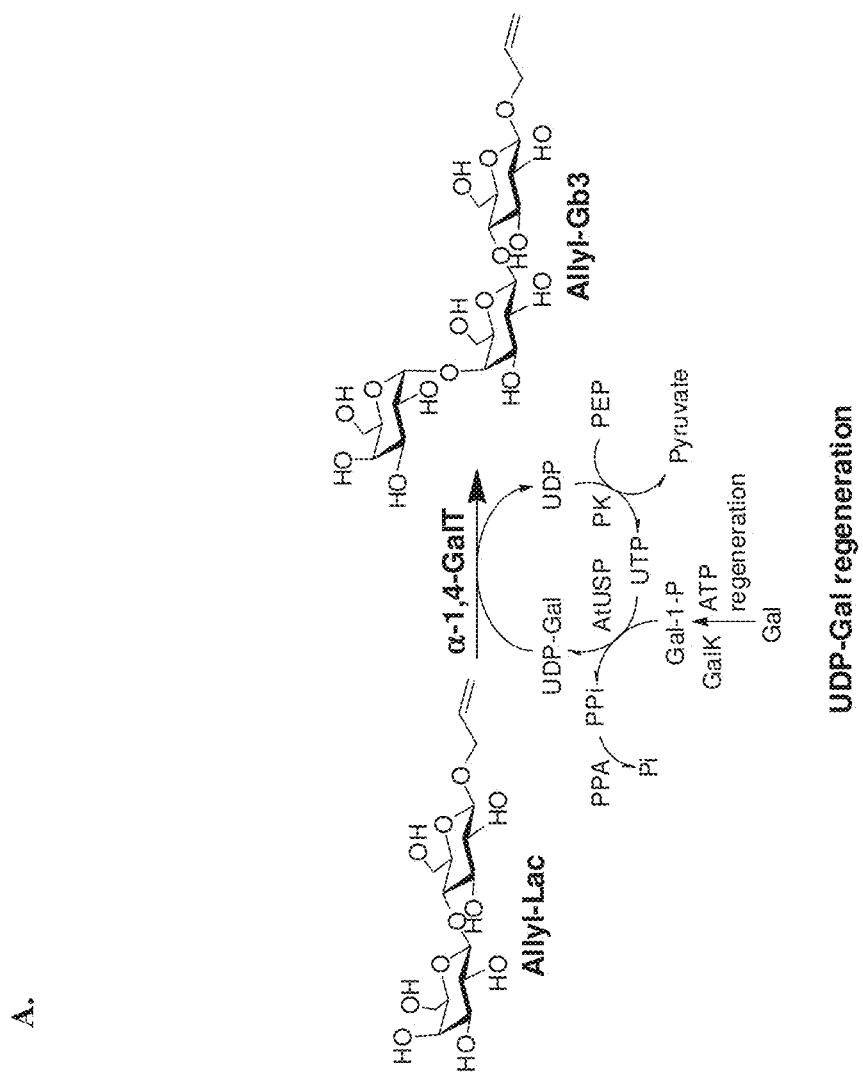
Figure 2:
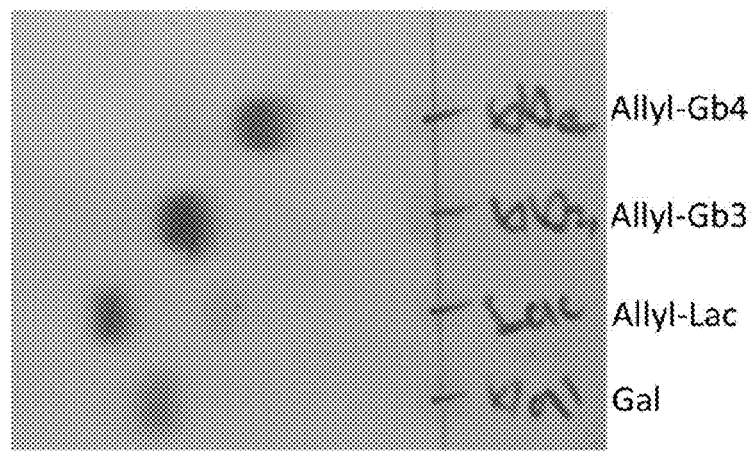
Figure 2:
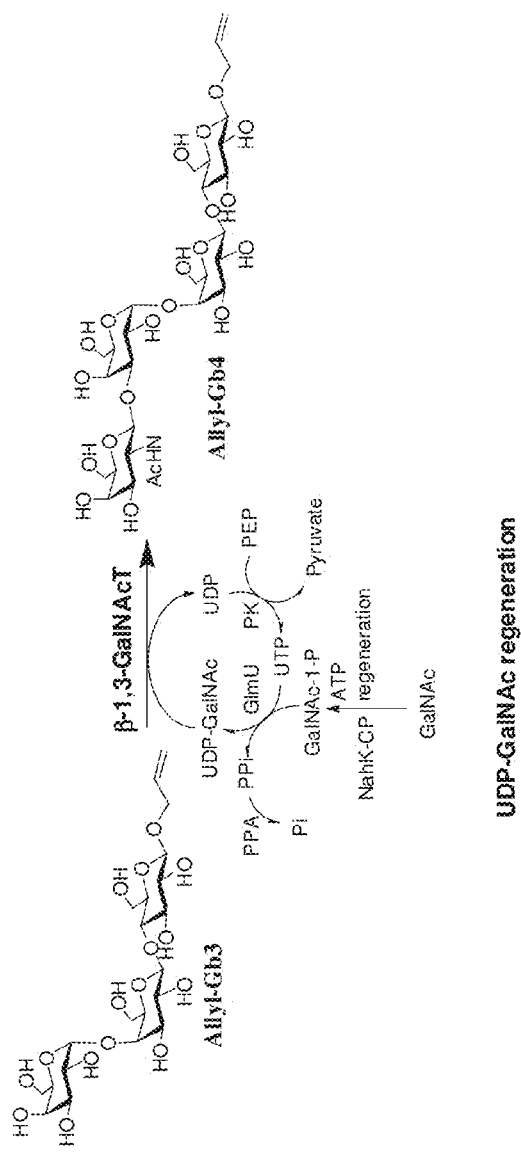
Figure 2:
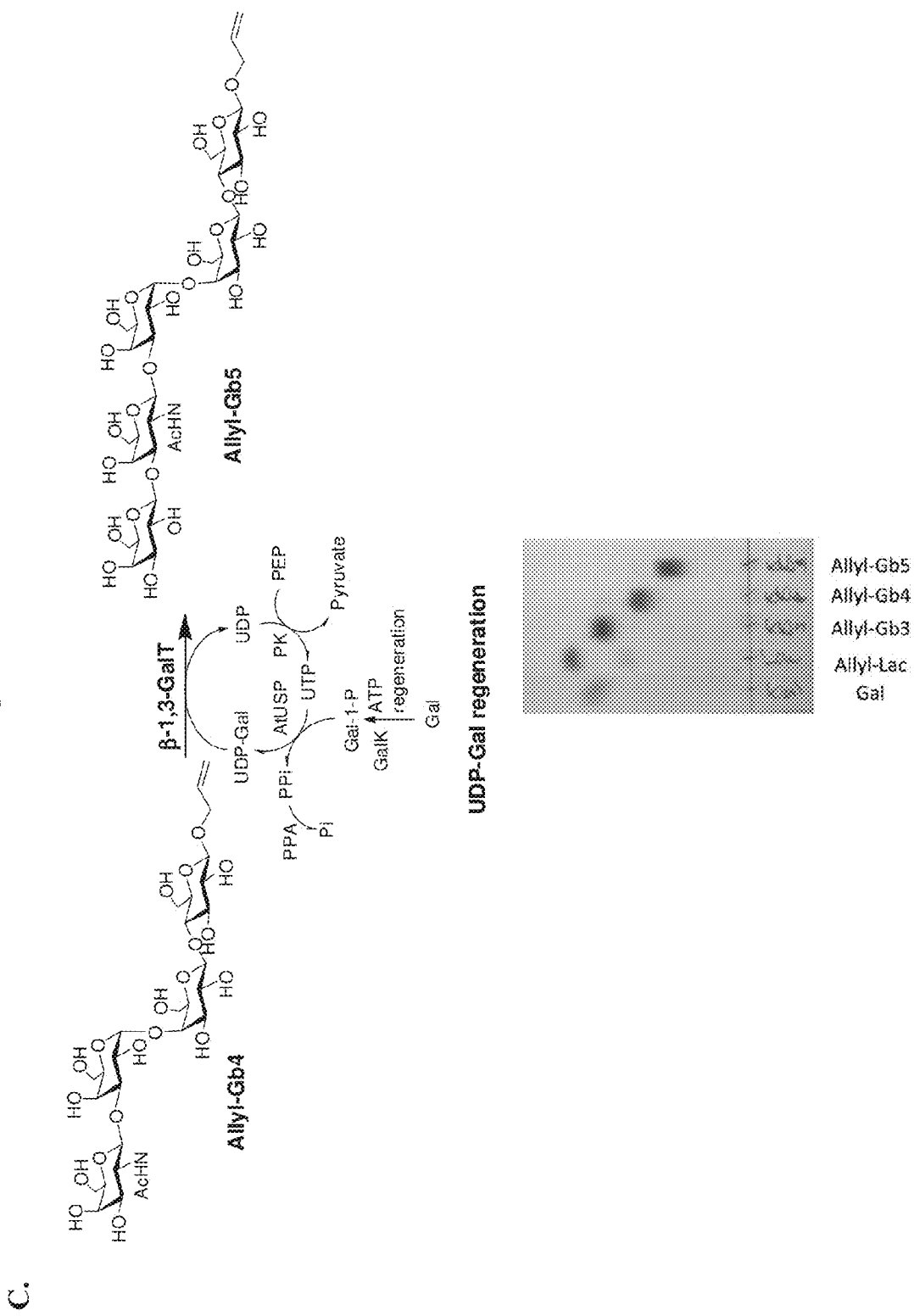
Figure 2:
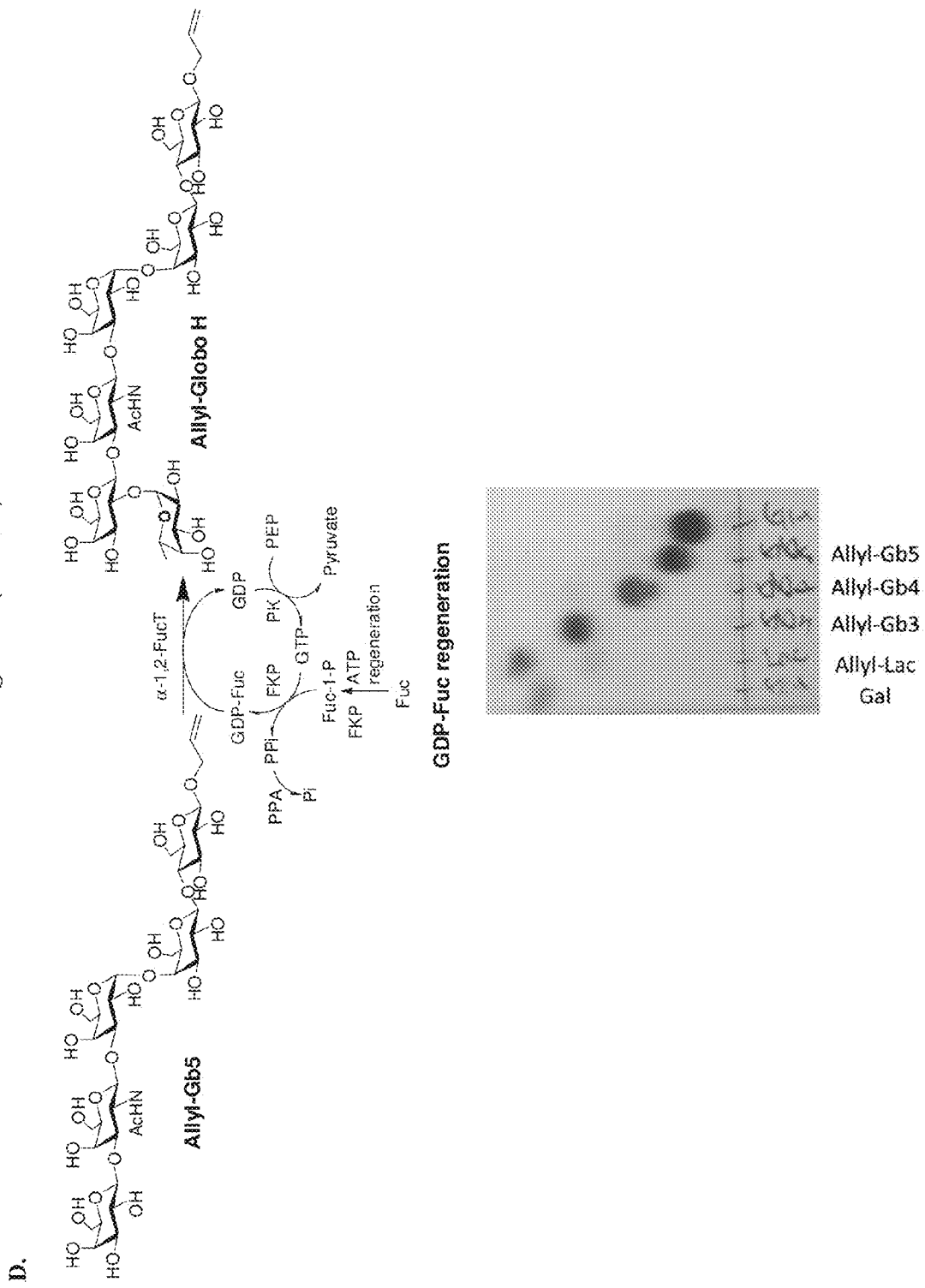
Figure 2:
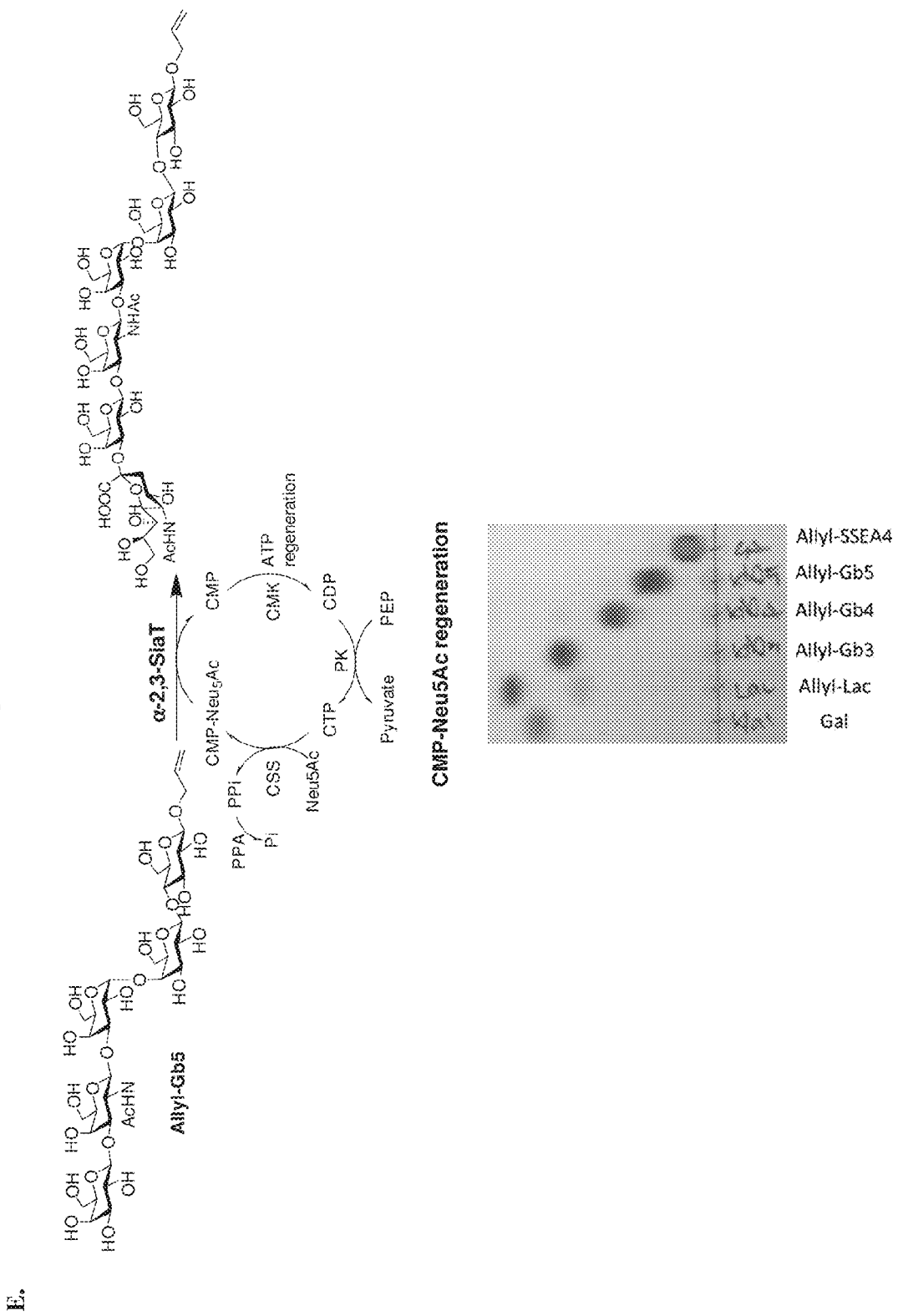
Figure 3:
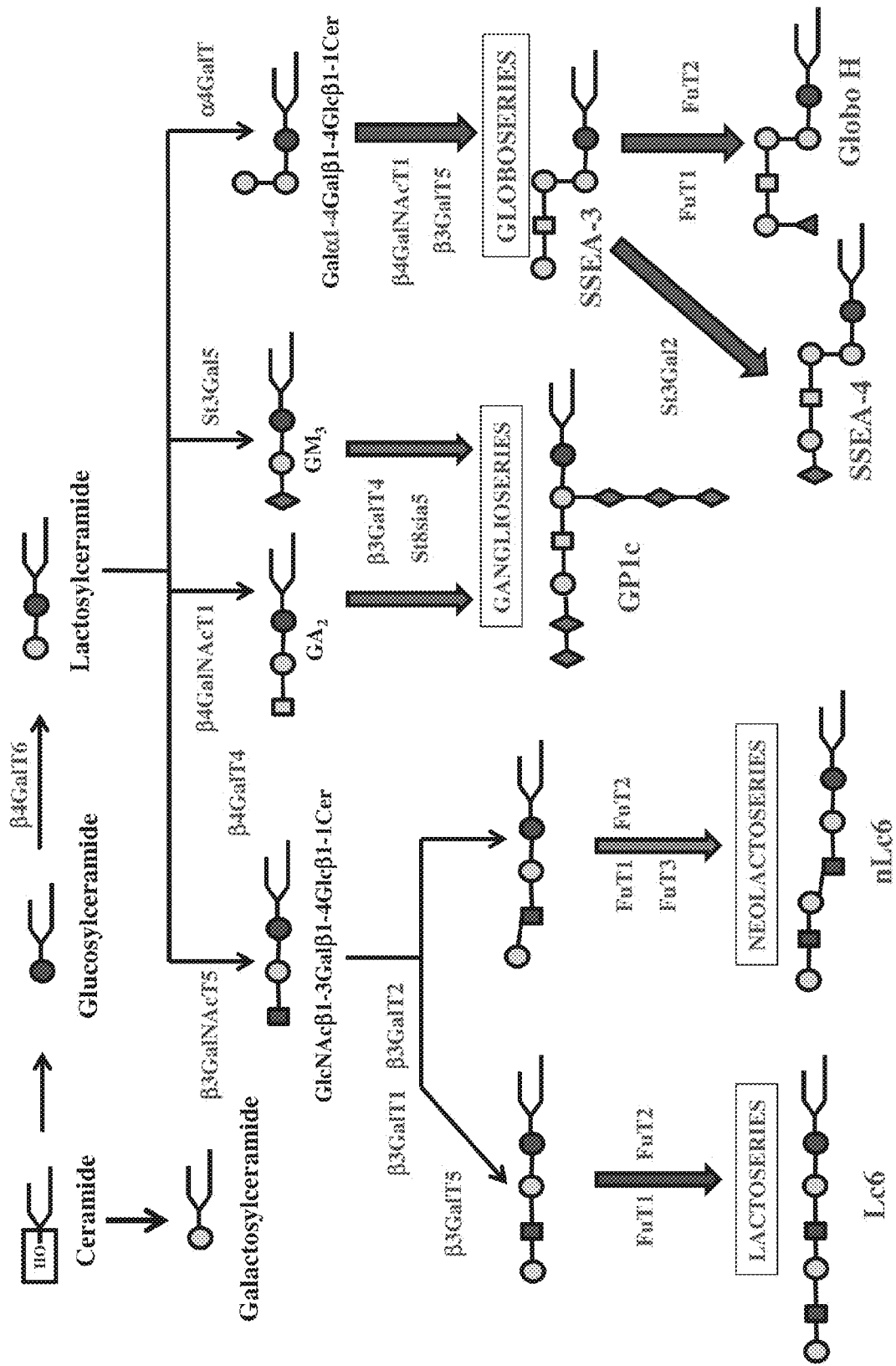
FIG. 3 depicts the biosynthetic pathway of glycosphingolipids, involving addition of galactose residues, which can be catayzed by a galactosyltranferase coupled with the UDP-Gal regeneration process described herein.
Figure 4:
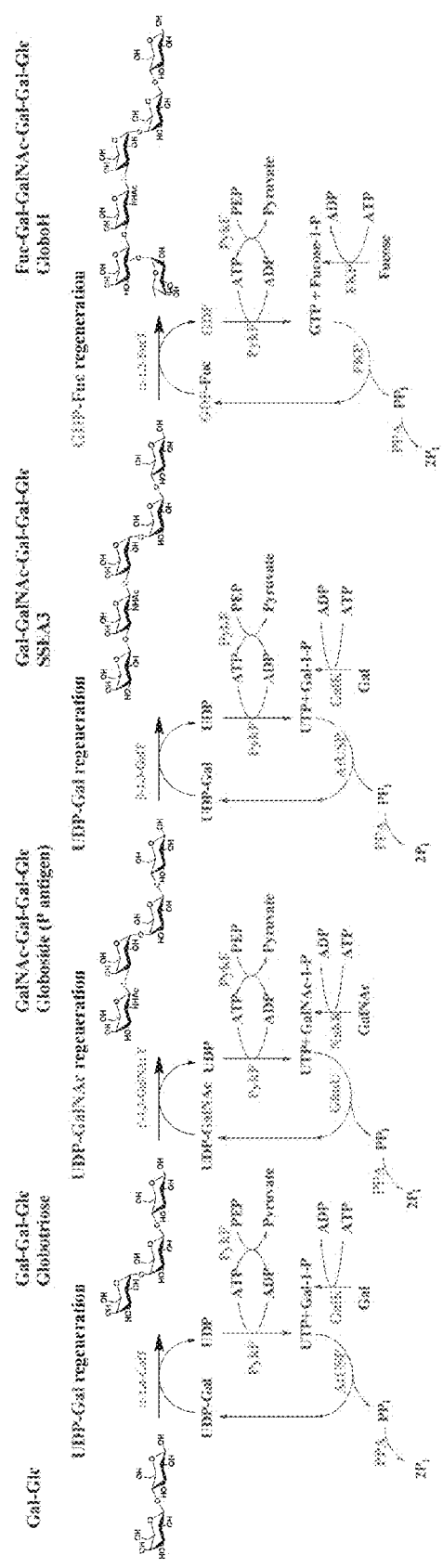
FIG. 4 depicts the enzymatic synthetic strategy in the manufacture of Globo H via the Lac→Gb3→Gb4→Gb5 pathway using a nucleotide sugar regeneration system.
Figure 5:
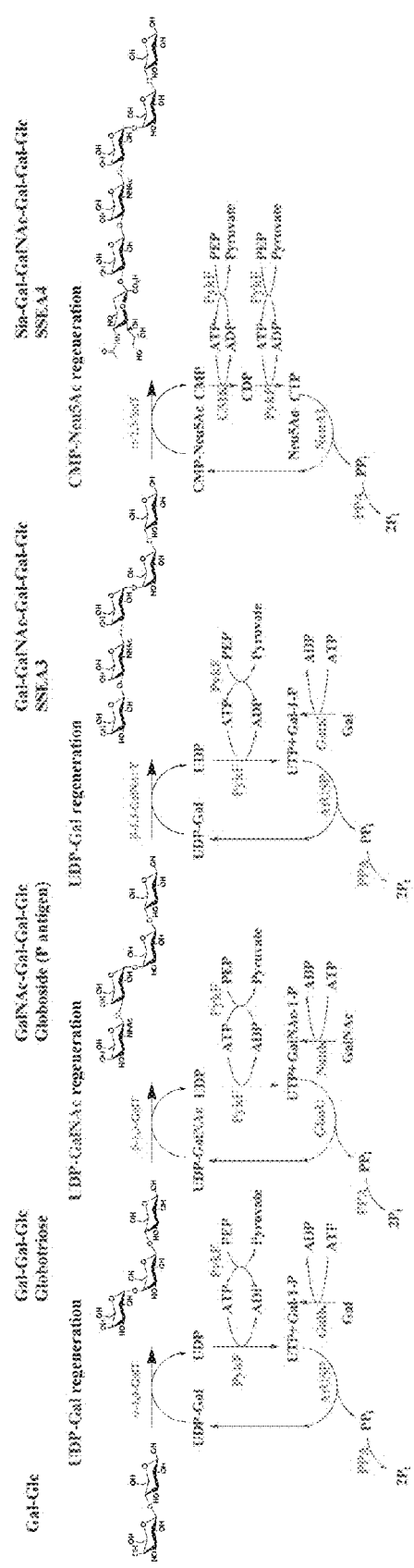
FIG. 5 depicts the enzymatic synthetic strategy in the manufacture of SSEA4 via the Lac→Gb3→Gb4→Gb5 pathway using a nucleotide sugar regeneration system.

As illustrated in FIG. 2A, the UDP-Gal regeneration system can be used in conjunction with a galactosylation reaction via the activity of a galactosyltransferase to add a galactose residue to a suitable substrate. Examples of galactosyltransferases are listed in Table 2 below:

described in Table 2 above, are well known to those skilled in the art. Preferably, the substrate has a terminal sugar residue (e.g., Gal, GalNAc, or GlcNAc) to which the galactose residue can be added. In some examples, the substrate is a polysaccharide (having >50 monosaccharide units), an oligosaccharide (having 2-50 monosaccharide units), a glycoprotein or glycopeptide, or a glycolipid. The type of a galactosyltransferase to be used in the galactosylation methods descried herein depends on the end product of interest and the substrate for synthesizing the end product, which is well within the knowledge of a skilled artisan. The combined UDP-Gal regeneration system/galactosyltransferase approach described herein can be used to synthesize glycosphingolipids. Examples are illustrated in FIG. 3.

In other examples, the combined UDP-Gal generation system/galactosyltranferase approach can be used for synthesizing Globo-series oligosaccharides, such as synthesis of Gb3 from lactose or synthesis of Gb5 from Gb4. FIGS. 2A and 2C. See also descriptions below.

TABLE 2

| Galactosyltransferases | | |
|---|---|---|
| Galactosyltransferase | Enzymatic Activity | Examples |
| Beta-1,4-Galactosyltransferase (B4GALT), including isoforms 1-7 (Beta-1,4-galactosyltransferase 1-7) | Catalyzes the transfer of galactose from UDP-Gal to a suitable acceptor, such as a glycoprotein or glycolipid acceptor having a terminal 2-acetamido-2-deoxy-D-glucosyl-group, in an beta1,4-linkage | *Homo sapiens* [e.g., GI: 903740]<br>*Rattus norvegicus* [e.g., GI: 3258653]<br>*Zobellia galactanivorans* [e.g., GI: 340619721]<br>*Clostridium perfringens* [e.g., GI: 18309463] |
| Beta-1,3-Galactosyltransferase (B3GALNT) | Catalyzes the transfer of galactose from UDP-Gal to a suitable acceptor, such as a glycoprotein or glycolipid acceptor having a terminal 2-acetamido-2-deoxy-D-glucosyl-group, or a GalNAc residue, in an beta1,3-linkage | *Culex quinquefasciatus* [e.g., GI: 167873909]<br>*Zea mays* [e.g., GI: 195643406]<br>*Brachyspira pilosicoli* [e.g., GI: 300871377]<br>*Enterococcus faecium* [e.g., GI: 257822935]<br>LgtD, from, e.g., *Haemophilus influenza* [L42023.1] |
| Alpha-1,4-Galactosyltransferase (A4GALT) e.g.: Lactosylceramide 4-alpha-galactosyltransferase | Catalyzes the transfer of a galactose from UDP-Gal to a suitable acceptor such as a glycoprotein or a glycolipid having, e.g., a terminal galactose residue or a GlcNAc residue in an alpha 1,4-linkage | *Homo sapiens* [e.g., GI: 55956926]<br>*Mustela putorius furo* [e.g., GI: 355666115]<br>*Mus musculus* [e.g., GI: 51921295]<br>*Rattus norvegicus* [e.g., GI: 67677925]<br>LgtC from, e.g., *Neisseria meningitides* [e.g., AF355193.1] |
| Alpha-1,3-Galactosyltransferase (A3GALT) e.g.: Alpha-1,3-Galactosyltransferase 1 Alpha-1,3-Galactosyltransferase 2 | Catalyzes the transfer of a galactose from UDP-Gal to a suitable acceptor such as a glycoprotein or a glycolipid having, e.g., a terminal galactose residue or a GlcNAc residue in an alpha 1,3-linkage | *Mus musculus* [e.g., GI: 224922807]<br>*Mustela putorius faro* [e.g., GI: 355690122]<br>*Cebus paella* [e.g., GI: 19698748]<br>*Rattus norvegicus* [e.g., GI: 28625949] |

Both wild-type galactosyltransferases and functional variants, as described above, are within the scope of this description. Such glycosyltransferases can be prepared via any routine method.

The combination of the UDP-Gal regeneration system and one or more galactosyltransferases can be used for adding a galactose residue to a suitable substrate (an acceptor) with high yields. Substrates for galactosyltransferase, e.g., UDP-GalNAc Regeneration System and its Use in N-Acetylgalactosamination A UDP-GalNAc regeneration system can be co-used with an N-acetylgalactosaminyltransferase (GalNAcT), such as a beta1,3-N-acetylgalactosaminyltransferase, for addition of a GalNAc residue onto a suitable acceptor.

Enzymes involved in an exemplary UDP-GalNAc regeneration system are shown in Table 3 below:

TABLE 3

Enzymes Used in UDP-GalNAc Regeneration System

| Enzyme | Activity | Examples |
| --- | --- | --- |
| N-Acetylhexosamine 1-Kinase (GalNAcK) | Acts by a sequential two substrates-two products mechanism to convert ATP and N-acetylhexosamine into ADP and N-acetyl-alpha-D-hexosamine 1-phosphate. | NahK from *B. longum* (e.g., GenBank accession no. CP000246.1 *B. breve* (e.g., GenBank accession no. ZP_06596651) *A. haemolyticum* (e.g., GenBank accession no. YP_003696399 *B. bifidum* (e.g., GenBank accession no. YP_003938776) |
| N-acetylglucosamine 1-phosphate uridylyltransferase (GlmU) | Catalyzes the conversion of UTP and N-acetyl-alpha-D-glucosamine 1-phosphate into diphosphate and UDP-N-acetyl-D-glucosamine | GlmU from *E. coli* (e.g., GenBank accession no. U00096.2 *A. thaliana* (e.g., GenBank accession no. AEE31311) *G. bemidjiensis* (e.g., GenBank accession no. ACH37122) *H. pylori* (e.g., GenBank accession no. YP_003728906) |
| Pyruvate kinase (PykF) | Catalyzes the transfer of a phosphate group from phosphoenolpyruvate (PEP) to ADP, producing pyruvate and ATP or UTP | *E. coli* (e.g., GenBank accession no. U00096.2) *N. hamburgensis* (e.g., GenBank accession no. YP_576506) *R. palustris* (e.g., GenBank accession no. YP_7830161) *M. ruestringensis* (e.g., GenBank accession no. YP_004787669) *H. hydrossis* (e.g., GenBank accession no. YP_004450514) *S. coccoides* (e.g., GenBank accession no. YP_00441096) |
| Pyrophosphatase (PPA) (Optional) | Acid anhydride hydrolase that acts upon diphosphate bonds | *E. coli* (e.g., GenBank accession no. U00096.2 *G. theta* (e.g., GenBank accession no. CAI77906) *C. butyricum* (e.g., GenBank accession no. ZP_04525837) *L. plantarum* (e.g., GenBank accession no. EFK28054) *L. suebicus* (e.g., GenBan accession no. ZP_09451344) |

N-acetylgalactosaminyltransferase (e.g., beta-1,3-GalNAcT or beta-1,4-GalNAcT) is an enzyme that catalyzes the reaction in which a GalNAc residue is added onto a suitable acceptor, such as a peptide or an oligosaccharide. Examples include LgtD from *H. influenza*, (GenBank accession no. L42023.1. Other examples include, but are not limited to, LgtD of *B. garinii* (e.g., GenBank accession no. AEW68905), LgtD of *N. lactamica* (e.g., GenBank accession no. AAN08512), and LgtD of *R. felis* (e.g., GenBank accession no. YP_246702).

Any of the enzymes used in the combined UDP-GalNAc regeneration system/GalNAcT approach can be either a wild-type enzyme or a functional variant thereof, as described herein. Any conventional method can be used for preparing such enzyme. In one example, this approach is applied for synthesizing Gb4 from Gb3. See, e.g., FIG. 2B.

GDP-Fuc Regeneration System and its Use in Fucosylation

An GDP-Fuc regeneration system can be co-used with a fucosyltransferase (e.g., an alpha1,2-fucosyltransferase, an alpha1,3-fucosyltransferase, or an alpha2,6-fucosyltransferase) to add a fucose residue to a suitable acceptor, such as an oligosaccharide, which can be conjugated to another molecule such as a lipid or a polypeptide.

Enzymes involved in an exemplary GDP-Fuc regeneration system are shown in Table 4 below:

TABLE 4

Enzymes Used in GDP-Fuc Regeneration System

| Enzyme | Activity | Examples |
| --- | --- | --- |
| L-fucokinase/GDP-fucose pyrophosphorylase (FKP) | A biofunctional enzyme that generates Fuc-1-P and GDP-Fuc from fucose and ATP | *B. fragilis* (e.g., GenBank accession no. CR626927.1 *H. sapiens* (e.g., GenBank accession no. NP_003829) *R. norvegicus* (e.g., GenBank accession no. NP_955788) |

TABLE 4-continued

Enzymes Used in GDP-Fuc Regeneration System

| Enzyme | Activity | Examples |
|---|---|---|
| Pyruvate kinase (PykF) | Catalyzes the transfer of a phosphate group from phosphoenolpyruvate (PEP) to ADP, producing pyruvate and ATP or UTP | E. coli (e.g., GenBank accession no. U00096.2) N. hamburgensis (e.g., GenBank accession no. YP_576506) R. palustris (e.g., GenBank accession no. YP_7830161) M. ruestringensis (e.g., GenBank accession no. YP_004787669) H. hydrossis (e.g., GenBank accession no. YP_004450514) S. coccoides (e.g., GenBank accession no. YP_00441096) |
| Pyrophosphatase (PPA) (Optional) | Acid anhydride hydrolase that acts upon diphosphate bonds | E. coli (e.g., GenBank accession no. U00096.2 G. theta (e.g., GenBank accession no. CAI77906) C. butyricum (e.g., GenBank accession no. ZP_04525837) L. plantarum (e.g., GenBank accession no. EFK28054) L. suebicus (e.g., GenBan accession no. ZP_09451344) |

A fucosyltransferase transfers an L-fucose sugar from a GDP-fucose (guanosine diphosphate-fucose) donor substrate to an acceptor substrate, which can be another sugar. Fucosyltransferase can add the fucose residue to a core GlcNAc (N-acetylglucosamine) sugar as in the case of N-linked glycosylation, or to a protein, as in the case of O-linked glycosylation. Fucosyltransferases include alpha1,3-fucosyltransferase, alpha1,2-fucosyltransferase, and alpha1,6-fucosyltransferase. Examples include alpha1,2-fucosyltransferase from E. coli (e.g., GenBank accession no. U00096.2), alpha 1,3-fucosyltransferase from B. fragilis (e.g., GenBank accession no. YP_213404) and from X. laevis (e.g., GenBank accession no. NP_001083664), alpha 1,6-fucosyltransferase from X. Any of the enzymes used in the combined GDP-Fuc regeneration system/FucT approach can be either a wild-type enzyme or a functional variant thereof, as described herein. Any conventional method can be used for preparing such enzyme. In one example, this approach is applied for synthesizing Gb4 from Gb3. See, e.g., FIG. 2D.

CMP-Neu5Ac Regeneration System and its Use in Sialylation

An CMP-Neu5Ac regeneration system can be coupled with a sialyltransferase, such as an alpha 2,3-sialyltransferase, to add a sialic acid residue (Neu5Ac) to a suitable acceptor substrate, such as an oligosaccharide.

Enzymes involved in an exemplary CMP-Neu5Ac regeneration system are shown in Table 5 below:

TABLE 5

Enzymes Used in CMP-Neu5Ac Regeneration System

| Enzyme | Activity | Examples |
|---|---|---|
| Cytidine monophosphate kinase (CMK) | Catalyzes phosphorylation of CMP to produce CDP | E. coli (e.g., GenBank accession no. U00096.2 B. amyloliquefaciens (e.g., GenBank accession no. ABS74466) M. leprae (e.g., GenBank accession no. CAB08279) M. avium (e.g., GenBank accession no. AAS03731) B. garinii (e.g., GenBank accession no. AEW68468) |
| CMP-sialic acid synthetase (Css) | Catalyzes the synthesis of CMP sialic acid from CTP and sialic acid. | P. multocida (e.g., GenBank accession no. AE004439.1 N. meningitidis (e.g., GenBank accession no. AAB60780) O. mykiss (e.g., GenBank accession no. BAB47150) I. ioihiensis (e.g., GenBank accession no. AAV81361) C. jejuni (e.g., GenBank accession no. ABI32334) |

TABLE 5-continued

Enzymes Used in CMP-Neu5Ac Regeneration System

| Enzyme | Activity | Examples |
|---|---|---|
| Pyruvate kinase (PykF) | Catalyzes the transfer of a phosphate group from phosphoenolpyruvate (PEP) to ADP, producing pyruvate and ATP or UTP | *E. coli* (e.g., GenBank accession no. U00096.2) *N. hamburgensis* (e.g., GenBank accession no. YP_576506) *R. palustris* (e.g., GenBank accession no. YP_7830161) *M. ruestringensis* (e.g., GenBank accession no. YP_004787669) *H. hydrossis* (e.g., GenBank accession no. YP_004450514) *S. coccoides* (e.g., GenBank accession no. YP_00441096) |
| Pyrophosphatase (PPA) (Optional) | Acid anhydride hydrolase that acts upon diphosphate bonds | *E. coli* (e.g., GenBank accession no. U00096.2 *G. theta* (e.g., GenBank accession no. CAI77906) *C. butyricum* (e.g., GenBank accession no. ZP_04525837) *L. plantarum* (e.g., GenBank accession no. EFK28054) *L. suebicus* (e.g., GenBan accession no. ZP_09451344) |

Sialyltransferases are enzymes that transfer sialic acid to nascent oligosaccharide. This family of enzymes adds sialic acid to the terminal portions of sialylated glycolipids (gangliosides) or to the N- or O-linked sugar chains of glycoproteins. There are about twenty different sialyltransferases, including sialyltransferases that add sialic acid with an alpha 2,3 linkage to galactose (e.g., alpha 2,3-sialyltransferase), and sialyltransferases that add sialic acid with an alpha 2,6 linkage to galactose or N-acetylgalactosamine (e.g., alpha 2,6-sialyltransferase). Examples include alpha 2,3-sialyltransferase from, e.g., *M. bacteria* (GenBank accession no. AB308042.1), *M. musculus* (e.g., GenBank accession no. BAA06068), or *P. multocida* (e.g., GenBank accession no. AET17056); and alpha 2,6-sialyltransferase from, e.g., *B. taurus* (e.g., GenBank accession no. NP_001008668), *C. griseus* (e.g., GenBank accession no. NP_001233744), or *R. norvegicus* (e.g., GenBank accession no. AAC42086).

Any of the enzymes used in the combined CMP-Neu5Ac regeneration system/sialyltransferase approach can be either a wild-type enzyme or a functional variant thereof, as described herein. Any conventional method can be used for preparing such enzyme. In one example, this approach is applied for synthesizing Gb4 from Gb3. FIG. 2E.

Synthesis of Globo-Series Oligosaccharides

The above-described combined approaches involving UDP-Gal regeneration/galactosyltransferase, UDP-GalNAc regeneration/GalNAcT, GDP-Fuc regeneration/fucosyltransferase, and CMP-Neu5Ac regeneration/sialyltransferase can be applied, either independently, or in combination, to synthesize Globo-series oligosaccharides, including Gb3. Gb4, Gb5, Globo H (fucosyl-Gb5), and SSEA4 (sialyl-Gb5). As discussed in greater detail below, all of these Globo-series oligosaccharides can be either substituted or unsubstituted.

Step S-1

The first step in the biosynthetic approach (S-1) involves enzymatic conversion of a compound of Formula (I), or salt thereof, to a compound of Formula (II), or salt thereof:

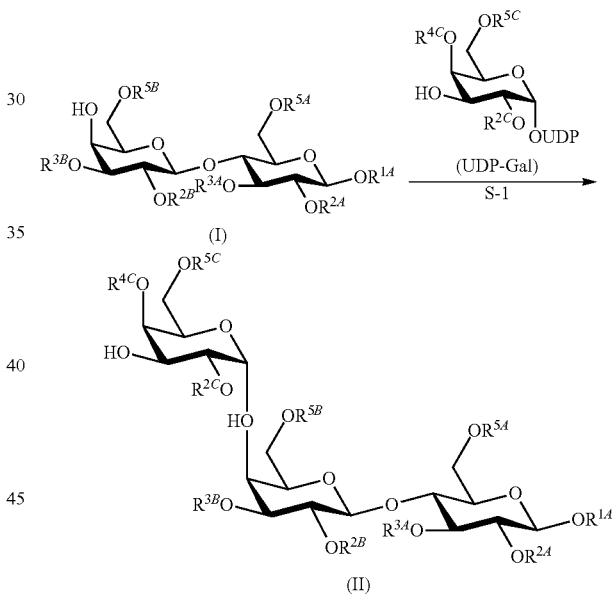

wherein $R^{1A}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group; and each instance of $R^{2A}$, $R^{3A}$, $R^{5A}$, $R^{2B}$, $R^{3B}$, $R^{5B}$, $R^{2C}$, $R^{4C}$, and $R^{5C}$ is independently hydrogen, substituted or unsubstituted $C_{1-6}$ alkyl, or an oxygen protecting group.

Thus, in one aspect, provided is a method of enzymatically synthesizing a compound of Formula (II), or salt thereof, from a compound of Formula (I), or salt thereof, comprising converting a compound of Formula (I) to a compound of Formula (II), or salt thereof, in the presence of uridine diphosphate-Gal (UDP-Gal) and an alpha-1,4 galactosyltransferase, and regenerating UDP-Gal from galactose in the presence of the set of enzymes listed in Table 1 above. See, e.g., FIG. 2A. To perform this enzymatic reaction, necessary components, such as galactose, galactosyltransferase, the set of UDP-Gal regeneration enzymes, ATP, UTP, and others (e.g., Mg$^{++}$), can be mix to form a reaction mixture, which can be incubated under suitable conditions allowing production of Formula (II) compounds. Such conditions are well known to those skilled in the art. See also Examples below.

The $R^{1A}$ group can serve as a functional group allowing conjugation of the Globo-series oligosaccharides to another molecule, such as a protein or a lipid. Alternative, it can serve as a protecting group.

In certain embodiments, $R^{1A}$ is hydrogen.

In other embodiments, $R^{1A}$ is substituted or unsubstituted alkyl, e.g., substituted or unsubstituted $C_{1-6}$alkyl, substituted or unsubstituted $C_{2-6}$alkyl, substituted or unsubstituted $C_{3-6}$alkyl, substituted or unsubstituted $C_{4-6}$alkyl, substituted or unsubstituted $C_{5-6}$alkyl, substituted or unsubstituted $C_{2-5}$alkyl, substituted or unsubstituted $C_{2-4}$alkyl, substituted or unsubstituted $C_{2-3}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. Biotin and a ceramide, as defined herein, are encompassed by substituted alkyl. In certain embodiments, $R^{1A}$ is an unsubstituted alkyl, e.g., in certain embodiments, $R^{1A}$ is methyl, ethyl, propyl, isopropyl, sec-butyl, iso-butyl, or tert-butyl. Alternatively, in certain embodiments, $R^{1A}$ is a substituted alkyl. In certain embodiments, $R^{1A}$ is alkyl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, such substituents are substituted at the terminal position (last carbon atom) of the alkyl group. In certain embodiments, $R^{1A}$ is alkyl substituted with one or more amino ($-NH_2$) groups. In certain embodiments, $R^{1A}$ is alkyl substituted at the terminal position (last carbon atom) with an amino ($-NH_2$) group. In certain embodiments, $R^{1A}$ is $-(CH_2)_n-NH_2$ wherein n is 1, 2, 3, 4, 5, or 6. In certain embodiments, $R^{1A}$ is 5-pentylamino ($-(CH_2)_5-NH_2$)

In certain embodiments, $R^{1A}$ is substituted or unsubstituted alkenyl, e.g., substituted or unsubstituted $C_{2-6}$alkenyl, substituted or unsubstituted $C_{3-6}$alkenyl, substituted or unsubstituted $C_{4-6}$alkenyl, substituted or unsubstituted $C_{5-6}$alkenyl, substituted or unsubstituted $C_{2-5}$alkenyl, substituted or unsubstituted $C_{2-4}$alkenyl, substituted or unsubstituted $C_{2-3}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^{1A}$ is $-(CH_2)_m-CH=CH_2$, wherein n is 1, 2, or 3. In certain embodiments, $R^{1A}$ is allyl ($-CH_2CH=CH_2$). In certain embodiments, $R^{1A}$ is alkenyl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, such substituents are substituted at the terminal position (last carbon atom) of the alkenyl group In certain embodiments, $R^{1A}$ is substituted or unsubstituted alkynyl, e.g., substituted or unsubstituted $C_{2-6}$alkynyl, substituted or unsubstituted $C_{3-6}$alkynyl, substituted or unsubstituted $C_{4-6}$alkynyl, substituted or unsubstituted $C_{5-6}$alkynyl, substituted or unsubstituted $C_{2-5}$alkynyl, substituted or unsubstituted $C_{2-4}$alkynyl, substituted or unsubstituted $C_{2-3}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^{1A}$ is alkynyl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group. In certain embodiments, such substituents are substituted at the terminal position (last carbon atom) of the alkynyl group.

In certain embodiments, $R^{1A}$ is substituted or unsubstituted heterocyclyl, e.g., substituted or unsubstituted 5- to 8-membered heterocyclyl, substituted or unsubstituted 5- to 7-membered heterocyclyl, substituted or unsubstituted 5- to 6-membered heterocyclyl, substituted or unsubstituted 5-membered heterocyclyl, substituted or unsubstituted 6-membered heterocyclyl, substituted or unsubstituted 7-membered heterocyclyl, or substituted or unsubstituted 8-membered heterocyclyl. In certain embodiments, $R^{1A}$ is heterocyclyl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group.

In certain embodiments, $R^{1A}$ is substituted or unsubstituted carbocyclyl, e.g., substituted or unsubstituted $C_{3-6}$ carbocyclyl, substituted or unsubstituted $C_{3-5}$ carbocyclyl, substituted or unsubstituted $C_{3-4}$ carbocyclyl, substituted or unsubstituted $C_3$ carbocyclyl, substituted or unsubstituted $C_4$ carbocyclyl, substituted or unsubstituted $C_5$ carbocyclyl, or substituted or unsubstituted $C_6$ carbocyclyl. In certain embodiments, $R^{1A}$ is carbocyclyl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group.

In certain embodiments, $R^{1A}$ is substituted or unsubstituted aryl, e.g., substituted or unsubstituted $C_6$ aryl (phenyl) or substituted or unsubstituted $C_{10}$ aryl (naphthyl). In certain embodiments, $R^{1A}$ is aryl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group.

In certain embodiments, $R^{1A}$ is substituted or unsubstituted heteroaryl, e.g., substituted or unsubstituted 5-membered heteroaryl or substituted or unsubstituted 6-membered heteroaryl. In certain embodiments, $R^{1A}$ is heteroaryl which is further substituted with a substituted or unsubstituted thio, substituted or unsubstituted amino, carbonyl (e.g., carboxylic acid), azido, alkenyl (e.g., allyl), alkynyl (e.g., propargyl), biotin, or a ceramide group.

In certain embodiments, $R^{1A}$ is hydrogen, allyl, substituted alkyl, biotin, or a ceramide.

It is further contemplated herein that $R^{1A}$ can be a mixture of any of the above recited non-hydrogen groups, e.g., substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, to provide a linker group comprising 1, 2, 3, 4, 5, 6, 7, 8, 9, or 10 different combinations of groups. As a non-limiting example, $R^{1A}$ may be a linker group comprising alkyl and aryl combination of groups, e.g., such as alkyl-aryl-alkyl, and which may optionally be further substituted at any position on the linker group (e.g., the terminal position) with a substituted or unsubstituted thio, substituted or unsubstituted amino, carbonyl (e.g., carboxylic acid), azido, alkenyl (e.g., allyl), alkynyl (e.g., propargyl), biotin, or a ceramide group.

In certain embodiments, $R^{1A}$ is an oxygen protecting group, as defined herein.

In certain embodiments, $R^{2A}$ is hydrogen. In certain embodiments, $R^{2A}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2A}$ is an oxygen protecting group.

In certain embodiments, $R^{3A}$ is hydrogen. In certain embodiments, $R^{3A}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3A}$ is an oxygen protecting group.

In certain embodiments, $R^{5A}$ is hydrogen. In certain embodiments, $R^{5A}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{5A}$ is an oxygen protecting group.

In certain embodiments, $R^{2B}$ is hydrogen. In certain embodiments, $R^{2B}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2B}$ is an oxygen protecting group.

In certain embodiments, $R^{3B}$ is hydrogen. In certain embodiments, $R^{3B}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3B}$ is an oxygen protecting group.

In certain embodiments, $R^{5B}$ is hydrogen. In certain embodiments, $R^{5B}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{5B}$ is an oxygen protecting group.

In certain embodiments, $R^{2C}$ is hydrogen. In certain embodiments, $R^{2C}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2C}$ is an oxygen protecting group.

In certain embodiments, $R^{4C}$ is hydrogen. In certain embodiments, $R^{4C}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{4C}$ is an oxygen protecting group.

In certain embodiments, $R^{5C}$ is hydrogen. In certain embodiments, $R^{5C}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{5C}$ is an oxygen protecting group.

In certain embodiments, each instance of $R^{2A}$, $R^{3A}$, $R^{5A}$, $R^{2B}$, $R^{3B}$, $R^{5B}$, $R^{2C}$, $R^{4C}$, and $R^{5C}$ is independently hydrogen. In certain embodiments, $R^{1A}$ is substituted or unsubstituted alkenyl, and each instance of $R^{2A}$, $R^{3A}$, $R^{5A}$, $R^{2B}$, $R^{3B}$, $R^{5B}$, $R^{2C}$, $R^{4C}$, and $R^{5C}$ is independently hydrogen. In certain embodiments, $R^{1A}$ is substituted or unsubstituted alkyl, and each instance of $R^{2A}$, $R^{3A}$, $R^{5A}$, $R^{2B}$, $R^{3B}$, $R^{5B}$, $R^{2C}$, $R^{4C}$, and $R^{5C}$ is independently hydrogen.

Exemplary compounds of Formula (I) include, but are not limited to, and salts thereof.

Exemplary compounds of Formula (II) include, but are not limited to,

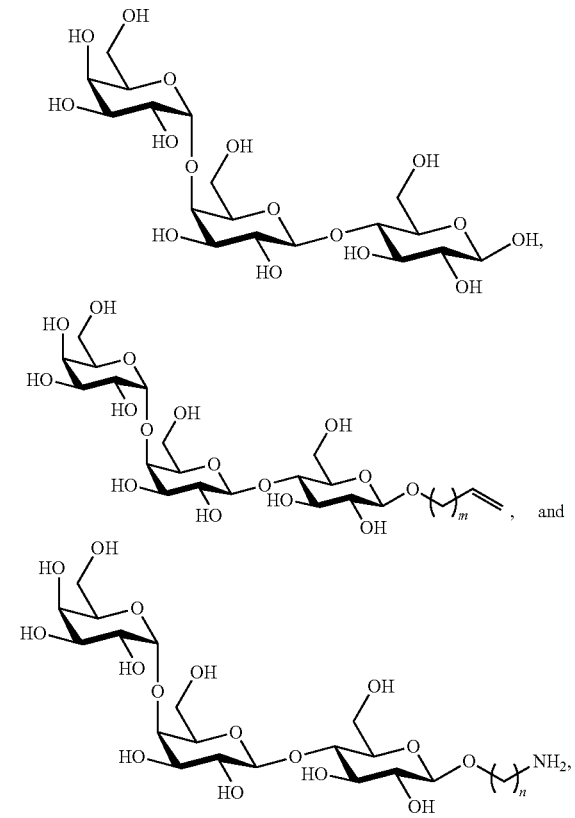

and salts thereof.

Step S-2

The second step in the biosynthetic approach (S-2) involves enzymatic conversion of a compound of Formula (II), or salt thereof, to a compound of Formula (III), or salt thereof:

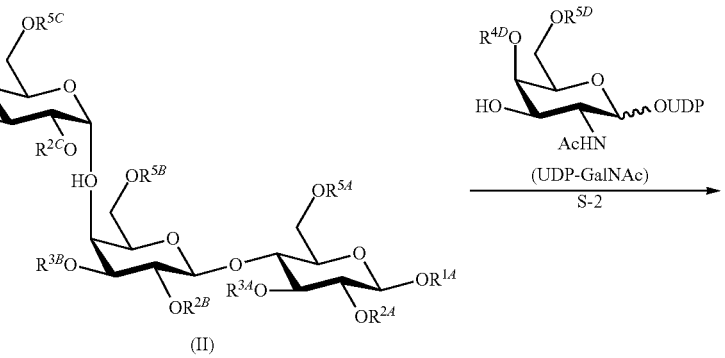

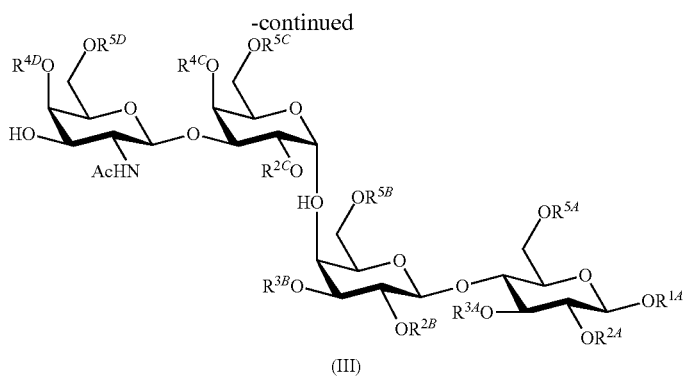

(III)

wherein $R^{1A}$, $R^{2A}$, $R^{3A}$, $R^{5A}$, $R^{2B}$, $R^{3B}$, $R^{5B}$, $R^{2C}$, $R^{4C}$, and $R^{5C}$ are as defined herein; and each instance of $R^{4D}$ and $R^{5D}$ is independently hydrogen, substituted or unsubstituted $C_{1-6}$ alkyl, or an oxygen protecting group.

In certain embodiments, $R^{2D}$ is hydrogen. In certain embodiments, $R^{2D}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2D}$ is a nitrogen protecting group, e.g., acetyl (Ac, —C=OCH$_3$).

In certain embodiments, $R^{4D}$ is hydrogen. In certain embodiments, $R^{4D}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{4D}$ is an oxygen protecting group.

In certain embodiments, $R^{5D}$ is hydrogen. In certain embodiments, $R^{5D}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{5D}$ is an oxygen protecting group.

In certain embodiments, both of $R^{4D}$ and $R^{5D}$ are hydrogen. In certain embodiments, $R^{2D}$ is a nitrogen protecting group, e.g., acetyl (Ac, —C=OCH$_3$), and $R^{4D}$ and $R^{5D}$ are each hydrogen.

Exemplary compounds of Formula (III) include, but are not limited to,

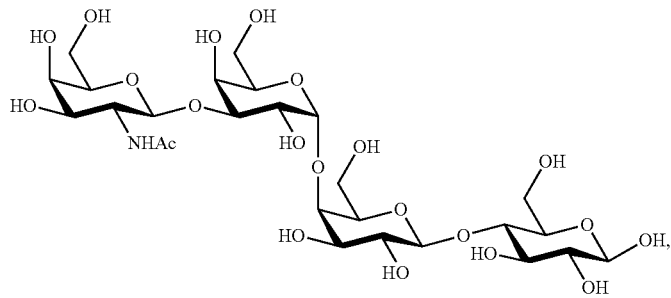

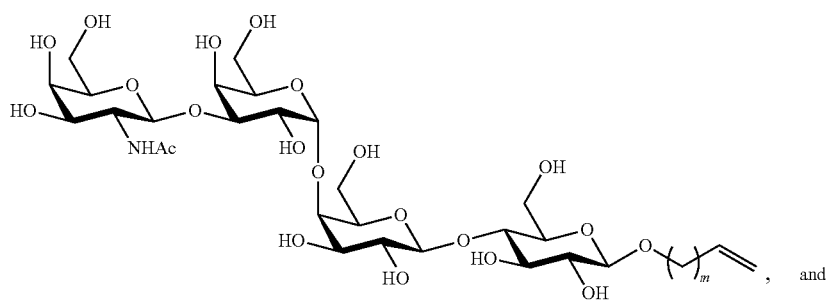

, and

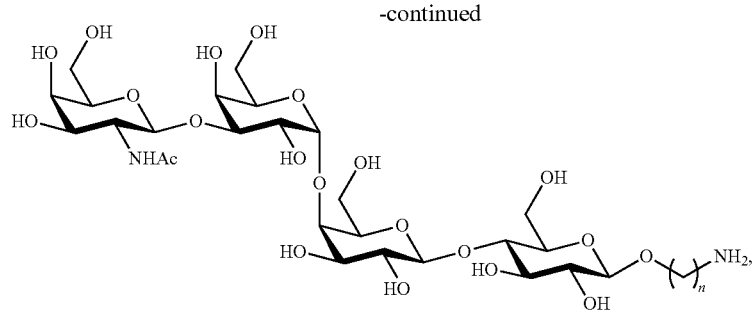

and salts thereof.

In Step S-2, a method of enzymatically synthesizing a compound of Formula (III), or salt thereof, from a compound of Formula (II), or salt thereof, is performed under suitable conditions. A substrate of Formula (II) can be prepared by any method known in the art or disclosed herein. In some examples, the Formula (II) compound is isolated from the reaction mixture described in Step S-1 above. In other examples, the whole reaction mixture of Step S-1 is used without purification of the Formula (II) compound produced therein. The Formula (II) compound can be incubated with UDP-GalNAc in the presence of a GalNAcT (e.g., a beta1,3-GalNAcT) under conditions allowing convertion of the Formula (II) compound to a Formula (III) compound. In some example, this GalNAcT-catalyzed reaction is coupled with the UDP-GalNAc regeneration process as described herein. FIG. 2B. See also Examples below.

Step S-3

The third step in the biosynthetic approach (S-3) involves enzymatic conversion of a compound of Formula (III), or salt thereof, to a compound of Formula (IV), or salt thereof:

wherein $R^{1A}$, $R^{2A}$, $R^{3A}$, $R^{5A}$, $R^{2B}$, $R^{3B}$, $R^{5B}$, $R^{2C}$, $R^{4C}$, $R^{5C}$, $R^{2D}$, $R^{4D}$ and $R^{5D}$ are as defined herein; and each instance of $R^{2E}$, $R^{3E}$, $R^{4E}$, and $R^{5E}$ is independently hydrogen, substituted or unsubstituted $C_{1-6}$ alkyl, or an oxygen protecting group.

In certain embodiments, $R^{2E}$ is hydrogen. In certain embodiments, $R^{2E}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2E}$ is an oxygen protecting group.

In certain embodiments, $R^{3E}$ is hydrogen. In certain embodiments, $R^{3E}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3E}$ is an oxygen protecting group.

In certain embodiments, $R^{4E}$ is hydrogen. In certain embodiments, $R^{4E}$ is substituted or unsubstituted $C_{1-6}$ alkyl,

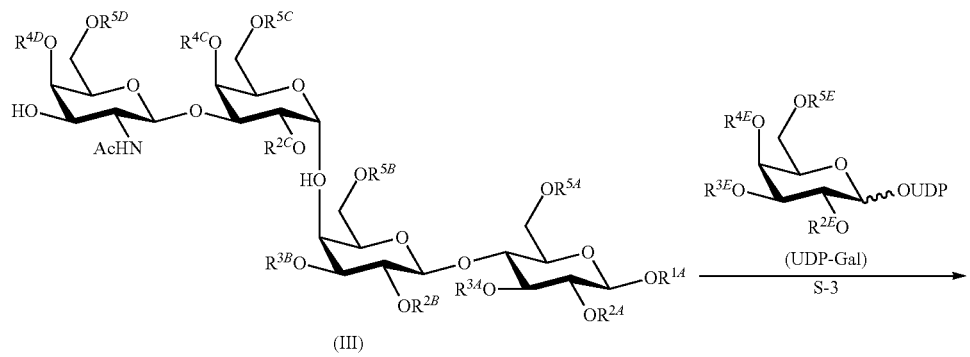

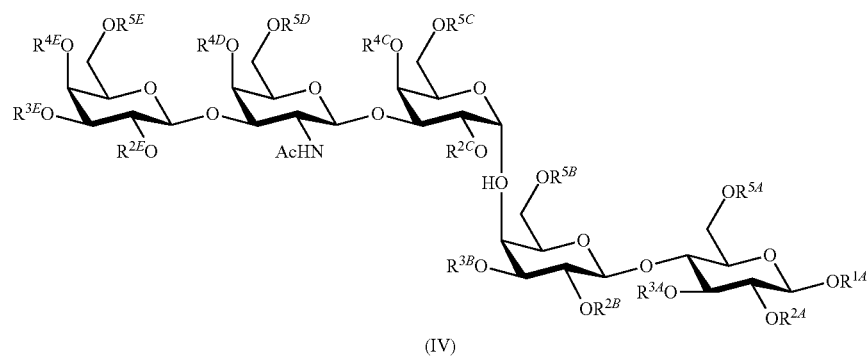

e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{4E}$ is an oxygen protecting group.

In certain embodiments, $R^{5E}$ is hydrogen. In certain embodiments, $R^{5E}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{5E}$ is an oxygen protecting group.

In certain embodiments, $R^{3E}$ is hydrogen. In certain embodiments, $R^{3E}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3E}$ is an oxygen protecting group.

In certain embodiments, each instance of $R^{2E}$, $R^{3E}$, $R^{4E}$, and $R^{5E}$ is hydrogen.

Exemplary compounds of Formula (IV) include, but are not limited to, suitable conditions known to those skilled in the art. A substrate of Formula (III), such as Gb4, can be prepared by any method known in the art or disclosed herein. In some examples, the Formula (III) compound is isolated from the reaction mixture described in Step S-2 above. In other examples, the whole reaction mixture of Step S-2 is used without purification of the Formula (III) compound produced therein. The Formula (III) compound can be incubated with UDP-Gal in the presence of a beta1,3-galactosyltransferase under conditions allowing convertion of the Formula (III) compound to a Formula (IV) compound. In some example, this GalT-catalyzed reaction is coupled with the UDP-Gal regeneration process as described herein. FIG. 2A. See also Examples below.

In some embodiments, a beta1,3-GalNAcT/beta1,3-GalT bifunctional enzyme, such as LgtD from, e.g., *H. influenza*, is used in both Steps S-2 and S-3.

Step S-4

The compound of Formula (IV) may then be substituted at various positions on the terminal Ring E. For example, in certain embodiments of Formula (IV), wherein $R^{2E}$ is hydro-

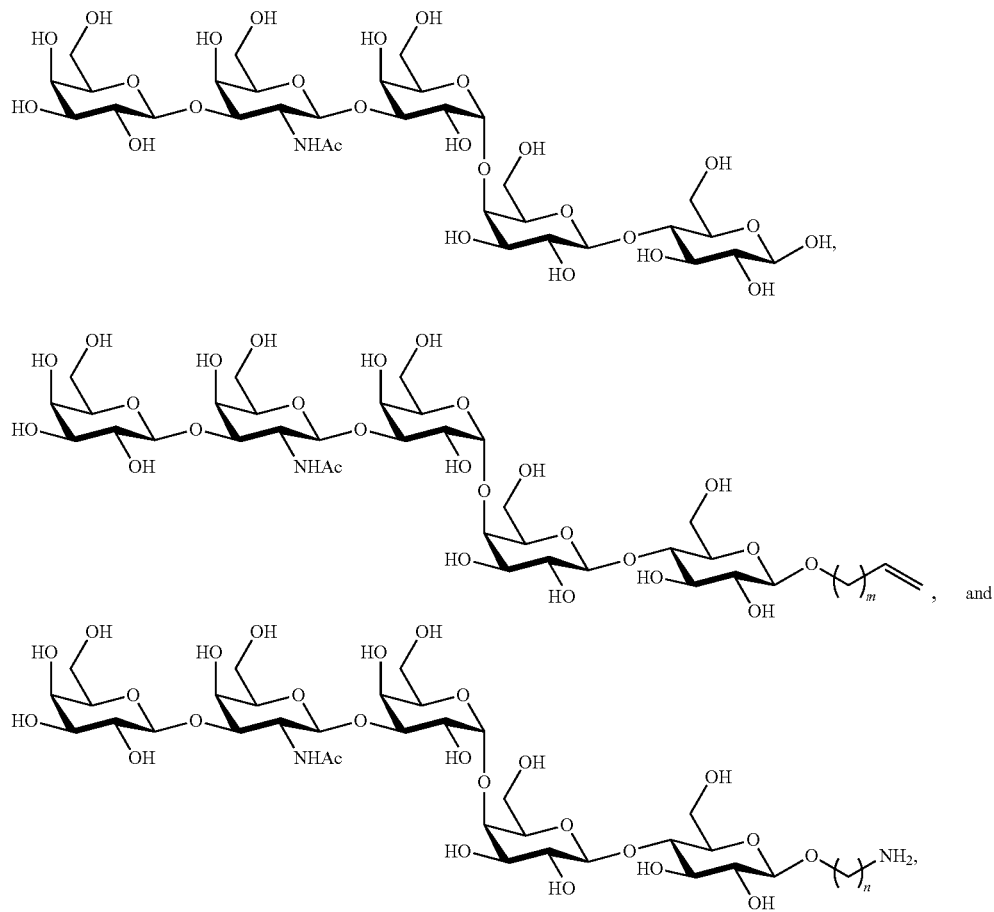

and salts thereof.

Step S-3 involves an enzymatic reaction via the activity of a beta1,3-galactosyltransferase, which is performed under gen, an optional step in the biosynthetic approach (S-4) involves enzymatic conversion of a compound of Formula (IV-a), or salt thereof, to a compound of Formula (V), or salt thereof:

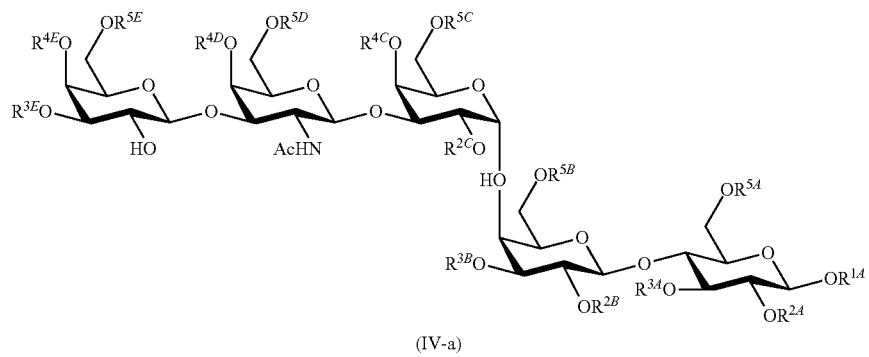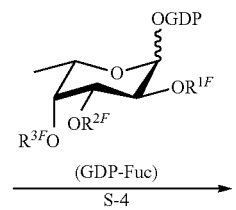

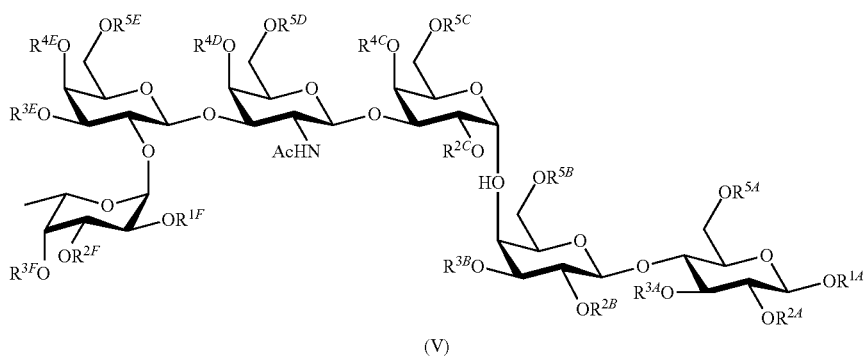

wherein $R^{1A}$, $R^{2A}$, $R^{3A}$, $R^{5A}$, $R^{2B}$, $R^{3B}$, $R^{5B}$, $R^{2C}$, $R^{4C}$, $R^{5C}$, $R^{2D}$, $R^{4D}$, $R^{5D}$, $R^{3E}$, $R^{4E}$, and $R^{5E}$ are as defined herein; and each instance of $R^{1F}$, $R^{2F}$, and $R^{3F}$ is independently hydrogen, substituted or unsubstituted $C_{1-6}$ alkyl, or an oxygen protecting group.

In certain embodiments, $R^{1F}$ is hydrogen. In certain embodiments, $R^{1F}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{1F}$ is an oxygen protecting group.

In certain embodiments, $R^{2F}$ is hydrogen. In certain embodiments, $R^{2F}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{2F}$ is an oxygen protecting group.

In certain embodiments, $R^{3F}$ is hydrogen. In certain embodiments, $R^{3F}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3F}$ is an oxygen protecting group.

In certain embodiments, each instance of $R^{1F}$, $R^{2F}$, and $R^{3F}$ is hydrogen.

Exemplary compounds of Formula (V) include, but are not limited to,

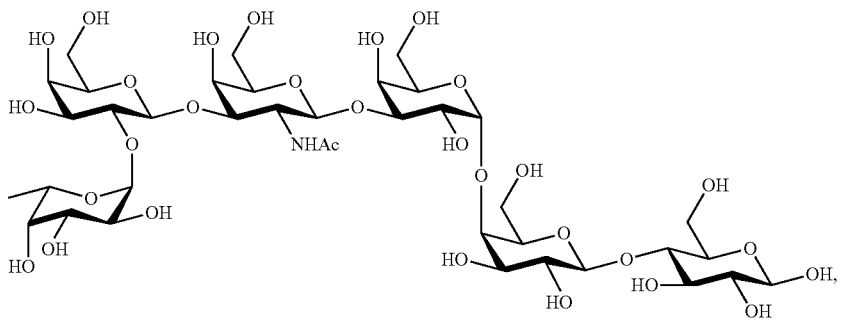

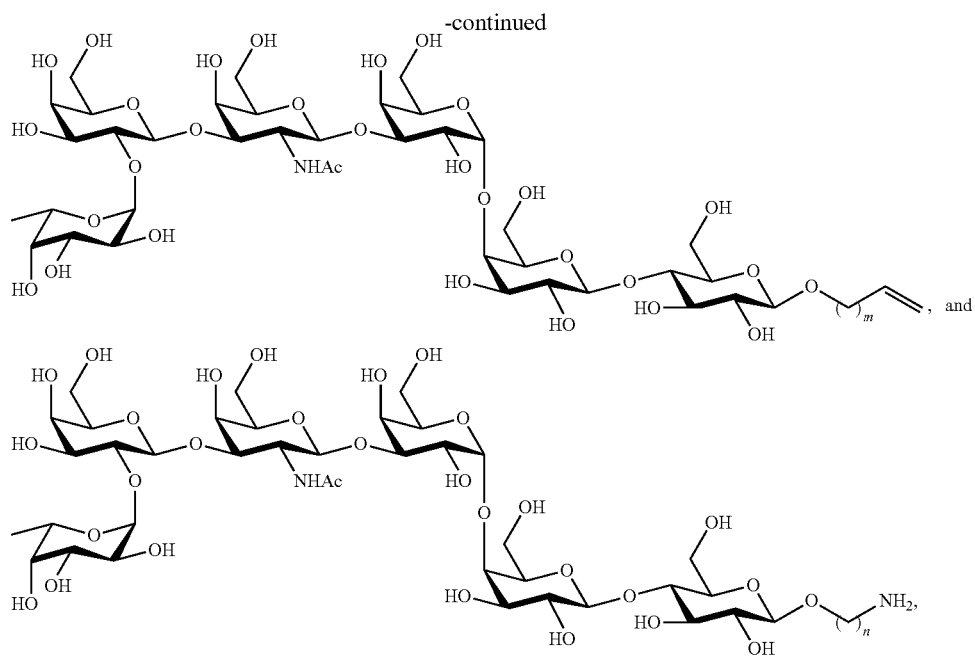

and salts thereof.

Step S-4 involves an enzymatic reaction via the activity of an alpha1,2-fucosyltransferase, which is performed under suitable conditions known to those skilled in the art. A substrate of Formula (IV), such as Gb5, can be prepared by any method known in the art or disclosed herein. In some examples, the Formula (IV) compound is isolated from the reaction mixture described in Step S-3 above. In other examples, the whole reaction mixture of Step S-3 is used without purification of the Formula (V) compound produced therein. The Formula (IV) compound can be incubated with GDP-Fuc in the presence of the fucosyltransferase under conditions allowing convertion of the Formula (IV) compound to a Formula (V) compound. In some example, this FucT-catalyzed reaction is coupled with the GDP-Fuc regeneration process as described herein. FIG. 2D. See also Examples below.

Step S-5

In other embodiments of Formula (IV), wherein $R^{3E}$ is hydrogen, an optional step in the biosynthetic approach (S-5) involves enzymatic conversion of a compound of Formula (IV-b), or salt thereof, to a compound of Formula (VI), or salt thereof:

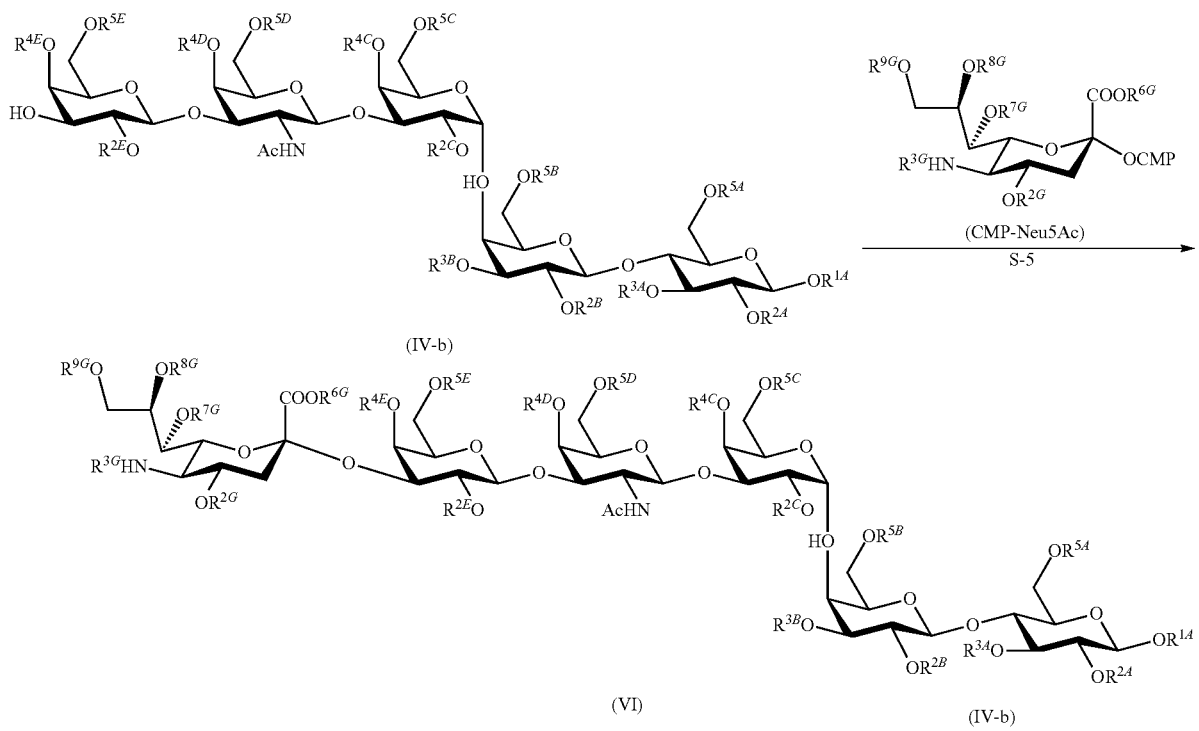

wherein $R^{1A}$, $R^{2A}$, $R^{3A}$, $R^{5A}$, $R^{2B}$, $R^{3B}$, $R^{5B}$, $R^{2C}$, $R^{4C}$, $R^{5C}$, $R^{2D}$, $R^{4D}$, $R^{5D}$, $R^{2E}$, $R^{4E}$, and $R^{5E}$ are as defined herein; $R^{3G}$ is hydrogen, substituted or unsubstituted $C_{1-6}$ alkyl, or a nitrogen protecting group; and each instance of $R^{6G}$, $R^{7G}$, $R^{8G}$, and $R^{9G}$, is independently hydrogen, substituted or unsubstituted $C_{1-6}$ alkyl, or an oxygen protecting group.

In certain embodiments, $R^{3G}$ is hydrogen. In certain embodiments, $R^{3G}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{3G}$ is a nitrogen protecting group, e.g., acetyl (Ac, —C=OCH$_3$).

In certain embodiments, $R^{6G}$ is hydrogen. In certain embodiments, $R^{6G}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{6G}$ is an oxygen protecting group.

In certain embodiments, $R^{7G}$ is hydrogen. In certain embodiments, $R^{7G}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{7G}$ is an oxygen protecting group.

In certain embodiments, $R^{8G}$ is hydrogen. In certain embodiments, $R^{8G}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{8G}$ is an oxygen protecting group.

In certain embodiments, $R^{9G}$ is hydrogen. In certain embodiments, $R^{9G}$ is substituted or unsubstituted $C_{1-6}$ alkyl, e.g., substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{9G}$ is an oxygen protecting group.

In certain embodiments, each instance of $R^{6G}$, $R^{7G}$, $R^{8G}$, and $R^{9G}$ is hydrogen. In certain embodiments, $R^{3G}$ is a nitrogen protecting group, e.g., acetyl (Ac, —C=OCH$_3$), each instance of $R^{6G}$, $R^{7G}$, $R^{8G}$, and $R^{9G}$ is hydrogen.

Exemplary compounds of Formula (V) include, but are not limited to,

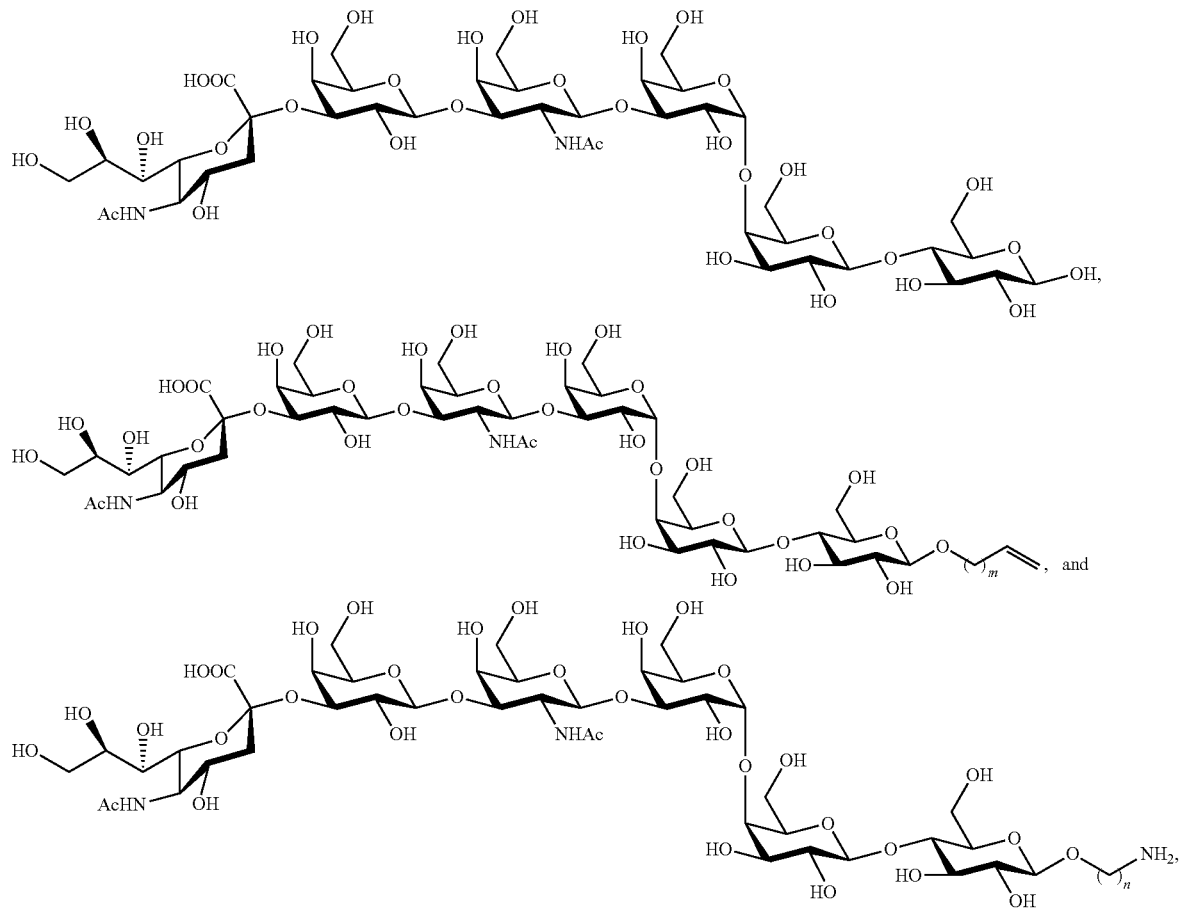

and salts thereof.

Step S-5 involves an enzymatic reaction via the activity of an alpha2,3-sialyltransferase, which is performed under suitable conditions known to those skilled in the art. A substrate of Formula (IV), such as Gb5, can be prepared by any method known in the art or disclosed herein. In some examples, the Formula (IV) compound is isolated from the reaction mixture described in Step S-3 above. In other examples, the whole reaction mixture of Step S-3 is used without purification of the Formula (IV) compound produced therein. The Formula (IV) compound can be incubated with CMP-Neu5Ac in the presence of the sialyltransferase under conditions allowing convertion of the Formula (IV) compound to a Formula (V) compound. In some example, this Sialyltransferase-catalyzed reaction is coupled with the CMP-Neu5Ac regeneration process as described herein. FIG. 2E. See also Examples below.

Each of the Steps S1-S5, as well as any combination of consecutive steps as described above, is within the scope of this disclosure. Also within the scope of the present disclosure are any of the compounds produced in any of the synthesis methods described herein, e.g., those described above.

In some embodiments, the present disclosure features methods for synthesizing Globo H or $SSEA_4$ from lactose via a chain reaction comprising Steps S-1, S-2, S-3, and S-4 or Steps S-1, S-2, S-3, or S-5 described above. The Globo H or SSEA4 can be either untailed ($R^{1-4}$ being hydrogen; see FIGS. 3 and 4), or tailed (e.g., $R^{1-4}$ being allyl; see FIGS. 5 and 6). In each step, the glycosyltransferase reaction can be coupled with the corresponding nucleotide sugar regeneration process. FIGS. 3-6. In one example, the above-described method is performed in a one-pot manner, i.e., each prior reaction mixture is used directly for the next step reaction without purifying the substrate produced in the prior reaction. In other words, the one-pot approach is free of any step for purifying any intermediate. Alternatively, Steps S-1 and S-2 are performed in a one-spot manner without purification of any intermediate. After Step S-2, Gb4 is isolated from the reaction mixture and the purified GB4 is used for the following Steps S3, S4, and/or S5. No further purification step is performed for isolating other intermediate.

The enzymes used in each reaction step can be dissolved in each reaction mixture, or immobilized on one or more support members. When necessary, additional enzymes can be added during the chain reaction.

Enzymatic Reactors

A chain enzymatic reaction comprising any combination of two or more consecutive steps as described above can be performed in an enzymatic reactor, which comprises one or more reaction chambers. Each reaction chamber is designed for perform one step of the chain reaction. In particular, each reaction chamber comprises enzymes involved in one step of the reaction, including each of Steps 1-S to 5-S described above.

In some embodiments, one or more enzymes, or all of the enzymes, in each reaction chamber are immobilized on a suitable support member (e.g., a support membrane). When necessary, reaction chambers for consecutive reaction steps can be connected such that, after termination of the enzymatic reaction in a prior reaction chamber, the resultant reaction mixture can flow into the following reaction chamber to allow the next reaction step to occur. In some examples, the product from the prior reaction is not purified and the whole reaction mixture including the product is added into the next reaction chamber to allow occurrence of the next enzymatic reaction. See, e.g., FIGS. 3 and 4.

For example, the reaction of Step 1-S can be performed in a first reaction chamber in the enzymatic reactor, wherein one or enzymes involved in Step 1-S are immobilized on a support member. After termination of Step 1-S, the reaction mixture (including the Gb3 product) in the first reaction chamber is placed into a second reaction chamber containing all enzymes and reagents necessary for Step 2-S for synthesis of Gb4. In one example, the Gb4 is purified and used for the next reaction step. In another example, the whole reaction mixture in the second reaction chamber, including Gb4, is placed into a third reaction chamber that contains enzymes and reagents necessary for Step 3-S, in which Gb5 is synthesized. Afterwards, the reaction mixture from the third reaction chamber can be placed into a fourth reaction chamber containing enzymes and reagents necessary for Step 4-S or placed into a fifth reaction chamber containing enzymes and reagents necessary for Step 5-S.

In other embodiments, the enzymatic reactor contains one reaction chamber including enzymes, reagents, and the suitable substrate, necessary for one of the synthesis steps described above. The substrate is immobilized on a support member. In one example, a reaction chamber contains the enzymes and reagents necessary for Step 1-S, in which the substrate, Lac-allyl, is immobilized on a support member. After Step 1-S, in which Gb3-allyl is synthesized, the reaction mixture in the reaction chamber is replaced with a second reaction mixture containing enzymes and reagents necessary for Step 2-S. After synthesis of Gb4-allyl in Step 2-S, the second reaction mixture is replaced with a third reaction mixture containing enzymes and reagents for Step 3-S, in which Gb5-allyl is synthesized. Afterwards, the third reaction mixture is replaced with either a fourth reaction mixture containing the enzymes and reagents for Step 4-S (for synthesis of Globo H-allyl) or a fifth reaction mixture containing the enzymes and reagents for Step 5-S (for synthesis of $SSEA_4$-allyl).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

These and other aspects of the present invention will be further appreciated upon consideration of the following Examples, which are intended to illustrate certain particular embodiments of the invention but are not intended to limit its scope, as defined by the claims.

Example 1

Synthesis of Globo-Series Oligosaccharides

New Method for UDP-Gal Regeneration

In 2004, Kotake's group discovered an enzyme from Pea Sprouts, UDP-Sugar Pyrophosphorylase, which has broad substrate specificity toward different monosaccharide-1-phosphate to form UDP-Sugar.[19] Two years later, Kotake's and Somers' groups independently published similar function enzyme, AtUSP, existed in *Arabidopsis*.[20],[21] Very recently, the homologous enzymes also proved existing in parasites, *Leishmania* and *Trypanosoma*.[22],[23] The AtUSP enzyme is interesting because of its intrinsic ability to condense UTP with not only Glc-1-phosphate and Gal-1-phosphate but also other monosaccharide-1-P, GlcA-1-phosphate, and Xyl-1-phosphate. Therefore, we chose AtUSP to condense Gal-1-phosphate with UTP directly to render the UDP-Gal regeneration and to fulfill the third regeneration of UDP-Gal synthesis.

Synthesis of Allyl-Gb3

The reaction mixture (200 mL) contained 10 mmol of allyl-lac, 10 mmol of galactose, 22 mmol of Phosphoenolpyruvic acid (PEP), 0.05 mmol of ATP, 0.125 mmol of UTP with 10 mM MgCl$_2$ in 100 mM Tris-HCl buffer (pH 7.0). The reaction was initiated by addition 100 U of α-1,4-galactosyltransferase (LgtC), 50 U of galactokinase (GalK), 150 U of UDP-sugar pyrophosphorylase (AtUSP), 200 U of pyruvate kinase (PK) and 200 U of pyrophosphatase (PPA). The flask was incubated at 25° C. and the reaction progress was monitored by TLC, and stained by p-anisaldehyde. More enzymes were added if any of the reaction was incomplete until the reaction was complete, and the products were confirmed by TLC and ESI-MS.

Synthesis of Allyl-Gb4

Following the allyl-Gb3 synthesis, additional components were added, including 9.9 mmol of N-acetylgalactosamine (GalNAc), 22 mmol of PEP, 100 U of β-1,3-N-acetylgalactosaminyltransferase (β1,3GalNAcT, LgtD), 50 U of N-acetylhexosamine 1-kinase (NahK), 200 U of N-acetylglucosamine 1-phosphate uridylyltransferase (GlmU), 100 U of PK and 100 U of PPA, in 220 mL solution. The mixture was incubated at 25° C. and monitored by TLC and ESI-MS as before until the reaction was complete. The product was further purified by a C-18 gel column and characterized by NMR.

Synthesis of Allyl-Gb5

The reaction mixture (250 mL) contained 9 mmol of allyl-Gb4, 9 mmol of galactose, 22 mmol of PEP, 0.05 mmol of ATP, 0.125 mmol of UTP with 10 mM MgCl$_2$ in 100 mM Tris-HCl buffer (pH 7.0). The reaction was initiated by addition of 200 U of β-1,3-galactosyltransferase (β1,3GalT, LgtD), 50 U of GalK, 150 U of AtUSP, 100 U of PK and 100 U of PPA and incubated at 25° C., until completion.

Synthesis of Allyl-Globo H

A half amount of the reaction product of allyl-Gb5 (~4.5 mmol) without additional purification was used to produce allyl-globo H directly. A solution containing 5 mmol of fucose, 0.05 mmol of ATP, 0.5 mmol of GTP, 11 mmol PEP with 10 mM MgCl$_2$ in 100 mM Tris-HCl buffer (pH 7.0) was added 200 U of L-fucokinase/GDP-fucose pyrophosphorylase (FKP), 200 U of PK, 200 U of PPA and 200 U of α-1,2-fucosyltransferase (FutC) incubated at 25° C. until the reaction was complete, and the product was purified by C-18 gel chromatography as before and characterized.

Synthesis of Allyl-SSEA4

Another half of the allyl-Gb5 (4.5 mmol) reaction mixture was used for the synthesis of allyl-SSEA4 by adding 5 mmol of N-acetylneuraminic acid (Neu5Ac), 0.05 mmol of ATP, 0.25 mmol of CTP, 11 mmol of PEP with 10 mM MgCl$_2$ in 100 mM Tris-HCl buffer (pH 8.0) followed by 50 U of Cytidine monophosphate kinase (CMK), 120 U of CMP-sialic acid synthetase (CSS), 100 U of PK, 100 U of PPA and 150 U of α-2,3-sialyltransferase (JT-FAJ-16). The progress was monitored by TLC and the product was purified and characterized as described above.

Purification and Characterization of Oligosaccharides

Proteins in reaction mixture were removed by heating to 90° C. for 30 minutes and followed by centrifugation (5000 rpm, 20 min). The filtrate was then purified by C-18 gel chromatography and eluted by a gradient from 100% H$_2$O to 10% methanol in H$_2$O. The fractions were collected and monitored by TLC [butanol/ammonium hydroxide/water=5:3:2 (v/v/v)] and the fractions with allyl-oligosaccharides were pooled and lyophilized. More than 99% purity of product could be gathered by HPLC using Cosmosil SSL-II column in (H$_2$O/Acetonitrile=19/81) in an isocratic mode. The structure of allyl-Lac, allyl-Gb3, allyl-Gb4, allyl-Gb5, allyl-Globo H and allyl-SSEA4 were analyzed by $^1$H NMR, $^{13}$C NMR, and mass spectrometry (Avance 600 and APEX-ultra 9.4 T FTICR-MS, Bruker Daltonics).

Cloning of Genes for Nucleotide Sugar Synthesis, Glycosyltransferases and ATP Regeneration All genes obtained via PCR from genomic DNA or cDNA library by respective primer (Table 5), and PCR product were ligated into the modified pET47b vector. After ATG, following are the His-tag, AcTEV protease cutting site and ccdB positive selection gene flanked by special restriction recognition enzymes, or pET28a in C-terminal His-tag. In order to increase the gene expression level, the four glycosyltransferases were synthesized by codon optimization for *E. coli*. The plasmid with correct sequence was transformed into ArcticExpress/RIL competent cell by chemical transformation method. Picked single colony and inoculated into TB medium with kanamycin antibiotics overnight, and refresh the cell culture into fresh TB medium, then inducing target protein expression by final concentration 0.1 mM IPTG when OD600 was reaching 0.5. After that, allowed grown at 16° C. for 24 h. The *E. coli* cells were harvested and disrupted in a buffer containing 50 mM sodium phosphate buffer, pH8.0, 300 mM sodium chloride, and 10 mM imidazole by microfluidizer. Centrifuge the cell in 10,000 rpm at 4° C. for 30 minutes. Then, poured the supernatant into the equilibrated Ni-NTA agarose and discard the precipitate. The bound protein was eluted in the same buffer but containing higher concentration imidazole (250 mM). The protein concentration was determined by Qubit Protein Quantitation (Invitrogen, CA), and purity was confirmed by SDS-PAGE.

TABLE 5

Primers used for sialidase expressions in *E. coli*.

| SEQ ID NO | Primer$^a$ | Sequence (5'→3') | Restriction enzyme site | Gene source from genome or cDNA pool |
|---|---|---|---|---|
| SEQ ID NO: 1 | galK-F | CTGTATTTTCAGGGAGCGATCGCTATGAGTCTGAAAGAAAAAACA$^b$ | AsiSI | *E. coli* MG1655 |
| SEQ ID NO: 2 | galK-R | GCCTCGAGTCATTACGTTTAAACTCAGCACTGTCCTGCTCCTTG | PmeI | ATCC 700926 |
| SEQ ID NO: 3 | atusp-F | CTGTATTTTCAGGGAGCGATCGCTATGGCTTCTACGGTTGATTC | AsiSI | cDNA pool of *Arabidopsis thaliana* |
| SEQ ID NO: 4 | atusp-R | GCCTCGAGTCATTACGTTTAAACTCAATCTTCAACAGAAAATTTGC | PmeI | |

TABLE 5-continued

Primers used for sialidase expressions in E. coli.

| SEQ ID NO | Primer[a] | Sequence (5'→3') | Restriction enzyme site | Gene source from genome or cDNA pool |
|---|---|---|---|---|
| SEQ ID NO: 5 | lgtC-F[b] | GATATACCATGGAAATGGACATCGTTTTCGCGGCG | NcoI | Gene optimization |
| SEQ ID NO: 6 | lgtC-R[b] | GTGGTGCTCGAGGTAGATTTTACGCAGGAAACG | XhoI | |
| SEQ ID NO: 7 | nahK-F | CTGTATTTTCAGGGAGCGATCGCTATGAACAAGACTTATGATTTTAAAAG | AsiSI | Bifidobacterium longum |
| SEQ ID NO: 8 | nahK-R | GCCTCGAGTCATTACGTTTAAACTTAAATGTATGAATATACTATCTTC | PmeI | ATCC 15697 |
| SEQ ID NO: 9 | glmU-F | CTGTATTTTCAGGGAGCGATCGCTATGTTGAATAATGCTATGAGC | AsiSI | E. coli MG1655 |
| SEQ ID NO: 10 | glmU-R | GCCTCGAGTCATTACGTTTAAACTCACTTTTTCTTTACCGGACG | PmeI | ATCC 700926 |
| SEQ ID NO: 11 | lgtD-F[b] | GATATACCATGGAAAACTGCCCGCTGGTTTCT | NcoI | Gene optimization |
| SEQ ID NO: 12 | lgtD-R[b] | GTGGTGCTCGAGGAAGATAACGTTGATTTTACGG | XhoI | |
| SEQ ID NO: 13 | fkp -F | CAGGGAGCGATCGCTATGCAAAAACTACTATCTTTA | AsiSI | Bacteroides fragilis 9343 |
| SEQ ID NO: 14 | fkp-R | CATTACGTTTAAACTTATGATCGTGATACTTGGAA | PmeI | ATCC 25285 |
| SEQ ID NO: 15 | futC-F[b] | CTGTATTTTCAGGGAGCGATCGCTATGGCGTTCAAAGTTGTTCAG | AsiSI | Gene optimization |
| SEQ ID NO: 16 | futC-R[b] | GCCTCGAGTCATTACGTTTAAACTTACGCGTTGTATTTCTGAGAT | PmeI | |
| SEQ ID NO: 17 | cmk-F | CAGGGAGCGATCGCTATGACGGCAATTGCCCCGGTT | AsiSI | E. coli MG1655 |
| SEQ ID NO: 18 | cmk-R | CATTACGTTTAAACTTATGCGAGAGCCAATTTCTG | PmeI | ATCC 700926 |
| SEQ ID NO: 19 | CSS-F | GATATACCATGGAAACAAATATTGCGATCATTCCTG | NcoI | Pasteurella multocida |
| SEQ ID NO: 20 | CSS-R | GTGGTGCTCGAGTTTATTGGATAAAATTTCCGCGAG | XhoI | ATCC BAA-1113 |
| SEQ ID NO: 21 | jt-faj-16-F[b] | GATATACCATGGAAATGAACAACGACAACTCTACC | NcoI | Gene optimization |
| SEQ ID NO: 22 | jt-faj-16-R[b] | GTGGTGCTCGAGGATGTCAGAGATCAGTTTGATG | XhoI | |
| SEQ ID NO: 23 | pykF-F | CTGTATTTTCAGGGAGCGATCGCTATGAAAAAGACCAAAATTGTTTG | AsiSI | E. coli MG1655 |
| SEQ ID NO: 24 | pykF-R | GCCTCGAGTCATTACGTTTAAACTTACAGGACGTGAACAGATG | PmeI | ATCC 700926 |
| SEQ ID NO: 25 | ppa-F | CAGGGAGCGATCGCTATGAGCTTACTCAACGTCCCT | AsiSI | E. coli MG1655 |
| SEQ ID NO: 26 | ppa-R | CATTACGTTTAAACTTATTTATTCTTTGCGCGCTC | PmeI | ATCC 700926 |

[a] a pair of primers for forward (F) and reversed (R) PCR reactions to amplify the coding sequence of each gene.
[b] Underline with bold means the site of restriction enzyme recognition.
[c] Codon optimization for E. coli. See e.g., Puigbò et al., Nucleic Acids Research (2007) 35(S2): W126-W130.

Enzyme Assay

In order to maintain constant assay conditions, all activity was measured at 37° C. with 10 mM MgCl$_2$, 100 mM Tris, and at a pH of 7.5.

(i) Measurement of the Galactokinase (GalK), N-Acetylhexosamine Kinase (NahK), Fucokinase (FKP) and Cytidine Monophosphate Kinase (CMK) Activity The fluorometric assay method was based on monitor of ADP production (ATP consumption) by using the pyruvate kinase/lactate dehydrogenase coupled enzymatic assay for the NADH consumption. See, e.g., Murray et al., "Mechanism of Human α-1,3-Fucosyltransferase V: Glycosidic Cleavage Occurs Prior to Nucleophilic Attack" *Biochemistry* (1997) 36:823-831; and Gosselin et al., "A Continuous Spectrophotometric Assay for Glycosyltransferases" *Analytical Biochemistry* (1994) 220:92-97. Fluorescence property of NADH has an excitation wavelength of 340 nm and an emission wavelength of 450 nm. A 100 uL of reaction mixture was prepared containing the coupling enzyme (5 units of pyruvate kinase and 7 units of lactic dehydrogenase from rabbit muscle) and substrates and cofactors (0.2 mM NADH, 0.8 mM PEP, 10 mM MgCl$_2$) in 100 mM Tris (pH 7.5). Reactions were initiated by the addition of the respective sugar. The kinetic parameters, $K_{cat}$ and $K_m$ were calculated by curve fitting the experimental data with the theoretical equation, using Grafit version 7 (Erithacus Software, Middlesex, UK). One unit of sugar kinase activity is defined as 1 umol of sugar-1-P formation per minute at 25° C.

(ii) Measurement of UDP-Sugar Pyrophosphorylase (AtUSP), N-Acetyl Glucosamine-1-Phosphate Uridyltransferase (GlmU), GDP-L-Fucose Pyrophosphorylase (FKP) and CMP-Sialic Acid Synthetases (CSS) Activity The production of pyrophosphate was measured using the EnzCheck Pyrophosphate Assay Kit (Invitrogen, CA, USA). Assay components including: 200 uM 2-amino-6-mercapto-7-methylpurine ribonucleoside, 1 unit nucleoside phosphorylase, 0.03 unit inorganic pyrophosphatase, 10 mM MgCl$_2$, 50 mM Tris, pH 7.5 in 100 uL scale in UV-Star microplates (Greiner Bio One, Germany). All components except FKP were mixed in the microplates and allowed to equilibrate until a flat baseline was achieved. Reactions were initiated by the addition of enzyme. One unit of enzyme activity is defined as the producing 1 umol of nucleotide sugar from the respective sugar-1-Ps per minute at 25° C., except for CMP-sialic acid synthetase, which is defined as 1 umol of pyrophosphate formation per minute at 25° C.

(iii) Measurement of Glycosyltransferase: α-1,4-Galactosyltransferase(LgtC), β1,3-N-Acetylgalactosaminyltransferase (β1,3GalNAcT, LgtD), β-1,3-Galactosyltransferase (LgtD), α-1,2-Fucosyltransferase (FutC) and α-2,3-Sialyltransferase (JT-FAJ-16).

The fluorometric assay method monitored UDP, GDP, or CDP production using the pyruvate kinase/lactate dehydrogenase coupled enzymatic assay for the NADH consumption. See, e.g., Murray et al., "Mechanism of Human α-1,3-Fucosyltransferase V: Glycosidic Cleavage Occurs Prior to Nucleophilic Attack" *Biochemistry* (1997) 36:823-831; and Gosselin et al., "A Continuous Spectrophotometric Assay for Glycosyltransferases" *Analytical Biochemistry* (1994) 220: 92-97. The assay components except nucleotide sugar were simultaneously incubated in the multiple plate fluorometer (SpectraMax M2 Readers, Molecular Devices) at 25° C. Reactions were initiated by the addition of corresponding nucleotide sugar. The kinetic parameters, $K_{cat}$ and $K_m$ were calculated by curve fitting the experimental data with the theoretical equation, using Grafit version 7 (Erithacus Software, Middlesex, UK). One unit of activity is defined as the amount of enzyme that catalyzes the transfer 1umol sugar from respective nucleotide sugar to acceptor per minute at 25° C.

(iv) Measurement of Pyruvate Kinase (PyrK)

Pyruvate kinase assay was slightly modified from sugar kinase measurement previous mentioned, also based on NADH consumption. A 100 uL of reaction mixture is prepared containing 0.8 mM ADP, 0.8 mM PEP, 0.2 mM NADH, 10 mM MgCl$_2$, and 5 units of lactic dehydrogenase from rabbit muscle in 100 mM Tris (pH 7.5) in black multiplate. NADH has an excitation wavelength at 340 nm and an emission wavelength at 450 nm. Reaction is initiated by adding a suitable amount of recombinant *E. coli* pyruvate kinase. One unit of pyruvate kinase is defined as conversion of 1.0 µmole of phospho(enol)pyruvate to pyruvate per minute at 25° C.

(v) Measurement of Pyrophosphatase (PPA)

Pyrophosphatase assay is slightly modified from pyrophorylase protocol from commercial kit EnzCheck Pyrophosphate Assay Kit (Invitrogen, CA, USA). Assay components including: 1 mM pyrophosphate, 200 uM 2-amino-6-mercapto-7-methylpurine ribonucleoside, 1 unit nucleoside phosphorylase, 10 mM MgCl$_2$, 50 mM Tris, at a pH of 7.5 in 100 uL scale in UV-Star microplates (Greiner Bio One, Germany) with suitable amount of recombinant *E. coli* pyrophosphatase. One unit of pyrophosphatase activity is defined as liberation of 1.0 umole of inorganic pyrophosphate per minute at 25° C.

(vi) Measurement of Optimum pH

The optimum pH for enzyme activity was determined in the standard enzyme assay mentioned above in the pH range 4.0-10.0, including sodium acetate, MES, MOPS, HEPES, Tris-HCl, CHES buffer. The pH of the buffer was adjusted at the temperature of incubation. All reactions were performed in triplicate for statistical evaluation.

(vii) Measurement of Optimum Divalent Metal Ion

The assay for metal requirement was conducted in standard assay condition. Enzymes were mixed with metal ion ($Mg^{2+}$, $Mn^{2+}$, $Mg^{2+}+Mn^{2+}$, $Ca^{2+}$, $Zn^{2+}$, $Co^{2+}$, or $Ni^{2+}$) in a final concentration of 10 mM, in the presence and absence of EDTA. All reactions were performed in triplicate for statistical evaluation.

(viii) Measurement of Optimum Temperature

The effect of temperature on the activity of enzymes were determined by incubating an appropriate amount of purified enzyme in MOPS buffer (pH 7.0), 10 mM MgCl$_2$ and respective substrates. In order to keep the assay consist, all components were mixed well and preheated at assay temperature for 5 min, and the reaction was started by adding the enzyme and recorded by multimode plate readers (SpectraMax M5, Molecular Devices) in constant temperature. The temperature ranged from 20 to 60° C. All reactions were performed in triplicate for statistical evaluation.

Enzyme Composition

UDP-Gal Regeneration/Galactosylation

1. GalK: galactokinase, from *E. coli*
2. AtUSP: UDP-sugar pyrophosphorylase from *Arabidopsis thaliana*
3. LgtC: α1,4galactsyltransferase, from *Neisseria meningitidis*, but codon optimization for *E. coli*
4. PykF: pyruvate kinase, from *E. coli*
5. PPA: pyrophosphatase, from *E. coli*

The coding sequence of the coden-optimized LgtC enzyme is provided below (SEQ ID NO: 27):

```
ATGGACATCGTTTTCGCGGCGGACGACAACTACGCGGCGTACCTGTGCGTTGCGGCGAAATC
TGTTGAAGCGGCGCACCCGGACACCGAAATCCGTTTCCACGTTCTGGACGCGGGTATCTCTG
AAGCGAACCGTGCGGCGGTTGCGGCGAACCTGCGTGGTGGTGGTGGTAACATCCGTTTCATC
GACGTTAACCCGGAAGACTTCGCGGGTTTCCCGCTGAACATCCGTCACATCTCTATCACCAC
CTACGCGCGTCTGAAACTGGGTGAATACATCGCGGACTGCGACAAAGTTCTGTACCTGGACA
TCGACGTTCTGGTTCGTGACTCTCTGACCCCGCTGTGGGACACCGACCTGGGTGACAACTGG
CTGGGTGCGTGCATCGACCTGTTCGTTGAACGTCAGGAAGGTTACAAACAGAAAATCGGTAT
GGCGGACGGTGAATACTACTTCAACGCGGGTGTTCTGCTGATCAACCTGAAAAAATGGCGTC
GTCACGACATCTTCAAAATGTCTTGCGAATGGGTTGAACAGTACAAAGACGTTATGCAGTAC
CAGGACCAGGACATCCTGAACGGTCTGTTCAAAGGTGGTGTTTGCTACGCGAACTCTCGTTT
CAACTTCATGCCGACCAACTACGCGTTCATGGCGAACCGTTTCGCGTCTCGTCACACCGACC
CGCTGTACCGTGACCGTACCAACACCGTTATGCCGGTTGCGGTTTCTCACTACTGCGGTCCG
GCGAAACCGTGGCACCGTGACTGCACCGCGTGGGGTGCGGAACGTTTCACCGAACTGGCGGG
TTCTCTGACCACCGTTCCGGAAGAATGGCGTGGTAAACTGGCGGTTCCGCACCGTATGTTCT
CTACCAAACGTATGCTGCAGCGTTGGCGTCGTAAACTGTCTGCGCGTTTCCTGCGTAAAATC
TACTGA
```

UDP-GalNAc Regeneration/Acetylgalactosamination

1. GalNAcK: N-Acetylhexosamine 1-Kinases, from *B. longum*
2. GlmU: N-acetylglucosamine 1-phosphate uridylyltransferase from *E. coli*
3. LgtD: β1,3galactosyltransferase, from *Haemophilus influenza*, but codon optimization for *E. coli*
4. PykF: pyruvate kinase, from *E. coli*
5. PPA: pyrophosphatase, from *E. coli*

The coding sequence of the coden-optimized LgtD enzyme is provided below (SEQ ID NO: 28):

GDP-FKP Regeneration/Fucosylation

1. FKP: L-fucokinase/GDP-fucose pyrophosphorylase, from *Bacteroides fragilis*
2. FutC: α1,2fucosyltransferase, from *Helicobacter pylori*, but codon optimization for *E. coli*
3. PykF: pyruvate kinase, from *E. coli*
4. PPA: pyrophosphatase, from *E. coli*

The coding sequence of the coden-optimized FutC enzyme is provided below (SEQ ID NO: 29):

```
ATGGAAAACTGCCCGCTGGTTTCTGTTATCGTTTGCGCGTACAACGCGGAACAGTACATCGACGAATCTA
TCTCTTCTATCATCAACCAGACCTACGAAAACCTGGAAATCATCGTTATCAACGACGGTTCTACCGACCT
GACCCTGTCTCACCTGGAAGAAATCTCTAAACTGGACAAACGTATCAAAATCATCTCTAACAAATACAAC
CTGGGTTTCATCAACTCTCTGAACATCGGTCTGGGTTGCTTCTCTGGTAAATACTTCGCGCGTATGGACG
CGGACGACATCGCGAAACCGTCTTGGATCGAAAAAATCGTTACCTACCTGGAAAAAAACGACCACATCAC
CGCGATGGGTTCTTACCTGGAAATCATCGTTGAAAAGAATGCGGTATCATCGGTTCTCAGTACAAAACC
GGTGACATCTGGAAAAACCCGCTGCTGCACAACGACATCTGCGAAGCGATGCTGTTCTACAACCCGATCC
ACAACAACACCATGATCATGCGTGCGAACGTTTACCGTGAACACAAACTGATCTTCAACAAAGACTACCC
GTACGCGGAAGACTACAAATTCTGGTCTGAAGTTTCTCGTCTGGGTTGCCTGGCGAACTACCCGGAAGCG
CTGGTTAAATACCGTCTGCACGGTAACCAGACCTCTTCTGTTTACAACCACGAACAGAACGAAACCGCGA
AAAAAATCAAACGTGAAAACATCACCTACTACCTGAACAAAATCGGTATCGACATCAAAGTTATCAACTC
TGTTTCTCTGCTGGAAATCTACCACGTTGACAAATCTAACAAAGTTCTGAAATCTATCCTGTACGAAATG
TACATGTCTCTGGACAAATACACCATCACCTCTCTGCTGCACTTCATCAAATACCACCTGGAACTGTTCG
ACCTGAAACAGAACCTGAAAATCATCAAAAAATTCATCCGTAAAATCAACGTTATCTTCTAG
```

```
ATGGCGTTCAAAGTTGTTCAGATCTGCGGTGGTCTGGGTAACCAGATGTTCCAGTACGCGTTCGCGAAAT
CTCTGCAGAAACACTCTAACACCCCGGTTCTGCTGGACATCACCTCTTTCGACTGGTCTGACCGTAAAT
GCAGCTGGAACTGTTCCCGATCGACCTGCCGTACGCGTCTGCGAAAGAAATCGCGATCGCGAAATGCAG
CACCTGCCGAAACTGGTTCGTGACGCGCTGAAATGCATGGGTTTCGACCGTGTTTCTCAGGAAATCGTTT
TCGAATACGAACCGAAACTGCTGAAACCGTCTCGTCTGACCTACTTCTTCGGTTACTTCCAGGACCCGCG
TTACTTCGACGCGATCTCTCCGCTGATCAAACAGACCTTCACCCTGCCGCCGCCGCCGGAAAACAACAAA
AACAACAACAAAAAGAAGAAGAATACCAGTGCAAACTGTCTCTGATCCTGGCGGCGAAAAACTCTGTTT
TCGTTCACATCCGTCGTGGTGACTACGTTGGTATCGGTTGCCAGCTGGGTATCGACTACCAGAAAAAAGC
GCTGGAATACATGGCGAAACGTGTTCCGAACATGGAACTGTTCGTTTTCTGCGAAGACCTGGAATTCACC
CAGAACCTGGACCTGGGTTACCCGTTCATGGACATGACCACCCGTGACAAAGAAGAAGAAGCGTACTGGG
ACATGCTGCTGATGCAGTCTTGCCAGCACGGTATCATCGCGAACTCTACCTACTCTTGGTGGGCGGCGTA
CCTGATCGAAACCCGGAAAAAATCATCATCGGTCCGAAACACTGGCTGTTCGGTCACGAAAACATCCTG
TGCAAAGAATGGGTTAAAATCGAATCTCACTTCGAAGTTAAATCTCAGAAATACAACGCGTAA
```

CMP-Neu5Ac Regeneration/Sialylation
1. CMK: Cytidine monophosphate kinase, from *E. coli*
2. Css: CMP-sialic acid synthetase, from *Pasteurella multocida*
3. JT-FAJ-16: α2,3sialyltransferase, from marine bacteria, but codon optimization for *E. coli*
4. PykF: pyruvate kinase, from *E. coli*
5. PPA: pyrophosphatase, from *E. coli*

The coding sequence of the coden-optimized JT-FAJ-16 enzyme is provided below (SEQ ID NO: 30):

```
ATGAACAACGACAACTCTACCACCACCAACAACAACGCGATCGAAATCTACGTTGACCGTGCGACCCTGC
CGACCATCCAGCAGATGACCAAAATCGTTTCTCAGAAAACCTCTAACAAAAAACTGATCTCTTGGTCTCG
TTACCCGATCACCGACAAATCTCTGCTGAAAAAAATCAACGCGGAATTCTTCAAAGAACAGTTCGAACTG
ACCGAATCTCTGAAAAACATCATCCTGTCTGAAAACATCGACAACCTGATCATCCACGGTAACACCCTGT
GGTCTATCGACGTTGTTGACATCATCAAAGAAGTTAACCTGCTGGGTAAAAACATCCCGATCGAACTGCA
CTTCTACGACGACGGTTCTGCGGAATACGTTCGTATCTACGAATTCTCTAAACTGCCGGAATCTGAACAG
AAATACAAAACCTCTCTGTCTAAAAACAACATCAAATTCTCTATCGACGGTACCGACTCTTTCAAAAACA
CCATCGAAAACATCTACGGTTTCTCTCAGCTGTACCCGACCACCTACCACATGCTGCGTGCGGACATCTT
CGACACCACCCTGAAATCAACCCGCTGCGTGAACTGCTGTCTAACAACATCAAACAGATGAAATGGGAC
TACTTCAAAGACTTCAACTACAAACAGAAAGACATCTTCTACTCTCTGACCAACTTCAACCCGAAAGAAA
TCCAGGAAGACTTCAACAAAAACTCTAACAAAAACTTCATCTTCATCGGTTCTAACTCTGCGACCGCGAC
CGCGGAAGAACAGATCAACATCATCTCTGAAGCGAAAAAAGAAAACTCTTCTATCATCACCAACTCTATC
TCTGACTACGACCTGTTCTTCAAAGGTCACCCGTCTGCGACCTTCAACGAACAGATCATCAACGCGCACG
ACATGATCGAAATCAACAACAAAATCCCGTTCGAAGCGCTGATCATGACCGGTATCCTGCCGGACGCGGT
TGGTGGTATGGGTTCTTCTGTTTTCTTCTCTATCCCGAAAGAAGTTAAAAACAAATTCGTTTTCTACAAA
TCTGGTACCGACATCGAAAACAACTCTCTGATCCAGGTTATGCTGAAACTGAACCTGATCAACCGTGACA
ACATCAAACTGATCTCTGACATCTAA
```

Materials and Chemicals

All nucleotide, sugar, nucleotide sugar and chemicals were purchased from Sigma-Aldrich (St. Louis, Mo.). Restriction enzyme and T4 DNA ligase acquired from NEB (Beverly, Mass.). Primer ordered from Proligo Singapore Pte Ltd (Singapore). Ni-NTA Agarose obtained from Qiagen (Santa Clarita, Calif.). Bio-Gel P2 gel was purchase from Bio-Rad (Hercules, Calif.). Plasmid pET28a, pET47b and precoated glass plates TLC covered in Silica Gel 60, F254 with 0.25 mm layer thickness was purchase from EMD Chemicals Inc (Carlsbad, Calif.) were purchased from EMD Chemicals Inc (Carlsbad, Calif.). ArcticExpress/RIL competent cell were obtained from Agilent Genomics (La Jolla, Calif.). All other materials not mentioned above were purchased as high quality as possible.

All reactions were monitored by thin-layer chromatography. (mobile phase: Butanol:acetate:water=5:3:2). Staining the TLC by p-Anisaldehyde.

Synthesis of Allyl-Lac

The synthesis of different lactose with linker was followed by the literature reported method [Carbohydrate Research 2004, 339, 2415-2424.]. $^1$H NMR (600 MHz, D2O) δ 6.01 (m, 1H), 5.40-5.37 (dd, J=17.3, 1.4 Hz, 1H), 5.30-5.28 (d, J=10.3 Hz, 1H), 4.54 (d, J=8.1 Hz, 1H), 4.46 (d, J=7.8 Hz, 1H), 4.41-4.38 (m, 1H), 4.25-4.22 (m, 1H), 4.00-3.97 (dd, J=12.3, 2.1 Hz, 1H), 3.93 (d, J=3.3 Hz, 1H), 3.80-3.71 (m, 4H), 3.67-3.53 (m, 5H), 3.35-3.33 (m, 1H); $^{13}$C NMR (150 MHz, D2O) δ 133.3, 118.7, 102.9, 101.0, 78.3, 75.3, 74.7, 74.4, 72.8, 72.5, 70.9, 70.6, 68.5, 60.9, 60.1; HRMS (ESI-TOF, MNa$^+$) $C_{15}H_{26}O_{11}Na^+$ calcd for 405.1367. found 405.1346.

Large Scale Production of Gb3 with Linker 5 mmol lactose with linker, 5 mmol galactose, 12 mmol Phosphoenolpyruvic acid (PEP), 0.25 mmol ATP, 0.25 mmol UTP and 10 mM MgCl$_2$ were added into 100 mM Tris-HCl buffer (pH 7.5) solution. The reaction was initiated by addition suitable amount of α-1,4-galactosyltransferase (LgtC), galactokinase (GalK), UDP-sugar pyrophosphorylase (AtUSP), pyruvate kinase (PK) and pyrophosphatase (PPA). The flask was placed into an incubator at 16~50° C. with gentle shaking. The reaction was monitored by TLC. More enzymes are added if the reaction stops. The reaction is stopped when no more starting material is observed by TLC. The Gb3 product was isolated by $^{18}$C reverse phase column in 99% yield.

Allyl-Gb3: $^1$H NMR (600 MHz, D2O) δ 6.00 (m, 1H), 5.42 (d, J=17.2 Hz, 1H), 5.32 (d, J=10.4 Hz, 1H), 4.97 (d, J=3.3 Hz, 1H), 4.56 (d, J=7.9 Hz, 1H), 4.53 (d, J=7.7 Hz, 1H), 4.43-4.37 (m, 2H), 4.27-4.24 (m, 1H), 4.06-3.58 (m, 16H), 3.37-3.34 (t, J=8.0 Hz, 1H); $^{13}$C NMR (150 MHz, D2O) δ 133.3, 118.7, 103.3, 100.9, 100.3, 78.6, 77.3, 75.4, 74.8, 74.5, 72.9, 72.2, 70.9, 70.8, 70.6, 69.1, 68.9, 68.5, 60.5, 60.4, 60.0; HRMS (ESI-TOF, MNa$^+$) $C_{21}H_{36}O_{16}Na^+$ calcd for 567.1896. found 567.1858.

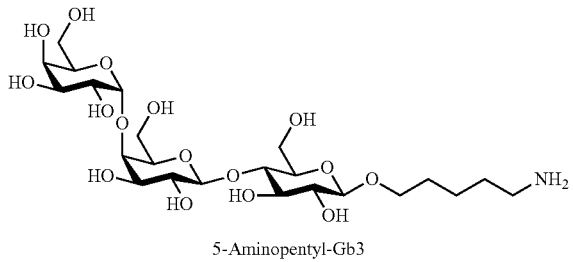

5-Aminopentyl-Gb3

$^1$H NMR (600 MHz, D2O) δ 4.97 (d, J=3.3 Hz, 1H), 4.56 (d, J=7.9 Hz, 1H), 4.54-4.50 (m, 2H), 4.37 (dd, J=6.0 Hz, J=0.6 Hz, 1H), 4.27-4.24 (m, 1H), 4.06-3.59 (m, 18H), 3.35 (t, J=8.0 Hz, 1H), 3.03 (t, J=7.4 Hz, 2H), 1.75-1.68 (m, 4H), 1.51-1.46 (m, 2H); $^{13}$C NMR (150 MHz, D2O) δ 103.3, 101.9, 100.3, 78.7, 77.3, 75.4, 74.8, 74.5, 72.9, 72.2, 70.9, 70.8, 70.6, 69.1, 68.9, 68.5, 60.5, 60.4, 60.0, 39.3, 28.1, 26.4, 22.1.

Large Scale Production of Gb4 with Linker 5 mmol Gb3 with linker, 5 mmol N-acetylgalactosamine (GalNAc), 12 mmol Phosphoenolpyruvic acid (PEP), 0.25 mmol ATP, 0.25 mmol UTP and 10 mM MgCl$_2$ were added into 100 mM Tris-HCl buffer (pH 7.5) solution. The reaction was initiated by addition suitable amount of β-1,3-N-acetylgalactosaminetransferase (LgtD), N-acetylhexosamine 1-kinase (NahK), N-acetylglucosamine 1-phosphate uridylyltransferase (GlmU), pyruvate kinase (PK) and pyrophosphatase (PPA). The flask was placed into an incubator at 16~50° C. with gentle shaking. The reaction was monitored by TLC. More enzymes are added if the reaction stops. The reaction is stopped when no more starting material is observed by TLC. The Gb4 product was isolated by $^{18}$C reverse phase column in 96% yield.

Allyl-Gb4: $^1$H NMR (600 MHz, D2O) δ 6.01 (m, 1H), 5.40-5.38 (dd, J=17.3, 1.4 Hz, 1H), 5.30 (d, J=10.5 Hz, 1H), 4.92 (d, J=3.9 Hz, 1H), 4.64 (d, J=8.5 Hz, 1H), 4.54 (d, J=7.9 Hz, 1H), 4.53 (d, J=7.8 Hz, 1H), 4.42-4.38 (m, 2H), 4.26-4.22 (m, 2H), 4.05 (d, J=2.9 Hz, 1H), 4.01-3.99 (dd, J=12.3, 1.8 Hz, 1H), 3.98-3.89 (m, 5H), 3.86-3.74 (m, 7H), 3.72-3.57 (m, 7H), 3.37-3.34 (t, J=8.6 Hz, 1H), 2.05 (s, 3H); $^{13}$C NMR (150 MHz, D2O) δ 133.2, 118.7, 103.3, 103.2, 100.9, 100.4, 78.7, 78.6, 77.2, 75.4, 74.9, 74.8, 74.5, 72.9, 72.1, 70.9, 70.8, 70.6, 70.2, 68.9, 67.7, 67.6, 60.9, 60.5, 60.3, 60.2, 60.0, 52.6, 22.2; HRMS (MALDI, MNa$^+$) $C_{29}H_{49}NO_{21}Na^+$ calcd for 770.2689. found 770.2654.

Large Scale Production of Gb5 with Linker 5 mmol allyl-Gb4, 5 mmol galactose, 12 mmol Phosphoenolpyruvic acid (PEP), 0.25 mmol ATP, 0.25 mmol UTP with 10 mM MgCl$_2$ were added into 100 mM Tris-HCl buffer (pH 7.5). The reaction was initiated by addition suitable amount of β-1,3-galactosyltransferase, galactokinase (GalK), UDP-sugar pyrophosphorylase (AtUSP), pyruvate kinase (PK) and pyrophosphatase (PPA). The flask was placed into an incubator at 16~50° C. with gentle shaking. The reaction was monitored by TLC. More enzymes are added if the reaction stops. The reaction is stopped when no more starting material is observed by TLC. The Gb5 product was purified by $^{18}$C reverse phase column in 95% yield.

Allyl-Gb5: $^1$H NMR (600 MHz, D2O) δ 6.01 (m, 1H), 5.41-5.38 (dd, J=17.3, 1.4 Hz, 1H), 5.31 (d, J=10.6 Hz, 1H), 4.93 (d, J=4.0 Hz, 1H), 4.71 (d, J=8.5 Hz, 1H), 4.55 (d, J=8.1 Hz, 1H), 4.53 (d, J=7.8 Hz, 1H), 4.47 (d, J=7.7 Hz, 1H), 4.42-4.39 (m, 2H), 4.27-4.23 (m, 2H), 4.20 (d, J=3.2 Hz, 1H), 4.09-3.90 (m, 8H), 3.87-3.59 (m, 17H), 3.55-3.52 (m, 1H), 3.36-3.33 (t, J=8.6 Hz, 1H), 2.04 (s, 3H); $^{13}$C NMR (150 MHz, D2O) δ 175.1, 133.2, 118.7, 104.8, 103.3, 102.9, 100.9, 100.4, 79.6, 78.7, 78.6, 77.2, 75.4, 74.9, 74.8, 74.6, 74.5, 72.9, 72.4, 72.1, 70.9, 70.6 (2C), 70.2, 68.9, 68.5, 67.9, 67.6, 60.9 (2C), 60.33, 60.28, 60.0, 51.5, 22.2; HRMS (ESI-TOF, MNa$^+$) $C_{35}H_{59}NO_{26}Na^+$ calcd for 932.3218. found 932.3235.

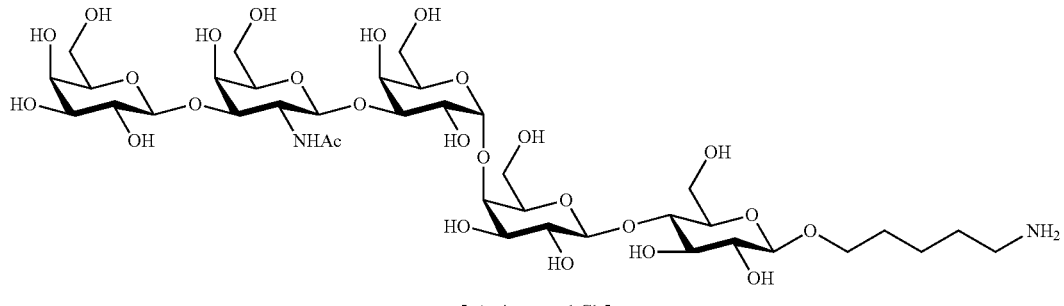

5-Aminopentyl-Gb5

$^1$H NMR (600 MHz, D$_2$O), 4.47 (d, 1H, J=8.42 Hz), 4.30 (d, 1H, J=7.9 Hz), 4.28 (d, 1H, J=8.1 Hz), 4.24 (d, 1H, J=7.7 Hz), 4.19 (t, 1H J=7.0 Hz), 4.04 (d, 1H, J=2.8 Hz), 3.97 (d, 1H, J=2.98 Hz), 3.87-3.35 (m, 32H), 3.30 (t, 1H, J=7.7 Hz), 3.09 (t, 1H, J=8.5 Hz), 2.79 (t, 2H, J=7.6 Hz), 1.82 (s, 3H), 1.51-1.43, (m, 4H), 1.28-1.21 (m, 2H) $^{13}$C NMR (150 MHz, D$_2$O), δ 175.0, 104.7, 103.1, 102.8, 101.8, 100.2, 79.4, 78.5, 78.4, 76.9, 75.3, 74.8, 74.7, 74.4, 74.3, 72.8, 72.2, 71.9, 70.6, 70.4, 70.0, 69.9, 68.7, 68.4, 67.8, 67.4, 60.82, 60.77, 60.13, 60.1, 59.8, 51.3, 39.1, 28.0, 26.3, 22.1, 21.9 MALDI-TOF: C$_{37}$H$_{66}$N$_2$O$_{26}$ [M+H]$^+$ calculated 955.3904. found 955.3972.

Large Scale Production of Globo H with Linker 5 mmol Gb5 with linker, 5 mmol fucose, 12 mmol Phosphoenolpyruvic acid (PEP), 0.25 mmol ATP, 0.25 mmol GTP with 10 mM MgCl$_2$ were added into 100 mM Tris-HCl buffer (pH 7.5). The reaction was initiated by addition suitable amount of α-1,2-fucosyltransferase, L-fucokinase/GDP-fucose pyrophosphorylase (FKP), pyruvate kinase (PK) and pyrophosphatase (PPA). The flask was placed into an incubator at 16~50° C. with gentle shaking. The reaction was monitored by TLC. More enzymes are added if the reaction stops. The reaction is stopped when no more starting material is observed by TLC. The Globo H product was purified by $^{18}$C reverse phase column in 94% yield.

Allyl-Globo H: $^1$H NMR (600 MHz, D$_2$O) δ 6.01 (m, 1H), 5.41-5.38 (dd, J=17.3, 1.4 Hz, 1H), 5.31 (d, J=10.7 Hz, 1H), 5.24 (d, J=4.0 Hz, 1H), 4.91 (d, J=3.9 Hz, 1H), 4.63 (d, J=7.7 Hz, 1H), 4.56-4.52 (m, 3H), 4.42-4.40 (m, 2H), 4.26-4.23 (m, 3H), 4.12 (d, J=2.2 Hz, 1H), 4.05 (d, J=3.0 Hz, 1H), 4.03-3.59 (m, 28H), 3.36-3.33 (t, J=8.2 Hz, 1H), 2.06 (s, 3H), 1.24 (d, J=6.5 Hz, 3H); $^{13}$C NMR (150 MHz, D2O) δ 174.3, 133.2, 118.7, 103.9, 103.2, 102.0, 100.9, 100.4, 99.3, 78.7, 78.3, 77.1, 76.3, 76.1, 75.5, 75.0, 74.8, 74.6, 74.5, 73.5, 72.9, 72.1, 71.8, 70.8, 70.6, 70.1, 69.5, 69.2, 69.1, 68.5, 68.0, 67.8, 66.8, 60.95, 60.93, 60.3 (2C), 60.0, 51.6, 22.2, 15.3; HRMS (MALDI, MNa+) C$_{41}$H$_{70}$NO$_{30}$Na$^+$ calcd for 1079.3875. found 1078.4145.

$^1$H NMR (600 MHz, D$_2$O) δ 5.12 (d, 1H, J=3.9 Hz), 4.78 (d, 1H, J=3.6 Hz), 4.50 (d, 1H, J=7.7 Hz), 4.43 (d, 1H, J=7.5 Hz), 4.40 (d, 1H, J=7.7 Hz), 4.37 (d, 1H, J=8.0 Hz), 4.30 (t, 1H, J=6.2 Hz), 4.15-4.10 (m, 2H), 3.99 (d, 1H, J=1.8 Hz), 3.92 (d, 1H, J=2.2 Hz), 3.90-3.47 (m, 33H), 3.19 (t, 1H, J=8.3 Hz), 2.89 (t, 2H, J=7.5 Hz), 1.94 (s, 3H), 1.60-1.55 (m, 4H), 1.38-1.31 (m, 2H), 1.11 (d, 3H, J=6.4 Hz). $^{13}$C NMR (150 MHz, D$_2$O) δ 176.1, 105.7, 105.0, 103.74, 103.65, 102.1, 100.97, 80.5, 79.9, 78.8, 78.0, 77.8, 77.2, 76.76, 76.5, 76.3, 76.2, 75.3, 74.6, 73.8, 73.5, 72.5, 71.81, 71.78, 71.2, 71.1, 70.9, 70.8, 70.2, 69.7, 69.5, 68.5, 62.66, 62.64, 62.0, 61.7, 53.3, 41.0, 29.9, 28.1, 23.9, 23.8, 17.0 MALDI-TOF: C$_{43}$H$_{76}$N$_2$O$_{30}$ [M+Na]$^+$ calculated 1123.4381. found 1123.4385.

Large Scale Production of SSEA4 with Linker 5 mmol Gb5 with linker, 5 mmol fucose, 12 mmol phosphoenolpyruvic acid (PEP), 0.25 mmol ATP, 0.25 mmol CTP with 10 mM MgCl$_2$ were added into 100 mM Tris-HCl buffer (pH 7.5). The reaction was initiated by addition suitable amount of α-2,3-sialyltransferase, cytidine monophosphate kinase (CMK), CMP-sialic acid synthetase (CSS), pyruvate kinase (PK) and pyrophosphatase (PPA). The flask was placed into an incubator at 16~50° C. with gentle shaking. The reaction was monitored by TLC. More enzymes are added if the reaction stops. The reaction is stopped when no more starting material is observed by TLC. The SSEA4 product was isolated by $^{18}$C reverse phase column in 45% yield.

Allyl-SSEA$_4$: $^1$H NMR (600 MHz, D$_2$O) δ 6.00 (m, 1H), 5.40-5.37 (d, J=17.3 Hz, 1H), 5.30-5.28 (d, J=10.4 Hz, 1H), 4.92 (d, J=3.9 Hz, 1H), 4.70 (d, J=8.5 Hz, 1H), 4.54-4.51 (m, 3H), 4.40-4.38 (m, 2H), 4.25-4.18 (m, 3H), 4.10-3.52 (m, 34H), 3.35-3.32 (t, J=8.6 Hz, 1H), 2.77 (dd, J=12.5, 4.6 Hz, 1H), 2.03 (s, 6H), 1.80 (t, J=12.1 Hz, 1H); $^{13}$C NMR (150 MHz, D2O) δ 175.2, 175.1, 174.1, 133.4, 121.6, 118.9, 104.7, 103.4, 103.1, 101.1, 100.5, 99.8, 79.9, 78.9, 78.8, 77.3, 75.7, 75.5, 75.0, 74.7, 74.6, 73.0, 72.9, 72.2, 72.1, 71.9, 71.0, 70.8, 70.4, 69.1, 69.0, 68.5, 68.2, 68.0, 67.7, 67.5, 62.6, 61.1, 60.5, 60.4, 60.1, 51.7, 51.4, 39.8, 22.4, 22.1; HRMS (ESI-TOF, M−H) C$_{46}$H$_{75}$N$_2$O$_{34}$ calcd for 1199.4196. found 1199.4208.

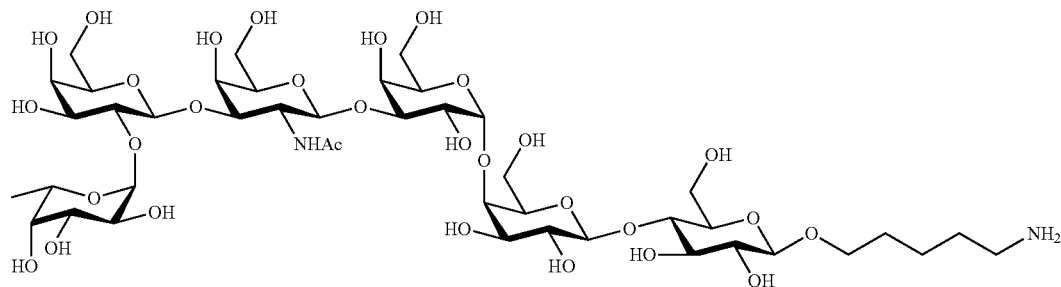

5-Aminopentyl-Globo H

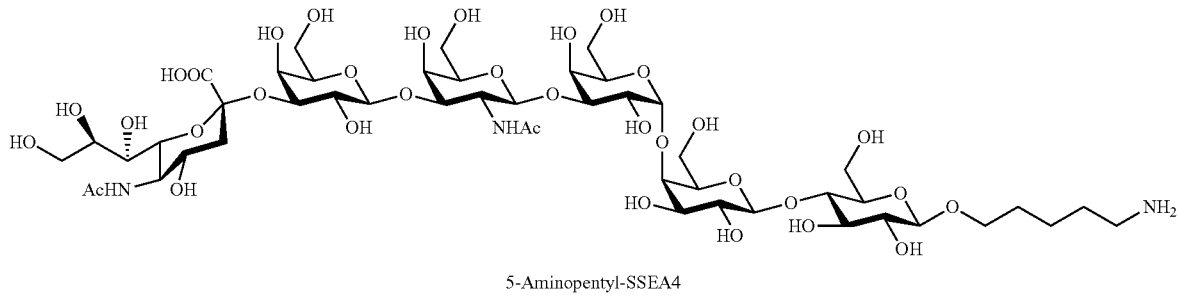

5-Aminopentyl-SSEA4

$^1$H NMR (600 MHz, D$_2$O) δ 4.94 (d, J=3.8 Hz, 1H), 4.72 (d, J=8.5 Hz, 1H), 4.54-4.50 (m, 3H), 4.40 (t, J=6.4 Hz, 1H), 4.27 (d, J=2.0 Hz, 1H), 4.20 (d, J=2.8 Hz, 1H), 4.10-3.54 (m, 37H), 3.34-3.31 (m, 1H), 3.02 (t, J=7.6 Hz, 2H), 2.78 (dd, J=12.4, 4.6 Hz, 1H), 2.05 (m, 6H), 1.80 (t, 12.2 Hz, 1H), 1.74-1.67 (m, 4H), 1.51-1.45 (m, 2H); $^{13}$C NMR (150 MHz, D$_2$O) δ 175.0, 174.9, 173.9, 104.5, 103.2, 102.9, 101.9, 100.3, 99.6, 79.7, 78.8, 78.7, 77.1, 75.5, 75.4, 74.8, 74.7, 74.6, 74.5, 72.9, 72.7, 72.1, 71.8, 70.8, 70.2, 70.0, 68.9, 68.9, 68.3, 68.0, 67.8, 67.5, 67.3, 62.4, 60.9, 60.3, 60.0, 51.6, 51.3, 39.7, 39.3, 28.1, 26.5, 22.3, 22.0, 22.0; HRMS (ESI-TOF, MNa$^+$) calcd for C$_{48}$H$_{83}$N$_3$O$_{34}$Na 1268.4756. found 1268.4760.

TABLE 6

Basic composition of glycosphingolipids

| | Gal | Glc | GalNAc | GlcNAc | Neu5Ac | Fuc |
|---|---|---|---|---|---|---|
| Globoseries | | | | | | |
| Globotetraose (Gb4) | 2 | 1 | 1 | 0 | 0 | 0 |
| Globopentaose (Gb5) | 3 | 1 | 1 | 0 | 0 | 0 |
| Globo H (Fucosyl-Gb5) | 3 | 1 | 1 | 0 | 0 | 1 |
| SSEA4 (Sialyl-Gb5) | 3 | 1 | 1 | 0 | 1 | 0 |
| Isoglobotetraose | 2 | 1 | 1 | 0 | 0 | 0 |
| Neolactoseries | 2 | 1 | 0 | 1 | 1 | 0 |
| Lactoseries | 2 | 1 | 0 | 1 | 1 | 0 |
| Ganglioseries | 2 | 1 | 1 | 0 | 2 | 0 |

TABLE 7

Yields of Each step of glycosylation with regeneration

| | Enzyme involvement | Product | Yield |
|---|---|---|---|
| Step 1. | GalK, AtUSP, PykF, PPA, LgtC* | allyl-Gb3 | 99% |
| Step 2. | NahK, GlmU, PykF, PPA, LgtD* | allyl-Gb4 | 96% |
| Step 3. | GalK, AtUSP, PykF, PPA, LgtD* | allyl-Gb5 | 95%** |
| Step 4a. | FKP, PykF, PPA, FutC* | allyl-Globo H | 94% |
| Step 4b. | CSS, CMK, PykF, PPA, JT-FAJ-16* | allyl-SSEA4 | 45% |

*DNA sequences were optimized for E. coli expression.
**When using pure allyl-Gb4 as an acceptor.

Example 2

One-Step Synthesis of Allyl-Gb5(SSEA3) from Allyl-Lactose

Figure 6:
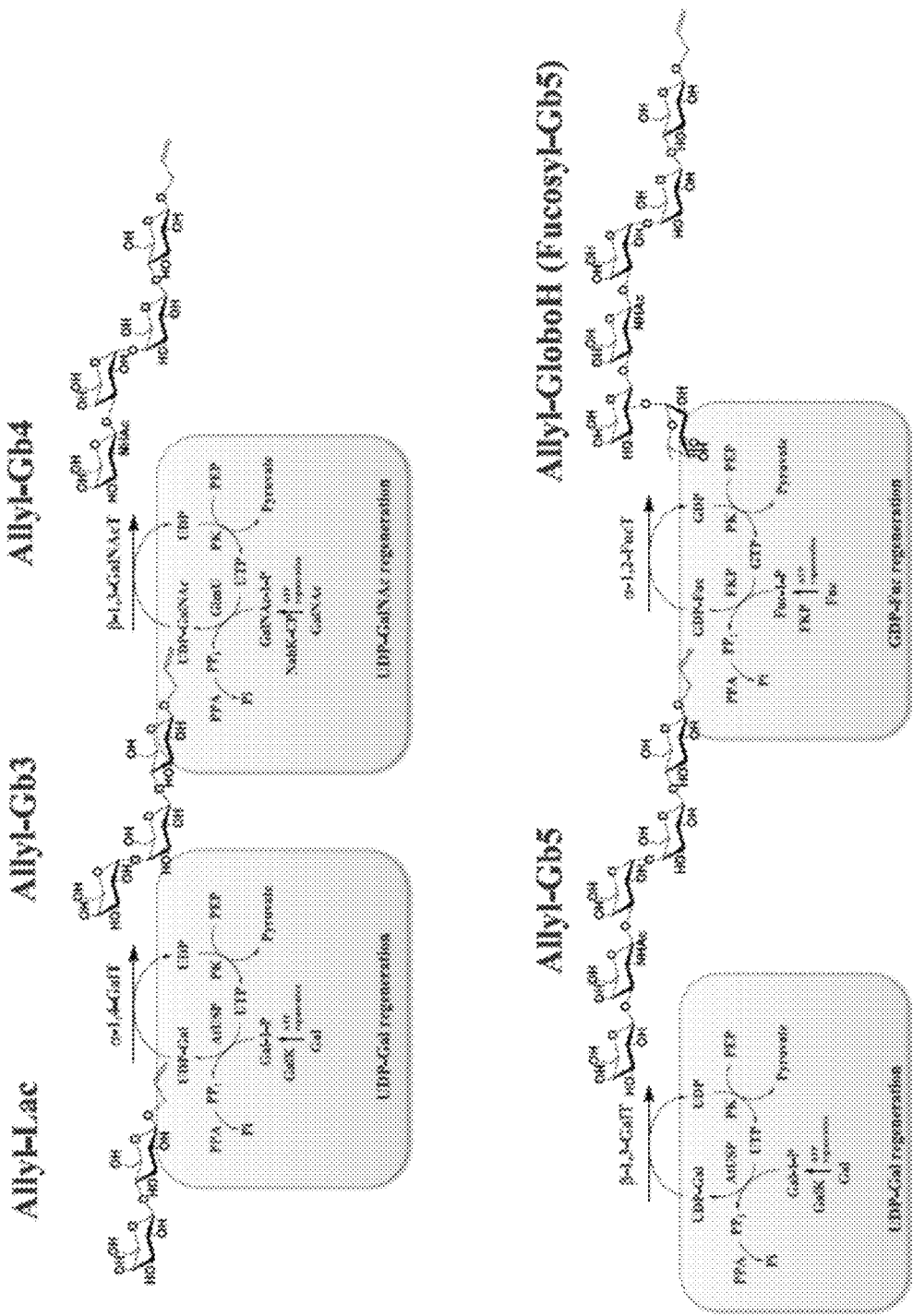
FIG. 6 depicts the enzymatic synthetic strategy in the manufacture of allyl-Globo H via the allyl-Lac→allyl-Gb3→allyl-Gb4→allyl-Gb5 pathway using a nucleotide sugar regeneration system.
Figure 7:
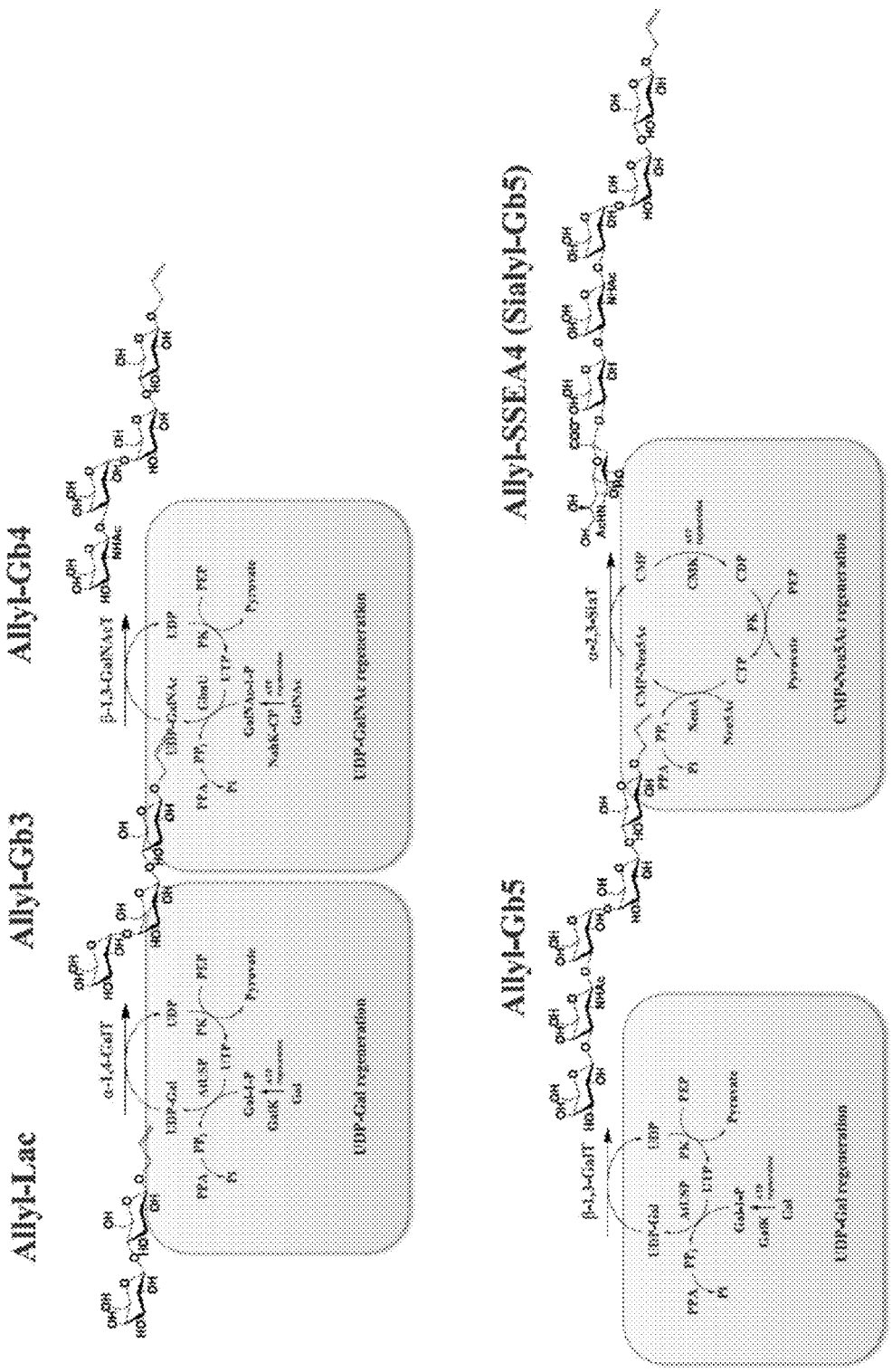
FIG. 7 depicts the enzymatic synthetic strategy in the manufacture of allyl-SSEA4 via the allyl-Lac→allyl-Gb3→allyl-Gb4→allyl-Gb5 pathway using a nucleotide sugar regeneration system.
Figure 8:
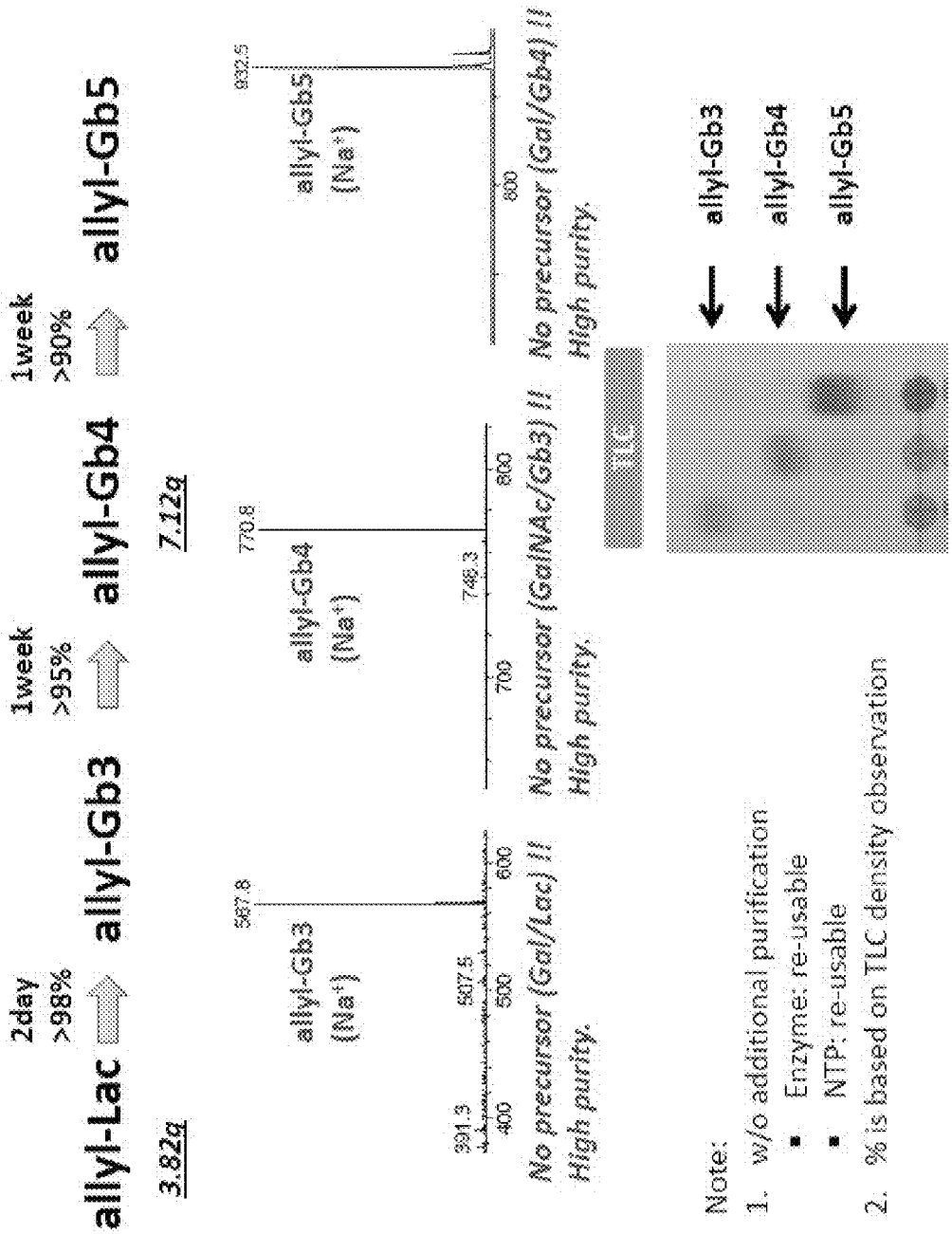
FIG. 8 depicts the high purity obtained in the biosynthesis of intermediates allyl-Gb3, allyl-Gb4, and allyl-Gb5.
Figure 9:
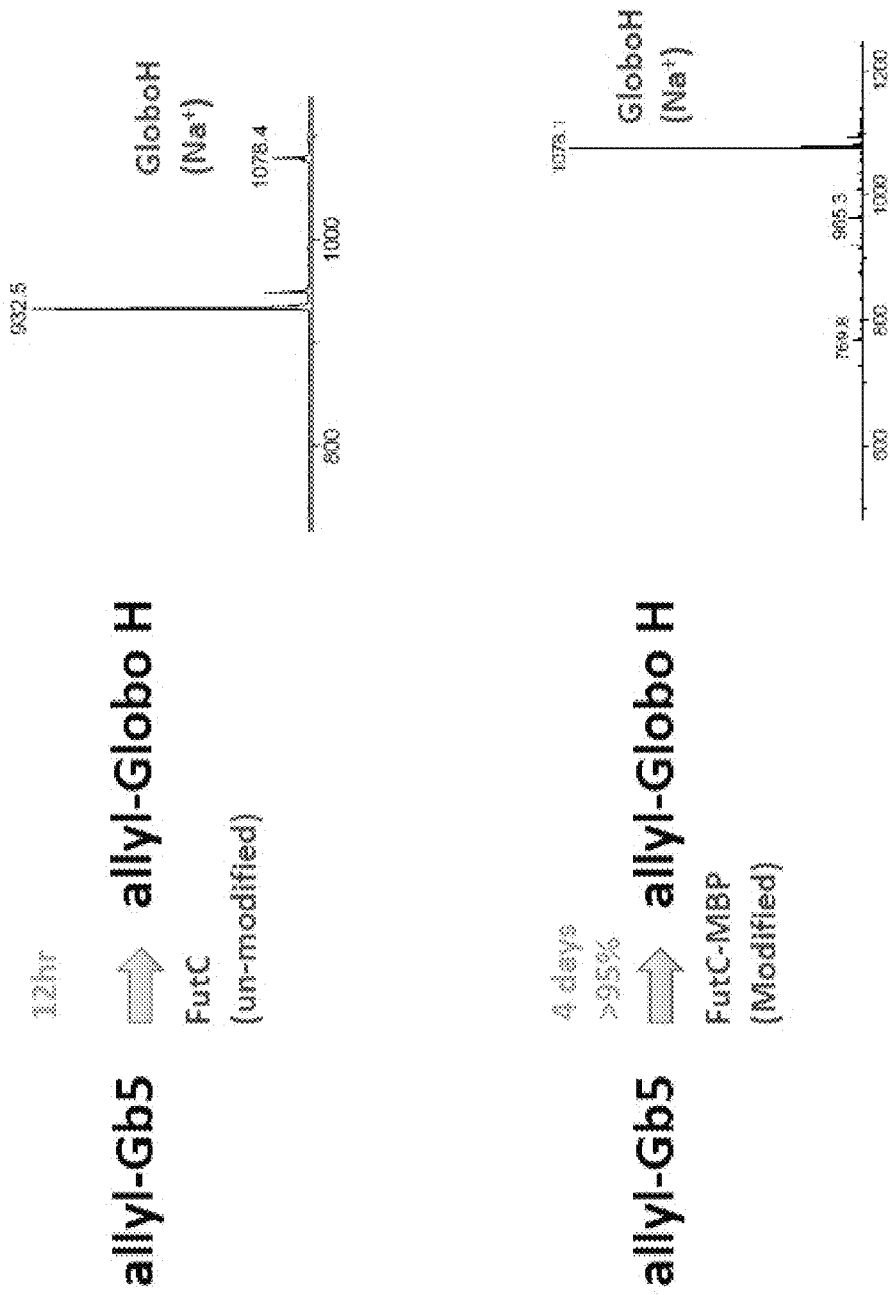
FIG. 9 depicts the high purity obtained in the biosynthesis of allyl-Globo H from allyl-Gb5 using unmodified and modified FutC.
Figure 10:
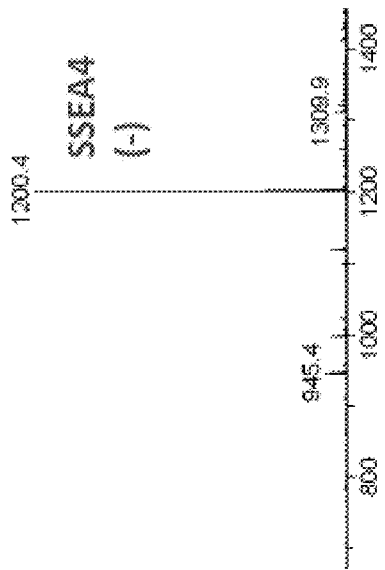
FIG. 10 depicts the high purity obtained in the biosynthesis of allyl-SSEA4 from allyl-Gb5 using JT-FAJ-16.
Figure 10:
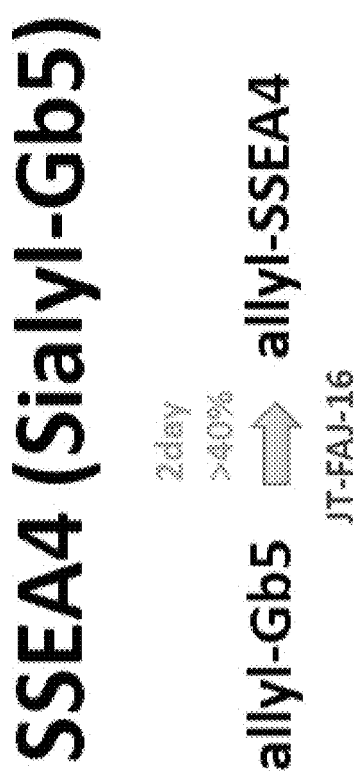

Allyl-Gb5 was synthesized from allyl-lac via a one-step chain reaction as illustrated in FIG. 6, without purifying any of the intermediates.

5 mmol Allyl-lac, 5 mmol galactose, 12 mmol PEP, 0.25 mmol ATP, 0.25 mmol UTP with 10 mM MgCl$_2$ in 100 mM Tris-HCl buffer (pH 7.5) were mixed in a flask. Enzymatic reaction was initiated by adding into the flask a suitable α1,4-galactosyltransferase (LgtC), GalK, AtUSP, PK and PPA to synthesize allyl-Gb3. The flask containing the reaction mixture was placed in a 16~50° C. incubator with gently shaking. TLC analysis was performed to monitor the synthesis process. If no further synthesis of allyl-Gb3 is observed, additional enzymes were added.

After synthesis of allyl-Gb3, another set of components, including 5 mmol of GalNAc, 12 mmol PEP, and a suitable amount of N-acetylhexosamine 1-kinase (NahK-CP), N-acetylglucosamine 1-phosphate uridylyltransferase (GlmU), PK, PPA and β1,3-N-acetylgalactosaminyltransferase (LgtD), was added into the flask. The reaction mixture thus formed was incubated under the same conditions under which allyl-Gb3 was synthesis. If no further synthesis of allyl-Gb4 is observed, additional amounts of the enzymes can be added.

After synthesis of allyl-Gb4, 5 mmol galactose and 12 mmol PEP were added into the flask without purifying the allyl-Gb4. The next galactosylation reaction was initiated by adding suitable β1,3-galactosyltransferase (LgtD), GalK, AtUSP, PK and PPA to synthesize allyl-Gb5. The flask containing the reaction mixture was placed in a 16~50° C. incubator with gently shaking. TLC was performed to monitor the synthesis process. Additional amounts of enzymes can be added if no further synthesis of allyl-Gb5 is observed. The yield of this one-step synthesis of allyl-Gb5 from allyl-lac is about 40%.

REFERENCES

1. Kannagi, R., et al., *Stage-specific embryonic antigens (SSEA-3 and -4) are epitopes of a unique globo-series ganglioside isolated from human teratocarcinoma cells.* EMBO J, 1983. 2(12): p. 2355-61.
2. Shengle, Z., et al., *Selection of tumor antigens as targets for immune attack using immunohistochemistry: I. Focus on gangliosides.* International Journal of Cancer, 1997. 73(1): p. 42-49.
3. Shengle, Z., et al., *Selection of tumor antigens as targets for immune attack using immunohistochemistry: II. Blood group-related antigens.* International Journal of Cancer, 1997. 73(1): p. 50-56.
4. Chang, W.-W., et al., *Expression of Globo H and SSEA3 in breast cancer stem cells and the involvement of fucosyl transferases 1 and 2 in Globo H synthesis.* Proceedings of the National Academy of Sciences, 2008. 105(33): p. 11667-11672.

5. Slamon, D. J., et al., *Use of Chemotherapy plus a Monoclonal Antibody against HER2 for Metastatic Breast Cancer That Overexpresses HER2*. New England Journal of Medicine, 2001. 344(11): p. 783-792.
6. Wang, Z.-G., et al., *Polyclonal antibodies from patients immunized with a globo H-keyhole limpet hemocyanin vaccine: Isolation, quantification, and characterization of immune responses by using totally synthetic immobilized tumor antigens*. Proceedings of the National Academy of Sciences of the United States of America, 2000. 97(6): p. 2719-2724.
7. Bilodeau, M. T., et al., *Total Synthesis of a Human Breast Tumor Associated Antigen*. Journal of the American Chemical Society, 1995. 117(29): p. 7840-7841.
8. Park, T. K., et al., *Total Synthesis and Proof of Structure of a Human Breast Tumor (Globo-H) Antigen*. Journal of the American Chemical Society, 1996. 118(46): p. 11488-11500.
9. Slovin, S. F., et al., *Carbohydrate vaccines in cancer: Immunogenicity of a fully synthetic globo H hexasaccharide conjugate in man*. Proceedings of the National Academy of Sciences of the United States of America, 1999. 96(10): p. 5710-5715.
10. Bosse, F., L. A. Marcaurelle, and P. H. Seeberger, *Linear Synthesis of the Tumor-Associated Carbohydrate Antigens Globo-H, SSEA-3, and Gb3*. The Journal of Organic Chemistry, 2002. 67(19): p. 6659-6670.
11. Werz, D. B., B. Castagner, and P. H. Seeberger, *Automated Synthesis of the Tumor-Associated Carbohydrate Antigens Gb-3 and Globo-H: Incorporation of α-Galactosidic Linkages*. Journal of the American Chemical Society, 2007. 129(10): p. 2770-2771.
12. Wang, Z., et al., *Multi-Component One-Pot Synthesis of the Tumor-Associated Carbohydrate Antigen Globo-H Based on Preactivation of Thioglycosyl Donors*. The Journal of Organic Chemistry, 2007. 72(17): p. 6409-6420.
13. Jeon, I., K. Iyer, and S. J. Danishefsky, *A Practical Total Synthesis of Globo-H for Use in Anticancer Vaccines*. The Journal of Organic Chemistry, 2009. 74(21): p. 8452-8455.
14. Fred, B., et al., *Synthesis of the Globo H Hexasaccharide Using the Programmable Reactivity-Based One-Pot Strategy*. Angewandte Chemie International Edition, 2001. 40(7): p. 1274-1277.
15. Hsu, C.-H., et al., *Highly Alpha-Selective Sialyl Phosphate Donors for Efficient Preparation of Natural Sialosides*. Chemistry—A European Journal, 2010. 16(6): p. 1754-1760.
16. Zhen, W., et al., *Chemoenzymatic Syntheses of Tumor-Associated Carbohydrate Antigen Globo-H and Stage-Specific Embryonic Antigen 4*. Advanced Synthesis & Catalysis, 2008. 350(11-12): p. 1717-1728.
17. Wong, C. H., S. L. Haynie, and G. M. Whitesides, *Enzyme-catalyzed synthesis of N-acetyllactosamine with in situ regeneration of uridine 5'-diphosphate glucose and uridine 5'-diphosphate galactose*. The Journal of Organic Chemistry, 1982. 47(27): p. 5416-5418.
18. Wong, C. H., R. Wang, and Y. Ichikawa, *Regeneration of sugar nucleotide for enzymic oligosaccharide synthesis: use of Gal-1-phosphate uridyltransferase in the regeneration of UDP-galactose, UDP-2-deoxygalactose, and UDP-galactosamine*. The Journal of Organic Chemistry, 1992. 57(16): p. 4343-4344.
19. Kotake, T., et al., *UDP-sugar Pyrophosphorylase with Broad Substrate Specificity Toward Various Monosaccharide 1-Phosphates from Pea Sprouts*. Journal of Biological Chemistry, 2004. 279(44): p. 45728-45736.
20. Litterer, L. A., et al., *Characterization and expression of Arabidopsis UDP-sugar pyrophosphorylase*. Plant Physiology and Biochemistry, 2006. 44(4): p. 171-180.
21. Kotake, T., et al., *Properties and Physiological Functions of UDP-Sugar Pyrophosphorylase in Arabidopsis*. Bioscience, Biotechnology, and Biochemistry, 2007. 71(3): p. 761-771.
22. Damerow, S., et al., *Leishmania UDP-sugar Pyrophosphorylase*. Journal of Biological Chemistry, 2010. 285(2): p. 878-887.
23. Yang, T. and M. Bar-Peled, *Identification of a novel UDP-sugar pyrophosphorylase with a broad substrate specificity in Trypanosoma cruzi*. Biochemical Journal, 2010. 429(3): p. 533-543.
24. Persson, K., et al., *Crystal structure of the retaining galactosyltransferase LgtC from Neisseria meningitidis in complex with donor and acceptor sugar analogs*. Nat Struct Mol Biol, 2001. 8(2): p. 166-175.
25. Koto, S., et al., *Simple preparations of alkyl and cycloalkyl α-glycosides of maltose, cellobiose, and lactose*. Carbohydrate Research, 2004. 339(14): p. 2415-2424.
26. Antoine, T., et al., *Large scale in vivo synthesis of globotriose and globotetraose by high cell density culture of metabolically engineered Escherichia coli*. Biochimie, 2005. 87(2): p. 197-203.
27. Zhang, J., et al., *Efficient chemoenzymatic synthesis of globotriose and its derivatives with a recombinant [alpha]-(1→4)-galactosyltransferase*. Carbohydrate Research, 2002. 337(11): p. 969-976.
28. Shao, J., et al., *Efficient synthesis of globoside and isogloboside tetrasaccharides by using β(1→3)N-acetylgalactosaminyltransferase/UDP-N-acetylglucosamine C4 epimerase fusion protein*. Chemical Communications, 2003 (12): p. 1422-1423.
29. Shao, J., et al., *Donor Substrate Regeneration for Efficient Synthesis of Globotetraose and Isoglobotetraose*. Appl. Environ. Microbiol., 2002. 68(11): p. 5634-5640.
30. Vanessa, B., et al., *Efficient Enzymatic Glycosylation of Peptides and Oligosaccharides from GalNAc and UTP*. ChemBioChem, 2007. 8(1): p. 37-40.
31. Nishimoto, M. and M. Kitaoka, *Identification of N-Acetylhexosamine 1-Kinase in the Complete Lacto-N-Biose I/Galacto-N-Biose Metabolic Pathway in Bifidobacterium longum*. Appl. Environ. Microbiol., 2007. 73(20): p. 6444-6449.
32. Fang, J., et al., *Systematic study on the broad nucleotide triphosphate specificity of the pyrophosphorylase domain of the N-acetylglucosamine-1-phosphate uridyltransferase from Escherichia coli K12*. Bioorganic & Medicinal Chemistry Letters, 2009. 19(22): p. 6429-6432.
33. Hood, D. W., et al., *Genetic basis for expression of the major globotetraose-containing lipopolysaccharide from H. influenzae strain Rd (RM118)*. Glycobiology, 2001. 11(11): p. 957-967.
34. Shao, J., et al., *Overexpression and biochemical characterization of [beta]-1,3-N-acetylgalactosaminyltransferase LgtD from Haemophilus influenzae strain Rd*. Biochemical and Biophysical Research Communications, 2002. 295(1): p. 1-8.
35. Randriantsoa, M., et al., *Synthesis of globopentaose using a novel [beta]1,3-galactosyltransferase activity of the Haemophilus influenzae [beta]1,3-N-acetylgalactosaminyltransferase LgtD*. FEBS Letters, 2007. 581(14): p. 2652-2656.

36. Coyne, M. J., et al., *Human Symbionts Use a Host-Like Pathway for Surface Fucosylation*. Science, 2005. 307(5716): p. 1778-1781.
37. Wang, W., et al., *Chemoenzymatic synthesis of GDP-1-fucose and the Lewis X glycan derivatives*. Proceedings of the National Academy of Sciences, 2009. 106(38): p. 16096-16101.
38. Koizumi, S., et al., *Large-scale production of GDP fucose and Lewis X by bacterial coupling*. Journal of Industrial Microbiology and Biotechnology, 2000. 25(4): p. 213-217.
39. Stein, Daniel B., Y.-N. Lin, and C.-H. Lin, *Characterization of Helicobacter pylori alpha1,2-Fucosyltransferase for Enzymatic Synthesis of Tumor-Associated Antigens*. Advanced Synthesis & Catalysis, 2008. 350(14-15): p. 2313-2321.
40. Tanner, M. E., *The enzymes of sialic acid biosynthesis*. Bioorganic Chemistry, 2005. 33(3): p. 216-228.
41. Li, Y., et al., *Pasteurella multocida CMP-sialic acid synthetase and mutants of Neisseria meningitidis CMP-sialic acid synthetase with improved substrate promiscuity*. Applied Microbiology and Biotechnology, 2011: p. 1-13.
42. Kushi, Y., et al., *Sialyltransferases of marine bacteria efficiently utilize glycosphingolipid substrates*. Glycobiology, 2010. 20(2): p. 187-198.
43. Yamamoto, T., *Marine Bacterial Sialyltransferases*. Marine Drugs, 2010. 8(11): p. 2781-2794.
44. Takakura, Y., H. Tsukamoto, and T. Yamamoto, *Molecular Cloning, Expression and Properties of an α/β-Galactoside α2,3-Sialyltransferase from Vibrio sp. JT-FAJ-16*. Journal of Biochemistry, 2007. 142(3): p. 403-412.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for enzymatically synthesizing an oligosaccharide, comprising:
   (i) producing UDP-Gal from galactose in the presence of a set of UDP-Gal regeneration enzymes, wherein the set of UDP-Gal regeneration enzymes comprises a galactokinase, an UDP-sugar pyrophosphorylase, and a pyruvate kinase;
   (ii) converting Lactose-OR$^{1A}$ into Globotriose-OR$^{1A}$ (Gb3-OR$^{1A}$) in the presence of the UDP-Gal and an alpha-1,4 galactosyltransferase, wherein R$^{1A}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group;

(iii) converting the Gb3-OR$^{1A}$ into Globotetraose-OR$^{1A}$ (Gb4-OR$^{1A}$) in the presence of UDP-GalNAc and a beta-1,3-N-acetylgalactosaminyltransferase; and (iv) converting the Gb4-OR$^{1A}$ into Globopentaose-OR$^{1A}$ (Gb5-OR$^{1A}$) in the presence of UDP-Gal and a beta-1,3-N-galactosyltransferase, wherein the method is performed without purifying intermediates, wherein the method is performed with all enzymes free of cells.

2. The method of claim 1, wherein the set of UDP-Gal regeneration enzymes further comprises pyrophosphatase.

3. The method of claim 1, wherein (i) and (ii) occur in a Gb3-synthesis reaction mixture comprising galactose, PEP, ATP, UTP, the Lac-OR$^{1A}$, the alpha-1,4-galactosyltransferase, and the set of UDP-Gal regeneration enzymes.

4. The method of claim 3, wherein, before occurrence of any enzymatic reactions, the molar ratio of the Lac-OR$^{1A}$ and galactose in the Gb3-synthesis reaction mixture is 1:1.

5. The method of claim 3, further comprising:
(a) mixing the Gb3-synthesis reaction mixture with at least GalNAc, the beta-1,3-N-acetylgalactosaminyltransferase, the N-acetylhexosamine 1-kinase, and the N-acetylglucosamine 1-phosphate uridyltransferase to form a Gb4-synthesis reaction mixture,
(b) incubating the Gb4-synthesis reaction mixture under conditions allowing conversion of Gb3-OR$^{1A}$ to Gb4-OR$^{1A}$,
(c) further incubating the Gb4-synthesis reaction mixture in the presence of a beta-1,3-galactosyltransferase under conditions allowing conversion of the Gb4-OR$^{1A}$ to Gb5-OR$^{1A}$,
(d) mixing the Gb5-OR$^{1A}$-containing reaction mixture produced in (c) with at least fucose, GTP, the alpha-1,2-fucosyltransferase, and the L-fucokinase/GDP-fucose pyrophosphorylase to form a Fucosyl-Gb5-OR$^{1A}$ reaction mixture; and
(e) incubating the Fucosyl-Gb5-OR$^{1A}$ reaction mixture under conditions allowing conversion of the Gb5-OR$^{1A}$ to Fucosyl-Gb5-OR$^{1A}$.

6. The method of claim 3, further comprising:
(a) mixing the Gb3-synthesis reaction mixture with at least GalNAc, the beta-1,3-N-acetylgalactosaminyltransferase, the N-acetylhexosamine 1-kinase, and the N-acetylglucosamine 1-phosphate uridyltransferase to form a Gb4-synthesis reaction mixture,
(b) incubating the Gb4-synthesis reaction mixture under conditions allowing conversion of Gb3-OR$^{1A}$ to Gb4-OR$^{1A}$;
(c) mixing the Gb4-OR$^{1A}$ with a beta-1,3-galactosyltransferase and the set of UDP-Gal regeneration enzymes to form a Gb5-synthesis reaction mixture;
(d) incubating the Gb5-synthesis reaction mixture under conditions allowing conversion of the Gb4-OR$^{1A}$ to Gb5-OR$^{1A}$,
(e) mixing the Gb5-OR$^{1A}$-containing reaction mixture produced in (e) with at least fucose, GTP, the alpha-1,2-fucosyltransferase, and the L-fucokinase/GDP-fucose pyrophosphorylase to form a Fucosyl-Gb5-OR$^{1A}$ reaction mixture; and
(f) incubating the Fucosyl-Gb5-OR$^{1A}$ reaction mixture under conditions allowing conversion of the Gb5-OR$^{1A}$ to Fucosyl-Gb5-OR$^{1A}$.

7. The method of claim 3, further comprising:
(a) mixing the Gb3-synthesis reaction mixture with at least GalNAc, the beta-1,3-N-acetylgalactosaminyltransferase, the N-acetylhexosamine 1-kinase, and the N-acetylglucosamine 1-phosphate uridyltransferase to form a Gb4-synthesis reaction mixture,
(b) incubating the Gb4-synthesis reaction mixture under conditions allowing conversion of Gb3-OR$^{1A}$ to Gb4-OR$^{1A}$,
(c) further incubating the Gb4-synthesis reaction mixture in the presence of a beta-1,3-galactosyltransferase under conditions allowing conversion of the Gb4-OR$^{1A}$ to Gb5-OR$^{1A}$,
(d) mixing the Gb5-OR$^{1A}$-containing reaction mixture in (c) with at least at least Neu5Ac, CTP, the alpha-2,3-sialyltransferase, the cytidine monophosphate kinase, and the CMP-sialic acid synthetase to form a Sialyl-Gb5-OR$^{1A}$ reaction mixture; and
(e) incubating the Sialyl-Gb5-OR$^{1A}$ reaction mixture under conditions allowing conversion of the Gb5-OR$^{1A}$ to Sialyl-Gb5-OR$^{1A}$.

8. The method of claim 3, further comprising:
(a) mixing the Gb3-synthesis reaction mixture with at least GalNAc, the beta-1,3-N-acetylgalactosaminyltransferase, the N-acetylhexosamine 1-kinase, and the N-acetylglucosamine 1-phosphate uridyltransferase to form a Gb4-synthesis reaction mixture,
(b) incubating the Gb4-synthesis reaction mixture under conditions allowing conversion of Gb3-OR$^{1A}$ to Gb4-OR$^{1A}$;
(c) mixing the Gb4-OR$^{1A}$ with a beta-1,3-galactosyltransferase and the set of UDP-Gal regeneration enzymes to form a Gb5-synthesis reaction mixture;
(d) incubating the Gb5-synthesis reaction mixture under conditions allowing conversion of the Gb4-OR$^{1A}$ to Gb5-OR$^{1A}$,
(e) mixing the Gb5-OR$^{1A}$ with an alpha-2,3-sialyltransferase and a set of CMP-Neu5Ac regeneration enzymes to form a Sialyl-Gb5-synthesis reaction mixture, wherein the set of CMP-Neu5Ac regeneration enzymes comprises a cytidine monophosphate kinase, a CMP-sialic acid synthetase, a pyruvate kinase, and a pyrophosphatase; and
(f) incubating the Sialyl-Gb5-synthesis reaction mixture under conditions allowing conversion of the Gb5-OR$^{1A}$ to Sialyl-Gb5-OR$^{1A}$.

9. The method of claim 1, wherein R$^{1A}$ is hydrogen, allyl, substituted alkyl, biotin, or a ceramide.

10. The method of claim 1, wherein the alpha-1,4 galactosyltransferase is LgtC from *N. meningitides*, the galactokinase is from *E. coli*, the UDP-sugar pyrophosphorylase is from *A. thaliana*, the pyruvate kinase is from *E. coli*, or the pyrophosphatase is from *E. coli*.

11. The method of claim 1, further comprising:
(v) producing the UDP-GalNAc from GalNAc in the presence of a set of UDP-GalNAc regeneration enzymes, wherein the set of UDP-GalNAc regeneration enzymes comprises an N-acetylhexosamine 1-kinase, an N-acetylglucosamine 1-phosphate uridyltransferase, and a pyruvate kinase, and a pyrophosphatase.

12. The method of claim 11, wherein (iii) and (v) occur in a Gb4-OR$^{1A}$-synthesis reaction mixture comprising GalNAc, PEP, ATP, UTP, the Gb3-OR$^{1A}$, the beta-1,3-N-acetylgalactosaminyltransferase, and the set of UDP-GalNAc regeneration enzymes.

13. The method of claim 12, wherein the Gb4-synthesis reaction mixture is prepared by mixing the Gb3-OR$^{1,4}$-synthesis reaction mixture with at least GalNAc, the beta-1,3-N-acetylgalactosaminyltransferase, the N-acetylhexosamine 1-kinase, and the N-acetylglucosamine 1-phosphate uridyltransferase.

14. The method of claim 1, wherein the beta-1,3-N-acetylgalactosaminyltransferase is LgtD from *H. influenza*, the N-acetylhexosamine 1-kinase is from *B. longum*, or the N-acetylglucosamine 1-phosphate uridyltransferase is from *E. coli*.

15. The method of claim 1, further comprising isolating the Gb4-OR$^{1,4}$.

16. The method of claim 1, wherein (iv) occurs in a Gb5-OR$^{1,4}$-synthesis reaction mixture comprising galactose, PEP, ATP, UTP, the Gb4-OR$^{1,4}$, the beta-1,3-galactosyltransferase, and the set of UDP-Gal regeneration enzymes.

17. The method of claim 1, wherein the beta-1,3-galactosyltransferase is LgtD from *H. influenza*.

18. The method of claim 1, further comprising isolating the Gb5-OR$^{1,4}$.

19. The method of claim 1, further comprising:
(vi) converting the Gb5-OR$^{1,4}$ into Fucosyl-Gb5-OR$^{1,4}$ in the presence of GDP-Fuc and an alpha-1,2-fucosyltransferase.

20. The method of claim 19, further comprising:
(vii) producing the GDP-Fuc from fucose in the presence of a set of GDP-Fuc regeneration enzymes, wherein the set of GDP-Fuc regeneration enzymes comprises a L-fucokinase/GDP-fucose pyrophosphorylase, a pyruvate kinase, and a pyrophosphatase.

21. The method of claim 20, wherein (vi) and (vii) occur in a Fucosyl-Gb5-synthesis reaction mixture comprising fucose, ATP, GTP, PEP, the Gb5-OR, the alpha-1,2-fucosyltransferase, and the set of GDP-Fuc regeneration enzymes.

22. The method of claim 21, wherein the Fucosyl-Gb5-synthesis reaction mixture is prepared by mixing the Gb5-synthesis reaction mixture with at least fucose, GTP, the alpha-1,2-fucosyltransferase, and the L-fucokinase/GDP-fucose pyrophosphorylase.

23. The method of claim 20, wherein the L-fucokinase/GDP-fucose pyrophosphorylase is from *B. fragilis*, or the alpha-1,2-fucosyltransferase is from *H. pylori*.

24. The method of claim 19, further comprising isolating the Fucosyl-Gb5-OR$^{1,4}$.

25. The method of claim 1, further comprising:
(viii) converting the Gb5-OR$^{1,4}$ into Sialyl-Gb5-OR$^{1,4}$ in the presence of CMP-Neu5Ac and an alpha-2,3-sialyltransferase.

26. The method of claim 25, further comprising:
(ix) producing the CMP-Neu5Ac from Neu5Ac in the presence of a set of CMP-Neu5Ac regeneration enzymes, wherein the set of CMP-Neu5Ac regeneration enzymes comprises a cytidine monophosphate kinase, a CMP-sialic acid synthetase, a pyruvate kinase, and optionally a pyrophosphatase.

27. The method of claim 26, wherein (viii) and (ix) occur in a Sialyl-Gb5-synthesis reaction mixture comprising Neu5Ac, CTP, PEP, the Gb5-OR$^{1,4}$, the alpha-2,3-sialyltransferase, and the set of CMP-Neu5Ac regeneration enzymes.

28. The method of claim 27, wherein the Sialyl-Gb5-synthesis reaction mixture is prepared by mixing the Gb5-synthesis reaction mixture with at least Neu5Ac, CTP, the alpha-2,3-sialyltransferase, the cytidine monophosphate kinase, and the CMP-sialic acid synthetase.

29. The method of claim 25, wherein the alpha-2,3-sialyltransferase is from *M. bacteria*, the cytidine monophosphate kinase is from *E. coli*, or the CMP-sialic acid synthetase is from *P. multocida*.

30. The method of claim 25, further comprising isolating the Sialyl-Gb5-OR$^{1,4}$.

31. The method of claim 1, wherein at least one enzyme is immobilized on a support member.

32. The method of claim 1, wherein the Lac-OR$^{1,4}$, Gb3-OR$^{1,4}$, Gb4-OR$^{1,4}$, or Gb5-OR$^{1,4}$ is immobilized on a support member.

* * * * *

```
                              SEQUENCE LISTING

<160> NUMBER OF SEQ ID NOS: 30

<210> SEQ ID NO 1
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 1
ctgtattttc agggagcgat cgctatgagt ctgaaagaaa aaacab                    46

<210> SEQ ID NO 2
<211> LENGTH: 44
<212> TYPE: DNA
<213> ORGANISM: Artificial Sequence
```

```
<220> FEATURE:
<223> OTHER INFORMATION: Synthetic oligonucleotide

<400> SEQUENCE: 2
gcctcgagtc attacgttta aactcagcac tgtcctgctc cttg                    44

<210> SEQ ID NO 3
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 3
ctgtattttc agggagcgat cgctatggct tctacggttg attc                    44

<210> SEQ ID NO 4
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 4
gcctcgagtc attacgttta aactcaatct tcaacagaaa atttgc                  46

<210> SEQ ID NO 5
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 5
gatataccat ggaaatggac atcgttttcg cggcg                              35

<210> SEQ ID NO 6
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 6
gtggtgctcg aggtagattt tacgcaggaa acg                                33

<210> SEQ ID NO 7
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 7
ctgtattttc agggagcgat cgctatgaac aagacttatg attttaaaag              50

<210> SEQ ID NO 8
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 8
gcctcgagtc attacgttta aacttaaatg tatgaatata ctatcttc                48
```

```
<210> SEQ ID NO 9
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 9
ctgtattttc agggagcgat cgctatgttg aataatgcta tgagc            45

<210> SEQ ID NO 10
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 10
gcctcgagtc attacgttta aactcacttt ttctttaccg gacg             44

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
gatataccat ggaaaactgc ccgctggttt ct                          32

<210> SEQ ID NO 12
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 12
gtggtgctcg aggaagataa cgttgatttt acgg                        34

<210> SEQ ID NO 13
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 13
cagggagcga tcgctatgca aaaactacta tcttta                      36

<210> SEQ ID NO 14
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 14
cattacgttt aaacttatga tcgtgatact tggaa                       35

<210> SEQ ID NO 15
<211> LENGTH: 45
<212> TYPE: DNA
<213> ORGANISM: Artificial Sequence
<220> FEATURE:
<223> OTHER INFORMATION: Synthetic oligonucleotide
```

```
<400> SEQUENCE: 15
ctgtattttc agggagcgat cgctatggcg ttcaaagttg ttcag          45

<210> SEQ ID NO 16
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 16
gcctcgagtc attacgttta aacttacgcg ttgtatttct gagat          45

<210> SEQ ID NO 17
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 17
cagggagcga tcgctatgac ggcaattgcc ccggtt                    36

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
cattacgttt aaacttatgc gagagccaat ttctg                     35

<210> SEQ ID NO 19
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 19
gatataccat ggaaacaaat attgcgatca ttcctg                    36

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20
gtggtgctcg agtttattgg ataaaatttc cgcgag                    36

<210> SEQ ID NO 21
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 21
gatataccat ggaaatgaac aacgacaact ctacc                     35
```

<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 22
gtggtgctcg aggatgtcag agatcagttt gatg          34

<210> SEQ ID NO 23
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 23
ctgtattttc agggagcgat cgctatgaaa aagaccaaaa ttgtttg          47

<210> SEQ ID NO 24
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 24
gcctcgagtc attacgttta aacttacagg acgtgaacag atg          43

<210> SEQ ID NO 25
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 25
cagggagcga tcgctatgag cttactcaac gtccct          36

<210> SEQ ID NO 26
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 26
cattacgttt aaacttattt attctttgcg cgctc          35

<210> SEQ ID NO 27
<211> LENGTH: 936
<212> TYPE: DNA
<213> ORGANISM: Escherichia coli

<400> SEQUENCE: 27
atggacatcg ttttcgcggc ggacgacaac tacgcggcgt acctgtgcgt tgcggcgaaa          60
tctgttgaag cggcgcaccc ggacaccgaa atccgtttcc acgttctgga cgcgggtatc         120
tctgaagcga accgtgcggc ggttgcggcg aacctgcgtg gtggtggtgg taacatccgt         180
ttcatcgacg ttaacccgga agacttcgcg ggtttcccgc tgaacatccg tcacatctct         240
atcaccacct acgcgcgtct gaaactgggt gaatacatcg cggactgcga caaagttctg         300
tacctggaca tcgacgttct ggttcgtgac tctctgaccc cgctgtggga caccgacctg         360

```
ggtgacaact ggctgggtgc gtgcatcgac ctgttcgttg aacgtcagga aggttacaaa      420
cagaaaatcg gtatggcgga cggtgaatac tacttcaacg cgggtgttct gctgatcaac      480
ctgaaaaaat ggcgtcgtca cgacatcttc aaaatgtctt gcgaatgggt tgaacagtac      540
aaagacgtta tgcagtacca ggaccaggac atcctgaacg gtctgttcaa aggtggtgtt      600
tgctacgcga actctcgttt caacttcatg ccgaccaact acgcgttcat ggcgaaccgt      660
ttcgcgtctc gtcacaccga cccgctgtac cgtgaccgta ccaacaccgt tatgccggtt      720
gcggtttctc actactgcgg tccggcgaaa ccgtggcacc gtgactgcac cgcgtggggt      780
gcggaacgtt tcaccgaact ggcgggttct ctgaccaccg ttccggaaga atggcgtggt      840
aaactggcgg ttccgcaccg tatgttctct accaaacgta tgctgcagcg ttggcgtcgt      900
aaactgtctg cgcgtttcct gcgtaaaatc tactga                               936

<210> SEQ ID NO 28
<211> LENGTH: 972
<212> TYPE: DNA
<213> ORGANISM: Escherichia coli

<400> SEQUENCE: 28
atggaaaact gcccgctggt ttctgttatc gtttgcgcgt acaacgcgga acagtacatc       60
gacgaatcta tctcttctat catcaaccag acctacgaaa acctggaaat catcgttatc      120
aacgacggtt ctaccgacct gaccctgtct cacctggaag aaatctctaa actggacaaa      180
cgtatcaaaa tcatctctaa caaatacaac ctgggtttca tcaactctct gaacatcggt      240
ctgggttgct ctctggtaa atacttcgcg cgtatggacg cggacgacat cgcgaaaccg      300
tcttggatcg aaaaaatcgt tacctacctg gaaaaaaacg accacatcac cgcgatgggt      360
tcttacctgg aaatcatcgt tgaaaaagaa tgcggtatca tcggttctca gtacaaaacc      420
ggtgacatct ggaaaaaccc gctgctgcac aacgacatct gcgaagcgat gctgttctac      480
aacccgatcc acaacaacac catgatcatg cgtgcgaacg tttaccgtga acacaaactg      540
atcttcaaca agactaccc gtacgcggaa gactacaaat ctggtctga gtttctcgt      600 ctgggttgcc tggcgaacta cccggaagcg ctggttaaat accgtctgca cggtaaccag      660
acctcttctg tttacaacca cgaacagaac gaaaccgcga aaaaaatcaa acgtgaaaac      720
atcacctact acctgaacaa aatcggtatc gacatcaaag ttatcaactc tgtttctctg      780
ctggaaatct accacgttga caaatctaac aaagttctga atctatcct gtacgaaatg      840 tacatgtctc tggacaaata caccatcacc tctctgctgc acttcatcaa ataccacctg      900
gaactgttcg acctgaaaca gaacctgaaa atcatcaaaa aattcatccg taaaatcaac      960
gttatcttct ag                                                          972

<210> SEQ ID NO 29
<211> LENGTH: 903
<212> TYPE: DNA
<213> ORGANISM: Escherichia coli

<400> SEQUENCE: 29
atggcgttca agttgttca gatctgcggt ggtctgggta ccagatgtt ccagtacgcg        60 ttcgcgaaat ctctgcagaa acactctaac accccggttc tgctggacat cacctctttc      120
gactggtctg accgtaaaat gcagctggaa ctgttcccga tcgacctgcc gtacgcgtct      180
gcgaaagaaa tcgcgatcgc gaaaatgcag cacctgccga actggttcg tgacgcgctg      240 aaatgcatgg gtttcgaccg tgtttctcag gaaatcgttt tcgaatacga accgaaactg      300
```

```
ctgaaaccgt ctcgtctgac ctacttcttc ggttacttcc aggacccgcg ttacttcgac      360
gcgatctctc cgctgatcaa acagaccttc accctgccgc cgccgccgga aaacaacaaa      420
aacaacaaca aaaagaaga agaataccag tgcaaactgt ctctgatcct ggcggcgaaa       480
aactctgttt tcgttcacat ccgtcgtggt gactacgttg gtatcggttg ccagctgggt      540
atcgactacc agaaaaaagc gctggaatac atggcgaaac gtgttccgaa catggaactg      600
ttcgttttct gcgaagacct ggaattcacc cagaacctgg acctgggtta cccgttcatg      660
gacatgacca cccgtgacaa agaagaagaa gcgtactggg acatgctgct gatgcagtct      720
tgccagcacg gtatcatcgc gaactctacc tactcttggt gggcggcgta cctgatcgaa      780
aacccggaaa aaatcatcat cggtccgaaa cactggctgt tcggtcacga aaacatcctg      840
tgcaaagaat gggttaaaat cgaatctcac ttcgaagtta aatctcagaa atacaacgcg      900
taa                                                                    903

<210> SEQ ID NO 30
<211> LENGTH: 1146
<212> TYPE: DNA
<213> ORGANISM: Escherichia coli

<400> SEQUENCE: 30
atgaacaacg acaactctac caccaccaac aacaacgcga tcgaaatcta cgttgaccgt       60
gcgaccctgc cgaccatcca gcagatgacc aaaatcgttt ctcagaaaac ctctaacaaa      120
aaactgatct cttggtctcg ttaccogatc accgacaaat ctctgctgaa aaaaatcaac      180
gcggaattct tcaaagaaca gttcgaactg accgaatctc tgaaaaacat catcctgtct      240
gaaaacatcg acaacctgat catccacggt aacaccctgt ggtctatcga cgttgttgac      300
atcatcaaag aagttaacct gctgggtaaa acatcccga tcgaactgca cttctacgac      360
gacggttctg cggaatacgt tcgtatctac gaattctcta aactgccgga atctgaacag      420
aaatacaaaa cctctctgtc taaaaacaac atcaaattct ctatcgacgg taccgactct      480
ttcaaaaaca ccatcgaaaa catctacggt ttctctcagc tgtacccgac cacctaccac      540
atgctgcgtg cggacatctt cgacaccacc ctgaaaatca acccgctgcg tgaactgctg      600
tctaacaaca tcaaacagat gaaatgggac tacttcaaag acttcaacta caaacagaaa      660
gacatcttct actctctgac caacttcaac ccgaaagaaa tccaggaaga cttcaacaaa      720
aactctaaca aaaacttcat cttcatcggt tctaactctg cgaccgcgac cgcggaagaa      780
cagatcaaca tcatctctga agcgaaaaaa gaaaactctt ctatcatcac caactctatc      840
tctgactacg acctgttctt caaaggtcac ccgtctgcga ccttcaacga acagatcatc      900
aacgcgcacg acatgatcga atcaacaac aaaatcccgt tcgaagcgct gatcatgacc      960
ggtatcctgc cggacgcggt tggtggtatg ggttcttctg ttttcttctc tatcccgaaa     1020
gaagttaaaa acaaattcgt tttctacaaa tctggtaccg acatcgaaaa caactctctg     1080
atccaggtta tgctgaaact gaacctgatc aaccgtgaca acatcaaact gatctctgac     1140
atctaa                                                                1146
```